US012616750B2

(12) United States Patent
Deutsch et al.

(10) Patent No.: US 12,616,750 B2
(45) Date of Patent: May 5, 2026

(54) COMBINATION THERAPY UTILIZING DNA ALKYLATING AGENTS AND ATR INHIBITORS

(71) Applicant: Merck Patent GmbH, Darmstadt (DE)

(72) Inventors: Carl Deutsch, Heppenheim (DE); Birgit Piater, Darmstadt (DE); Nicolas Rasche, Darmstadt (DE); Heike Dahmen, Darmstadt (DE); Frank Zenke, Darmstadt (DE); Astrid Zimmermann, Muehltal (DE); Marcel Rieker, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 233 days.

(21) Appl. No.: 17/285,137

(22) PCT Filed: Oct. 14, 2019

(86) PCT No.: PCT/EP2019/077784
§ 371 (c)(1),
(2) Date: Apr. 14, 2021

(87) PCT Pub. No.: WO2020/078905
PCT Pub. Date: Apr. 23, 2020

(65) Prior Publication Data

US 2021/0369705 A1 Dec. 2, 2021

(30) Foreign Application Priority Data

Oct. 15, 2018 (EP) .................................... 18200527

(51) Int. Cl.
*A61K 45/06* (2006.01)
*A61K 31/497* (2006.01)
*A61K 47/68* (2017.01)

(52) U.S. Cl.
CPC ............ *A61K 45/06* (2013.01); *A61K 31/497* (2013.01); *A61K 47/6803* (2017.08)

(58) Field of Classification Search
None
See application file for complete search history.

(56) References Cited

U.S. PATENT DOCUMENTS 9,421,278 B2 * 8/2016 Dokter ............... A61K 47/6809
2015/0336952 A1 * 11/2015 Barlaam ................ A61K 45/06 546/82
2015/0359797 A1 12/2015 Helleday et al.
2018/0303829 A1 10/2018 Pollard et al.
2022/0249489 A1 8/2022 Helleday et al.
2023/0106592 A1 4/2023 Pollard et al.

FOREIGN PATENT DOCUMENTS

JP 2017524673 A 8/2017
JP 2018529713 A 10/2018

OTHER PUBLICATIONS

Vendetti et al., Oncotarget 6(42): 44289-44305 (Year: 2015).*
Lloyd et al. Protein Engineering, Design & Selection 22: 159-168 (Year: 2009).*
Edwards et al., J Mol Biol. 334(1): 103-118 (Year: 2003).*
Yu et al., Investigative Ophthalmology & Visual Science 49(2): 522-527 (Year: 2008).*
Strop et al., Chemistry and Biology 20: 161-167 (Year: 2013).*
Yao et al., Drug Discovery Today 26(8): 1857-1874 (Year: 2021).*
Tol et al., N Engl J Med. 5;360(6):563-72 (Year: 2009).*
Riekel, Marcel: Targeted Combination Therapy: Discovery and Evaluation of Synergistic Anticancer Effects of Anti-HER2-Duocarmycin Antibody-Drug Conjugates Combined with Aug. 31, 2018 (Aug. 31, 2018), XP55661435, 31 Darmstadt Retrieved from the Internet: URL:https://tuprints.ulb.tu-darmstadt.de/8 615/7/2019-06-13 PHD thesis-Rieker.pdf [retrieved on Jan. 23, 2020].
Ronald C. Elgersma et al: Design, Synthesis, and Evaluation of Linker-Duocarmycin Payloads: Toward Selection of HER2-Targeting Antibody-Drug Conjugate SYD98511 , Molecular Pharmaceutics vol. 12, No. 6, Jun. 1, 2015, pp. 1813-1835.
Ying Fu et al:DNA damaging agent-based antibody-drug conjugates for cancer therapy11 , Antibody Therapeutics, vol. 1, No. 2, Aug. 30, 2018 (Aug. 30, 2018), pp. 43-53.
Kevin M. Foote et al: Discovery of 4-{4-[(3 R)-3-Methylmorpholin-4-yl]-6-[1-(methylsulfonyl)cyclopropyl]pyrimidin-2-yl}-1 H-ndole (AZ20): A Potent and Selective Inhibitor of ATR Protein Kinase with Monotherapy in Vivo Antitumor Activity , Journal of Medicinal Chemistry, vol. 56, No. 5, Mar. 1, 2013 (Mar. 1, 2013), pp. 2125-2138.
International Search Report PCT/EP2019/077784 dated Feb. 6, 2020 (pp. 1-4).

* cited by examiner

*Primary Examiner* — Phuong Huynh
(74) *Attorney, Agent, or Firm* — Millen, White, Zelano & Branigan P.C.; Ryan R. Pool

(57) ABSTRACT

The present invention relates to synergistic combinations of DNA-alkylating ADCs and ATR inhibitors.

12 Claims, 26 Drawing Sheets

Specification includes a Sequence Listing.

Astra Zeneca

AZ20 X=O, Y=CH

AZD6738 X=NH, Y=N

Merck

ATRi 1

Bayer

BAY1895344

BAY73

BAY286

Vertex

VE-822

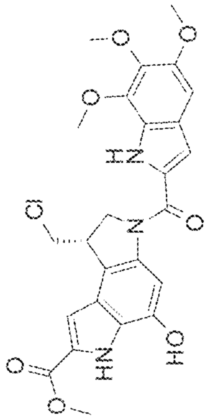
[redacted]
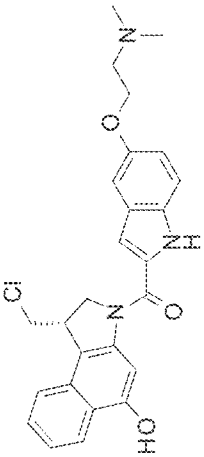
[redacted]
FIG. 6
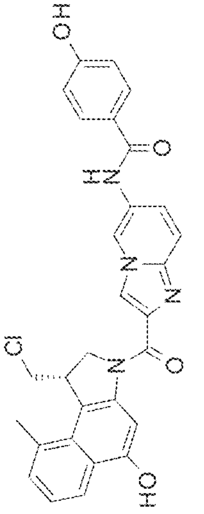
[redacted]

SEQUENCE LISTING

```
<160> NUMBER OF SEQ ID NOS: 33

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1

gcaacaguau uucgguaua                                                  19


<210> SEQ ID NO 2
<211> LENGTH: 19
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 2
ggacuucucu ccaguaaac 19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
aaagauagau gguacaaca 19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
agauaugaag cgugccgua 19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gagaaaggau uguagacua 19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gcaacucgcc uaacagaua 19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ccacgaaugu uaacucuau 19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 8
ccgcuaaucu ucuaacauu 19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 9
gcacauaccg ccugagucu 19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 10
ccaccaaggu uuucgauug 19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 11
gcucuucaau gacucaaca 19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 12
ucucaaggcc uccuaauag 19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 13
uagcgacuaa acacaucaa 19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 14
uagcgacuaa acacaucaa 19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 15
uagcgacuaa acacaucaa 19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 16
augaacguga auugcucaa 19

<210> SEQ ID NO 17
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

-continued

```
        195                 200                 205

Pro Ser Asn Thr Lys Val Asp Lys Lys Val Glu Pro Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 18
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Lys Leu Pro Val Arg Leu Leu Val Leu Met Phe Trp Ile Pro Ala
1               5                   10                  15

Ser Leu Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Asn Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95
```

-continued

```
Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gly Gly Gly Gly Ser Gly Gly
225                 230                 235                 240

Gly Gly Ser Gly Gly Gly Gly Ser Leu Pro Glu Thr Gly Ser
                245                 250


<210> SEQ ID NO 19
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 20
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

```
Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Leu Pro Glu Thr Gly Ser
    450                 455


<210> SEQ ID NO 21
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Leu Leu Thr Gln Ser Pro Val Ile Leu Ser Val Ser Pro Gly
```

-continued

```
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Leu Pro Glu Thr Gly Ser
225                 230                 235


<210> SEQ ID NO 22
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Leu Pro Glu Thr Gly Ser
    210                 215                 220


<210> SEQ ID NO 23
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Leu Leu Ile
        35                  40                  45

Tyr Tyr Thr Thr Thr Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Thr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Leu Pro Glu Thr Gly Ser
225                 230                 235


<210> SEQ ID NO 24
<211> LENGTH: 446
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 24

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Ser Leu Thr Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Lys Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
```

```
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 25
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Gly Lys Ala Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Val Ala Thr Tyr Tyr Cys Gln Gln Asn Tyr Asn Trp Pro Thr
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Phe Ser Leu Thr Asn Tyr Gly
145                 150                 155                 160

Val His Trp Met Arg Gln Ala Pro Gly Gln Gly Leu Glu Trp Ile Gly
                165                 170                 175

Val Ile Trp Ser Gly Gly Asn Thr Asp Tyr Asn Thr Pro Phe Thr Ser
            180                 185                 190

Arg Val Thr Ile Thr Ser Asp Lys Ser Thr Ser Thr Ala Tyr Met Glu
        195                 200                 205

Leu Ser Ser Leu Arg Ser Glu Asp Thr Ala Val Tyr Tyr Cys Ala Arg
    210                 215                 220

Ala Leu Thr Tyr Tyr Asp Tyr Glu Phe Ala Tyr Trp Gly Gln Gly Thr
225                 230                 235                 240

Leu Val Thr Val Ser Ser
                245


<210> SEQ ID NO 26
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 26

```
Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Ser Tyr Ala Met Ser Trp Val Arg Gln Ala Pro Gly Lys Gly
    50                  55                  60

Leu Glu Trp Val Ser Ala Ile Ser Gly Ser Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Asp Arg Arg Ile Thr His Thr Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Phe Arg Pro Glu Val
        355                 360                 365

His Leu Leu Pro Pro Ser Arg Glu Glu Met Thr Lys Asn Gln Val Ser
    370                 375                 380

Leu Thr Cys Leu Ala Arg Gly Phe Tyr Pro Lys Asp Ile Ala Val Glu
385                 390                 395                 400

Trp Glu Ser Asn Gly Gln Pro Glu Asn Asn Tyr Lys Thr Thr Pro Ser
                405                 410                 415
```

```
Arg Gln Glu Pro Ser Gln Gly Thr Thr Thr Phe Ala Val Thr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Thr Ile
    450                 455                 460

Ser Leu Ser Pro Gly Lys
465                 470
```

<210> SEQ ID NO 27
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Met Glu Thr Asp Thr Leu Leu Leu Trp Val Leu Leu Leu Trp Val Pro
1               5                   10                  15

Gly Ser Thr Gly Glu Pro Val Leu Thr Gln Pro Pro Ser Val Ser Val
            20                  25                  30

Ala Pro Gly Glu Thr Ala Thr Ile Pro Cys Gly Gly Asp Ser Leu Gly
        35                  40                  45

Ser Lys Ile Val His Trp Tyr Gln Gln Arg Pro Gly Gln Ala Pro Leu
    50                  55                  60

Leu Val Val Tyr Asp Asp Ala Ala Arg Pro Ser Gly Ile Pro Glu Arg
65                  70                  75                  80

Phe Ser Gly Ser Lys Ser Gly Thr Thr Ala Thr Leu Thr Ile Ser Ser
                85                  90                  95

Val Glu Ala Gly Asp Glu Ala Asp Tyr Phe Cys Gln Val Tyr Asp Tyr
            100                 105                 110

His Ser Asp Val Glu Val Phe Gly Gly Gly Thr Lys Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Lys Ser Tyr Ser Cys Gln Val Thr His Glu Gly Ser Thr Val
    210                 215                 220

Glu Lys Thr Val Ala Pro Thr Glu Cys Ser Leu Pro Glu Thr Gly Ser
225                 230                 235                 240
```

<210> SEQ ID NO 28
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Met Glu Thr Asp Thr Leu Leu Leu Trp Val Leu Leu Leu Trp Val Pro
1               5                   10                  15

Gly Ser Thr Gly Glu Pro Val Leu Thr Gln Pro Pro Ser Val Ser Val
            20                  25                  30

Ala Pro Gly Glu Thr Ala Thr Ile Pro Cys Gly Gly Asp Ser Leu Gly
        35                  40                  45

Ser Lys Ile Val His Trp Tyr Gln Gln Arg Pro Gly Gln Ala Pro Leu
    50                  55                  60

Leu Val Val Tyr Asp Asp Ala Ala Arg Pro Ser Gly Ile Pro Glu Arg
65                  70                  75                  80

Phe Ser Gly Ser Lys Ser Gly Thr Thr Ala Thr Leu Thr Ile Ser Ser
                85                  90                  95

Val Glu Ala Gly Asp Glu Ala Asp Tyr Phe Cys Gln Val Tyr Asp Tyr
            100                 105                 110

His Ser Asp Val Glu Val Phe Gly Gly Gly Thr Lys Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Lys Ser Tyr Ser Cys Gln Val Thr His Glu Gly Ser Thr Val
    210                 215                 220

Glu Lys Thr Val Ala Pro Thr Glu Cys Ser Leu Pro Glu Thr Gly Ser
225                 230                 235                 240


<210> SEQ ID NO 29
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Arg Ile Thr His Thr Tyr Trp Gly Gln Gly Thr Leu
            100                 105                 110

Val Thr Val Ser Ser Ala Ser Thr Lys Gly Pro Ser Val Phe Pro Leu
```

-continued

```
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Gly Gly Ser Gly Gly Gly Gly Ser Gly Gly Gly Gly Ser Leu
1               5                   10                  15

Pro Glu Thr Gly Ser
            20
```

-continued

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Leu Pro Glu Thr Gly Ser
1 5

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 32
uaaggcuaug aagagauac 19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 33
auguauuggc cuguauuag 19

COMBINATION THERAPY UTILIZING DNA ALKYLATING AGENTS AND ATR INHIBITORS

SEQUENCE LISTING

The instant application contains a Sequence Listing which has been submitted electronically in ASCII format and is hereby incorporated by reference in its entirety. Said ASCII copy, created on Oct. 6, 2025, is named MERCK-5017_SL.txt and is 44,414 bytes in size.

FIELD OF THE INVENTION

The present invention relates to a combination therapy utilizing ATR inhibitors and a DNA alkylating agent attached to an antibody molecule, thus forming an antibody drug conjugate, for the treatment of cancer.

BACKGROUND OF THE INVENTION

While the global cancer burden is still high with 10-20 million people being diagnosed with cancer and up to 10 million cancer-related deaths yearly, academia and industry are seeking to develop more and more sophisticated therapies to combat cancer.

Duocarmyins are a class of highly potent antitumour drug candidates. Synthetic analogs of duocarmycins include adozelesin, bizelesin, and carzelesin. As members of the cyclopropylpyrroloindole family, these investigational drugs have progressed into clinical trials for the treatment of cancer. The first member of the duocarmycin family to be evaluated in vivo was CC-1065, and despite showing moderate antitumor activity, hepatic toxicity limited its effectiveness. At this point in time, clinical development is not reported for any member of the duocarmycin family.

In efforts to improve the therapeutic index of duocarmycin-based therapeutics, several ADCs have been developed including BMS-936561 (anti-CD70) and SYD985 (anti-HER2). BMS-936561 was first analyzed in patients with advanced clear cell carcinoma and B-cell non-Hodgkin lymphoma; however, the clinical trial was stopped during Phase I despite being tolerated at doses up to 8 mpk. More recently, Synthon generated SYD985 (trastuzumab duocarmycin), which utilizes a duocarmycin prodrug known as seco-DUBA conjugated with a cleavable linker to trastuzumab, as an alternative to ado-trastuzumab emtansine. SYD985 is currently in phase III clinical study.

Despite of several attempts no drug based on a member of the duocarmycin family has been approved for human therapy yet, neither based on a duocarmycin as such nor as an duocarmycin bearing ADC.

There is still a highly unmet need in the art for improved cancer therapies, both in terms of effectiveness as well as safety. Establishment of combination therapy for ADCs might pose a strategy for increasing efficacy, diminish side-effects and slow down resistance development especially because single agent therapy has seldom been curative.

SUMMARY OF THE INVENTION

Several ATRis (Ataxia Telangiectasia and RAD3-related protein inhibitors), which inhibit DNA damage repair, are currently in clinical development. None of this has been approved yet.

During the research work that lead to the present invention, the inventors surprisingly found that the combination of a duocarmycin bearing ADC with an ATR inhibitor does not only show a combined efficacy, but a highly synergistic effect.

It was hypothesized by the present inventors that a combination of DNA-damage response inhibitors (DDRis) might pose an additional strategy to an improved cancer therapy based on a duocarmycin bearing ADC. Several different DDRi were selected and tested in in vitro and in vivo models. HCC-1954 and MDA-MB-468 cancer cells were treated with a combination of the selected DDRis and duocarmycin alone or attached to an antibody, and the antiproliferative effects of the combination treatment were compared to the effects of the single agents alone.

"Naked" duocarmycins as well as duocarmycin bearing ADCs were combined with several DDRi known in the art. The mode of actions of such DDRis were manyfold, e.g. decreasing Rad 51 expression, CHK1 inhibition, WEE1 kinase inhibition, O6-alkylguanine-DNA alkyltransferase inhibition, DN-PK inhibition Parp inhibition MTH1 inhibition, ATR inhibition, CHK1 inhibition, NEK1 inhibition, TOP2 inhibition, Her2 inhibition and others.

The experiments leading to the present invention surprisingly showed that exclusively inhibitors of the kinase ATR and inhibitors to its major downstream effector checkpoint kinase 1 (CHK1), which play a central role in the response to replication stress, enhanced the cytotoxic effects of the duocarmycin bearing ADC in a highly synergistic manner.

Several duocarmycin based ADCs showed strong synergistic effects in combination with different ATR inhibitors in vitro as well as in vivo. rag2 mice bearing a HER2-expressing NCI-N87 tumor were treated with HER2-targeting duocarmycin-ADC and two different ATR inhibitors. The ATR inhibitors monotreatment showed very mild tumor growth inhibition while the treatment with the ADC at concentrations below the maximum effective dose led to a partial tumor response. The combination treatment, however, resulted in very strong anti-tumor effects while being well tolerated. The present study demonstrates the superiority of combining the targeted delivery of duocarmycin to the tumor using an anti-HER2-duocarmycin ADC with systemic application of ATR inhibitors over the treatment with the drugs as single agents.

Since duocarmycins as such due to high toxicity do not seem to be promising candidate for human cancer therapy, the combination of an duocarmycin bearing ADC with an ATRi is highly promising. This might support endeavors of evaluating such combinations in a clinical setting.

Specific types of cancer to be treated according to the invention include, but are not limited to, cancer of the ovary, peritoneum, fallopian tube, lung, head and neck, colon, neuroendocrine system, urothelium, prostate, esophagus, bladder, stomach, mesenchyme, breast, pancreas, and histological subtypes thereof. In some embodiments, the cancer is selected from small-cell lung cancer (SCLC), non-small-cell lung cancer (NSCLC), squamous cell carcinoma of the head and neck (SCCHN), colorectal cancer (CRC), primary neuroendocrine tumors and sarcoma or PARPi-resistant recurrent cancer selected from ovarian, primary peritoneal, and fallopian tube cancer.

In some aspects, the ATR inhibitor is represented by one of the following formulae:

Compound 1

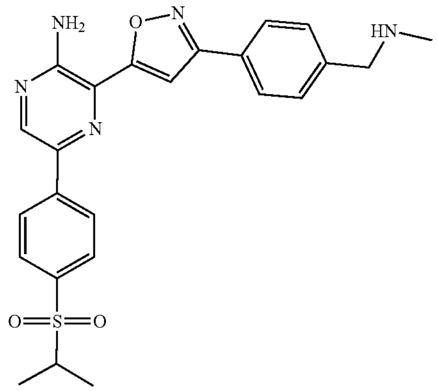

Compound 2

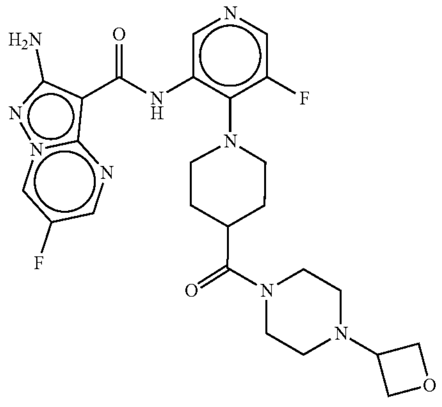

Compound 3

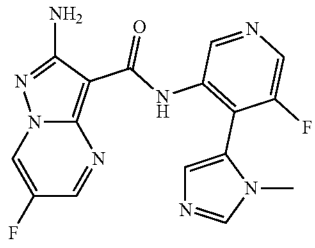

or a pharmaceutically acceptable salt thereof.

In further embodiments, the ADC bearing a DNA alkylating agent and the ATR inhibitor are used in combination with radiotherapy (RT), a further chemotherapy (CT), or chemoradiotherapy (CRT).

In a further aspect, the disclosure provides a method for advertising an ADC bearing a DNA alkylating agent in combination with an ATR inhibitor, comprising promoting, to a target audience, the use of the combination for treating a subject with a cancer.

Provided herein is also a pharmaceutical composition comprising an ADC bearing a DNA alkylating agent, an ATR inhibitor and at least a pharmaceutically acceptable excipient or adjuvant.

In a further aspect, the invention relates to a kit comprising an ADC bearing a DNA alkylating agent and a package insert comprising instructions for using the ADC bearing a DNA alkylating agent in combination with an ATR inhibitor to treat or delay progression of a cancer in a subject. Also provided is a kit comprising an ATR inhibitor and a package insert comprising instructions for using the ATR inhibitor in combination with an ADC bearing a DNA alkylating agent to treat or delay progression of a cancer in a subject.

The kits of the preceding paragraphs may further indicate instructions for radiotherapy, additional chemotherapy or radiochemotherapy.

BRIEF DESCRIPTION OF THE FIGURES

FIG. 6: Chemical structures of the duocarmycin-variants DUBA (10), DDM (38) and DSA (13) studied in the ADC format. The drugs are displayed in the seco-form.

DETAILED DESCRIPTION OF THE INVENTION

Definitions

Figure 1:
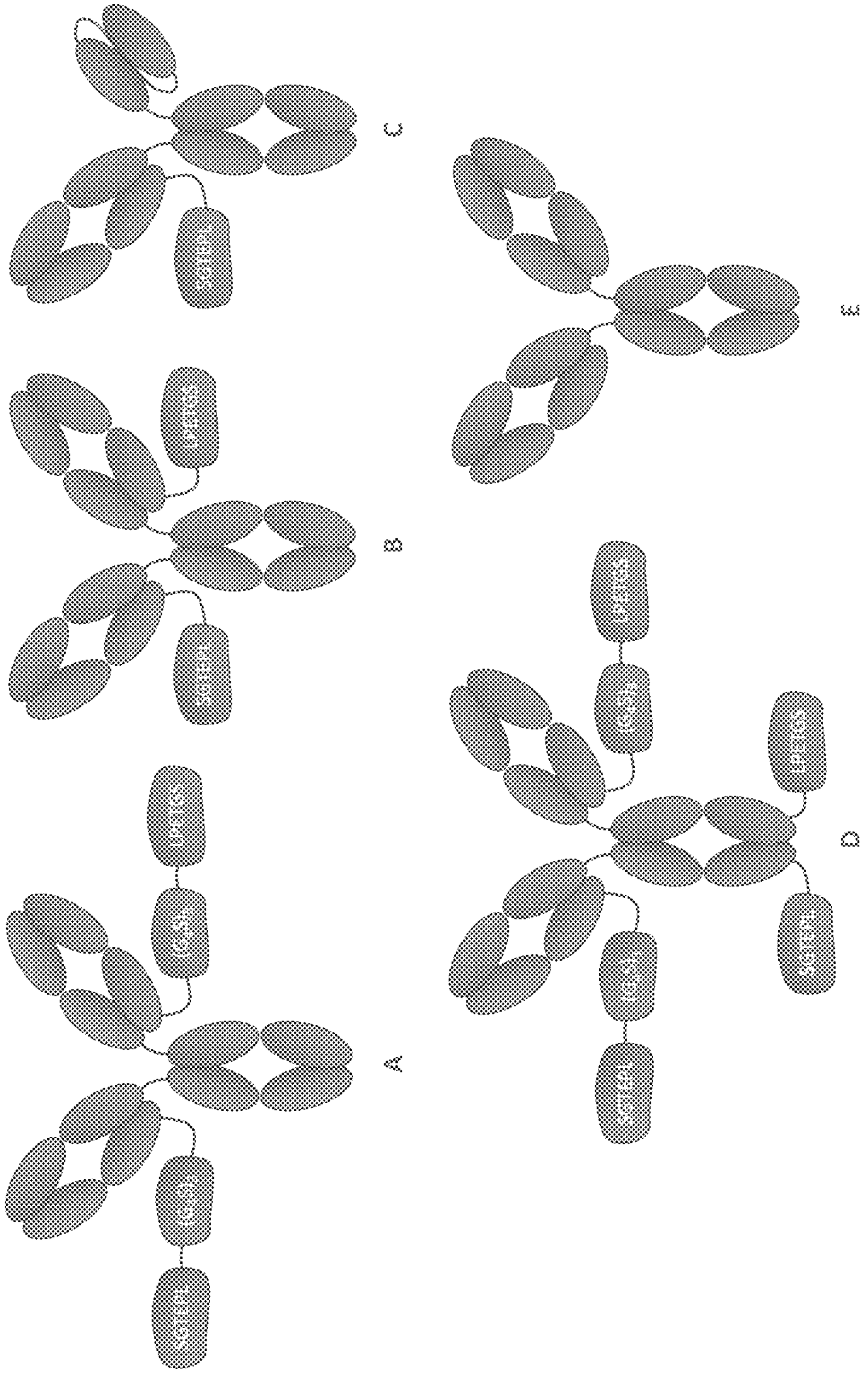
FIG. 1 shows A) LCs of antibody are elongated C-terminally by the motif $(G_4S)_3$LPETGS. B) LCs of antibody are elongated C-terminally by the motif LPETGS. C) SEED antibody carrying scFv on one chain, and a Fab on the other chain. The Fab is elongated C-terminally by a LPETGS sequence. D) Antibody carrying a total of four SrtA sites. A $(G_4S)_3$LPETGS SrtA recognition motif is fused C-terminally to the LCs, and a LPETGS sequence C-terminally to the HCs. E) Native mAb

"A", "an", and "the" include plural referents unless the context clearly dictates otherwise. Thus, for example, reference to an antibody refers to one or more antibodies or at least one antibody. As such, the terms "a" (or "an"), "one or more", and "at least one" are used interchangeably herein.

"About" when used to modify a numerically defined parameter (e.g., the dose of a compound, or the length of treatment time with a combination therapy described herein) means that the parameter may vary by as much as 10% below or above the stated numerical value for that parameter. For example, a dose of about 10 mg/kg may vary between 9 mg/kg and 11 mg/kg.

Antibody-drug conjugates or ADCs are well known in the art. Several techniques exist for linking the drug to the antibody. These are reviewed for example in Beck et al., Nature reviews, Volume 16, May 2017. Antibody-drug conjugates, also known as ADC or immunoconjugates, are targeted chemo-therapeutic molecules, combining the properties of both antibodies and cytotoxic drugs by targeting potent cytotoxic drugs to the antigen-expressing tumor cells, thereby enhancing their anti-tumor activity.

Successful antibody-drug conjugate development for a given target antigen depends on optimization of antibody selection, linker stability, cytotoxic drug potency and mode of linker-drug conjugation to the antibody. More particularly, selective antibody-drug conjugates are characterized by at least one or more of the following:

(i) an antibody-drug conjugate formation method wherein the antibody retains sufficient specificity to target antigens and wherein the drug efficacy is maintained; (ii) antibody-drug conjugate stability sufficient to limit drug release in the blood and concomitant damage to non-targeted cells; (iii) sufficient cell membrane transport efficiency (endocytosis) to achieve a therapeutic intracellular antibody-drug conjugate concentration; (iv) sufficient intracellular drug release from the antibody-drug conjugate sufficient to achieve a therapeutic drug concentration; and (v) drug cytotoxicity in nanomolar or sub-nanomolar amounts.

Antibody-drug conjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off target toxicity (Carter, P. J. and Senter P. D. (2008) *The Cancer Jour.* 14(3):154-169; Chari, R V. (2008) *Acc. Chem. Res.* 41:98-107.

The ADCs of the present invention are directed to tumor-associated antigens or cell-surface receptors, in some embodiments selected from the group consisting of the following proteins (1)-(87).

(1) BMPR1B (bone morphogenetic protein receptor-type 1B, Genbank accession no. NM_001203)
(2) E16 (LAT1, SLC7A5, Genbank accession no. NM_003486)
(3) STEAP1 (six transmembrane epithelial antigen of prostate, Genbank accession no. NM_OI2449)
(4) 0772P (CA125, MUC16, Genbank accession no. AF361486)
(5) MPF (MPF, MSLN, SMR, megakaryocyte potentiating factor, mesothelin, Genbank accession no. NM_005823)
(6) Napi2b (Napi3b, NAPI-3B, NPTIIb, SLC34A2, solute carrier family 34 (sodium phosphate), member 2, type II sodium-dependent phosphate transporter 3b, Genbank accession no. NM_006424)
(7) Serna Sb (FLJ10372, KIAA144S, Mm.4201S, SEMASB, SEMAG, Semaphorin Sb Hlog, sema domain, seven thrombospondin repeats (type I and type I-like), transmembrane 5 domain (TM) and short cytoplasmic domain, (semaphorin) SB, Genbank accession no. AB040878)
(8) PSCA hlg (27000SOC12Rik, CS30008016Rik, RIKEN cDNA 27000SOC12, RIKEN cDNA 27000SOC 12 gene, Genbank accession no. AY3S8628);
(9) ETBR (Endothelin type B receptor, Genbank accession no. AY27S463);
(10) MSG783 (RNF124, hypothetical protein FLJ20315, Genbank accession no. NM_017763);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138)
(12) TrpM4 (BR22450, FLJ20041, TRPM4, TRPM4B, transient receptor potential cation channel, subfamily M, member 4, Genbank accession no. NM_017636)
(13) CRIPTO (CR, CR1, CRGF, CRIPTO, TDGF1, teratocarcinoma-derived growth factor, Genbank accession no. NP 003203 or NM_003212)
(14) CD21 (CR2 (Complement receptor 2) or C3DR (C3d/Epstein Barr virus receptor) or Hs.73792 Genbank accession no. M26004)
(15) CD79b (CD79B, CD79~, IGb (immunoglobulin-associated beta), B29, Genbank accession no. NM_000626 or 11038674)
(16) FcRH2 (IFGP4, IRTA4, SPAP1A (SH2 domain containing phosphatase anchor protein Ia), SPAP1B, SPAP1C, Genbank accession no. NM_030764, AY358130)
(17) HER2 (ErbB2, Genbank accession no. MI 1730)
(18) NCA (CEACAM6, Genbank accession no. M18728);
(19) MDP (DPEP1, Genbank accession no. BC017023)
(20) IL20Ra (IL20Ra, ZCYTOR7, Genbank accession no. AF 84971);
(21) Brevican (BCAN, BEHAB, Genbank accession no. AF229053)
(22) EphB2R (DRT, ERK, Hek5, EPHT3, Tyro5, Genbank accession no. NM_004442)
(23) ASLG659 (B7h, Genbank accession no. AX092328)
(24) PSCA (Prostate stem cell antigen precursor, Genbank accession no. AJ297436)
(25) GEDA (Genbank accession No. AY260763);
(26) BAFF-R (B cell-activating factor receptor, BLyS receptor 3, BR3, Genbank accession no. AF 16456); BAFF receptor/pid=NP 443177.1—
(27) CD22 (B-cell receptor CD22-B isoform, BL-CAM, Lyb-8, Lyb8, SIGLEC-2, FLJ22814, Genbank accession No. AK026467);
(28) CD79a (CD79A, CD79a, immunoglobulin-associated alpha, a B cell-specific protein that covalently interacts with Ig beta (CD79B) and forms a complex on the surface with IgM molecules, transduces a signal involved in B-cell differentiation), Genbank accession No. NP_001774.10
(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pl: 8.54 MW: 41959 TM: 7 [P] Gene Chromosome: I Iq23.3, Genbank accession No. NP_001707.1)
(30) HLA-DOB (Beta subunit of MHC class II molecule (la antigen) that binds peptides and presents them to CD4+ T lymphocytes); 273 aa, pl: 6.56 MW: 30820 TM: 1 [P]Gene Chromosome: 6p21.3, Genbank accession No. NP 002111.1)
(31) P2X5 (Genbank accession No. NP 002552.2)
(32) CD72 (B-cell differentiation antigen CD72, Lyb-2) Genbank accession No. NP 001773.1)
(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, Genbank accession No.NP 005573.1)

(34) FcRHI (Genbank accession No. NP_443170.1)

(35) FCRH5 Genbank accession No.Human:AF343662, AF343663, AF343664, AF343665, AF369794, AF397453, AK.090423, AK.090475, AL834187, AY358085; Mouse:AK.089756, AY158090, AY506558; NP 112571.1

(36) TENB2 (TMEFF2, tomoregulin, TPEF, HPPI, TR, putative transmembrane proteoglycan, related to the EGF/heregulin family of growth factors and follistatin), NCBI Accession: AAD55776, AAF91397, AAG49451, NCBI RefSeq: NP 057276; NCBI Gene: 23671; OMIM: 605734; SwissProt Q9UIK5; Genbank accession No. AFI 79274; AY358907, CAF85723, CQ782436

(37) PMELI 7 (silver homolog; SIL V; D12S53E; PMELI 7; SI; SIL); ME20; gp100) BC001414; BT007202; M32295; M77348; NM_006928;

(38) TMEFFI; H7365; C9orf2; C90RF2; U19878; X83961; NM_080655; NM_003692;

(39) GDNF-Ral (GDNF family receptor alpha I; GFRAI; GDNFR; GDNFRA; RETLI; TRNRI; RETIL; GDNFR-alphal; GFR-ALPHA-1); U95847; BC014962; NM_145793, NM_005264;

(40) Ly6E (lymphocyte antigen 6 complex, locus E, Ly67, RIG-E, SCA-2, TSA-1); 15 NP 002337.1; NM_002346.2;

(41) TMEM46 (shisa hornolog 2 (*Xenopus laevis*); SHISA2); NP 001007539.1; NM_001007538.

(42) Ly6G6D (lymphocyte antigen 6 complex, locus G6D; Ly6-D, MEGTI); NP 067079.2; NM_021246.2;

(43) LGR5 NP 003658.1; NM_003667.2;

(44) RET (ret proto-oncogene; MEN2A; HSCRI; MEN2B; MTCl; PTC; CDHF12; Hs.168114; RET5 I; RET-ELEI); NP_066124.1; NM_020975 0.4;

(45) LY6K (lymphocyte antigen 6 complex, locus K; LY6K; HSJ001348; FLJ35226); NP_059997.3; NM_017527.3;

(46) GPR19 (G protein-coupled receptor 19; Mm.4787); NP 006134.1; NM_006143.2;

(47) GPR54 (KISS1 receptor; KISS1R; GPR54; HOT7TI 75; AXOR12); NP 115940.2; 10 NM_032551.4;

(48) ASPHDI (aspartate beta-hydroxylase domain containing 1; LOC253982); NP 859069.2; NM_181718.3;

(49) Tyrosinase (TYR; OCAIA; OCAIA; tyrosinase; SHEP3); NP 000363.1; NM_000372.4;

(50) TMEMI 18 (ring finger protein, transmembrane 2; RNFT2; FLJ14627); NP Ishikawa, N. et al (2007) Cancer Res. 67 (24):11601-11611; de Nooij-van Dalen, A. G. et al. 1: NM_001109903.1;

(51) GPRI 72A (G protein-coupled receptor 172A; GPCR41; FLJ11856; D15Ertd747e); NP 078807.1; NM_024531.3

(52) CD33

(53) CLL-1 (CLEC12A, MICL, and DCAL2),

(54) CEACAM-5

(55) MUC-1

(56) EGFR

(57) c-Met

(58) avb6

(59) ROR1

(60) Folate R1

(61) HER2

(62) 5T4

(63) Trop-2

(64) gpNMB

(65) CanAg

(66) Cadherin-3

(67) Cadherin-6

(68) CD44v6

(69) CD138

(70) CD174

(71) EpCAM

(72) cKit

(73) EphA2

(74) EphA4

(75) FGFR2

(76) FGFR3

(77) GCC

(78) IGFR1

(79) Mesothelin

(80) NaPi2B

(81) PSMA

(82) TIM1

(83) PTK7

(84) TF (tissue factor)

(85) IL13RA2

(86) GRP78

(87) gammaGT

In one embodiment the ADCs of the present invention may carry a duocarmycin as a DNA-alkylating agent. Examples of duocarmycins usable in the present invention are set out in table 4 and 5 as well as FIG. 23.

A further class of DNA alkylating agents which have been used in ADCs are indolinobenzodiazepine e.g. Miller et al., Mol Cancer Ther, Aug. 1, 2016 (15) (8) 1870-1878.

Further duocarmycins usable in the present invention are described for BMS-936561 and SYD985.

The duocarmycin in SYD985 is seco-DUBA (see FIG. 6, (10)).

In some embodiments, non-duocarmycin DNA-alkylating agents usable in the present invention are of the following formula (x)

(x)

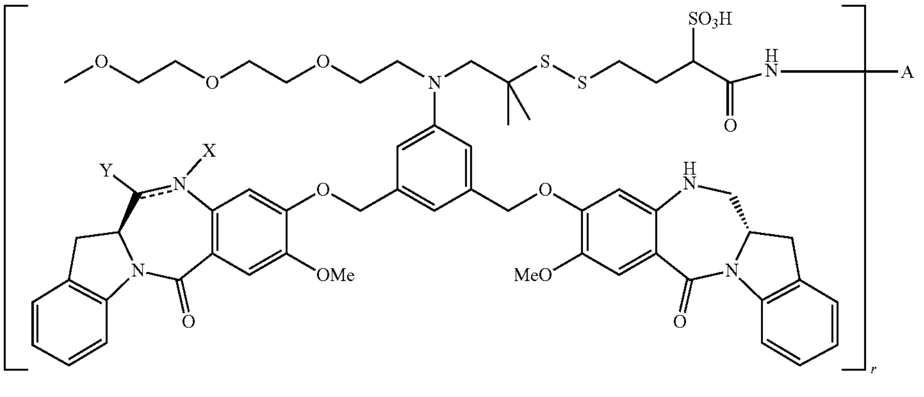

or a pharmaceutically acceptable salt thereof. The double line ═ between N and C represents either a single bond or a double bond, provided that when it is a double bond, X is absent and Y is hydrogen; and when it is a single bond, X is hydrogen and Y is —S03H. The term "A" is an antibody or antigen-binding fragment as defined below.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. E.g., a physician who instructs a patient to self-administer a drug or provides a patient with a prescription for a drug is administering the drug to the patient.

"Antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also, unless otherwise specified, any antigen-binding fragment or antibody fragment thereof that competes with the intact antibody for specific binding, fusion proteins comprising an antigen-binding portion (e.g., antibody-drug conjugates), any other modified configuration of the immunoglobulin molecule that comprises an antigen recognition site, antibody compositions with poly-epitopic specificity, and multi-specific antibodies (e.g., bispecific antibodies).

"Antigen-binding fragment" of an antibody or "antibody fragment" comprises a portion of an intact antibody, which is still capable of antigen binding and/or the variable region of the intact antibody. Antigen-binding fragments include, for example, Fab, Fab', F(ab')2, Fd, and Fv fragments, domain antibodies (dAbs, e.g., shark and camelid antibodies), fragments including complementarity determining regions (CDRs), single chain variable fragment antibodies (scFv), single-chain antibody molecules, multi-specific antibodies formed from antibody fragments, maxibodies, minibodies, intrabodies, diabodies, triabodies, tetrabodies, v-NAR and bis-scFv, linear antibodies (see e.g., U.S. Pat. No. 5,641,870, Example 2; Zapata et al. (1995) Protein Eng. 8HO: 1057), and polypeptides that contain at least a portion of an immunoglobulin that is sufficient to confer specific antigen binding to the polypeptide. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment, which roughly corresponds to two disulfide linked Fab fragments having different antigen-binding activity and is still capable of cross-linking antigen. Fab' fragments differ from Fab fragments by having a few additional residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments were originally produced as pairs of Fab' fragments which have hinge cysteines between them. Other chemical couplings of antibody fragments are also known.

"ATR inhibitor" or "ATRi" refers to an inhibitor of the ATR kinase pathway, which mediates the DNA damage response. Preferably, the ATR inhibitor is a molecule that inhibits the enzymatic activity of the ATR kinase. Examples of ATR inhibitors that are useful in the treatment method, medicaments and uses of the present invention include any of the Compounds 1 to 5, or a pharmaceutically acceptable salt thereof. Further ATR inhibitors are described in WO 2013/049726, WO 2013/152298, WO 2013/049859, US-2013-0089625, US-2013-0115312, US-2014-0107093, US-2013-0096139, WO 2011/143426, US-2013-0095193, WO 2014/055756, WO 2011/143419, WO 2011/143422, WO 2011/143425, US-2013-0115311, US-2013-0115312, US-2013-0115313, US-2013-0115314, WO 2011/163527, WO 2012/178123, WO 2012/178124, WO 2012/178125, US-2014-0113005, WO2013/049726, WO 2013/071085, WO 2010/071837, WO 2014/089379, WO 2014/143242, WO 2014/143241, WO 2015/084384, WO 2014/143240, WO 2015/187451, WO 2015/085132, WO 2014/062604, WO 2014/143240, WO 2013/071094, WO 2013/071093, WO 2013/071090, WO 2013/071088, WO 2013/049859, WO 2013/049719, WO 2013/049720, WO 2013/049722, WO 2012/138,938, WO 2011/163527, WO 2011/143,423, WO 2011/143,426, WO 2011/143,399, and/or WO 2010/054398, all of which are incorporated herein by way of reference in their entirety.

"Biomarker" generally refers to biological molecules, and quantitative and qualitative measurements of the same, that are indicative of a disease state. "Prognostic biomarkers" correlate with disease outcome, independent of therapy. For example, tumor hypoxia is a negative prognostic marker—the higher the tumor hypoxia, the higher the likelihood that the outcome of the disease will be negative. "Predictive biomarkers" indicate whether a patient is likely to respond positively to a particular therapy. E.g., HER2 profiling is commonly used in breast cancer patients to determine if those patients are likely to respond to Herceptin (trastuzumab, Genentech). "Response biomarkers" provide a measure of the response to a therapy and so provide an indication of whether a therapy is working. For example, decreasing levels of prostate-specific antigen generally indicate that anti-cancer therapy for a prostate cancer patient is working. When a marker is used as a basis for identifying or selecting a patient for a treatment described herein, the marker can be measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one in the art, measurement of a biomarker in a clinical setting is a clear indication that this parameter was used as a basis for initiating, continuing, adjusting and/or ceasing administration of the treatments described herein.

"Cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, Hodgkin's lymphoma, non-Hodgkin's lymphoma, acute myeloid leukemia, multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, urothelial cancer and head and neck cancer.

"Chemotherapy" is a therapy involving a chemotherapeutic agent, which is a chemical compound useful in the treatment of cancer. Examples of chemotherapeutic agents include alkylating agents such as thiotepa and cyclophosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide, and trimethylolomelamine; acetogenins (especially bullatacin and bullatacinone); delta-9-tetrahydrocannabinol (dronabinol); beta-lapachone; lapachol; colchicines; betulinic acid; bryostatin; pemetrexed; callystatin; podophyllotoxin; podophyllinic acid; teniposide; cryptophycins (particularly, cryptophycin 1 and cryptophycin 8); dolastatin; eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas such as carmustine, chlorozotocin, fotemustine, lomustine, nimustine, and ranimnustine; dynemicin including dynemicin A; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, doxorubicin HCl liposome injection, and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites such as methotrexate, gemcitabine, tegafur, capecitabine, an epothilone, and 5-fluorouracil (5-FU); folic acid analogues such as denopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, and trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially, T-2 toxin, verracurin A, roridin A, and anguidine); urethan; vindesine; dacarbazine; mannomustine; mitobronitol; mitolactol; pipobroman; gacytosine; arabinoside ("Ara-C"); thiotepa; taxoids, e.g., paclitaxel, albumin-engineered nanoparticle formulation of paclitaxel, and doxetaxel; chloranbucil; 6-thioguanine; mercaptopurine; methotrexate; platinum analogs such as cisplatin and carboplatin; vinblastine; platinum; ifosfamide; mitoxantrone; vincristine; oxaliplatin; leucovovin; vinorelbine; novantrone; edatrexate; daunomycin; aminopterin; ibandronate; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine and prednisolone, or FOLFOX, an abbreviation for a treatment regimen with oxaliplatin combined with 5-FU and leucovovin.

"Clinical outcome", "clinical parameter", "clinical response", or "clinical endpoint" refers to any clinical observation or measurement relating to a patient's reaction to a therapy. Non-limiting examples of clinical outcomes include tumor response (TR), overall survival (OS), progression free survival (PFS), disease free survival, time to tumor recurrence (TTR), time to tumor progression (TTP), relative risk (RR), toxicity, or side effect.

"Complete response" or "complete remission" refers to the disappearance of all signs of cancer in response to treatment. This does not always mean the cancer has been cured.

"Comprising", as used herein, is intended to mean that the compositions and methods include the recited elements, but not excluding others. "Consisting essentially of", when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

"Dose" and "dosage" refer to a specific amount of active or therapeutic agents for administration. Such amounts are included in a "dosage form," which refers to physically discrete units suitable as unitary dosages for human subjects and other mammals, each unit containing a predetermined quantity of active agent calculated to produce the desired onset, tolerability, and therapeutic effects, in association with one or more suitable pharmaceutical excipients such as carriers.

"Fc" is a fragment comprising the carboxy-terminal portions of both H chains held together by disulfides. The effector functions of antibodies are determined by sequences in the Fc region, the region which is also recognized by Fc receptors (FcR) found on certain types of cells.

"Functional fragments" of the antibodies of the invention comprise a portion of an intact antibody, generally including the antigen-binding or variable region of the intact antibody or the Fc region of an antibody which retains or has modified FcR binding capability. Examples of functional antibody fragments include linear antibodies, single-chain antibody molecules, and multi-specific antibodies formed from antibody fragments.

"Fv" is the minimum antibody fragment, which contains a complete antigen-recognition and antigen-binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen-binding specificity to the antibody. However, even a single variable domain (or half of an Fv comprising only three HVRs specific for an antigen) has the ability to recognize and bind antigen, although at a lower affinity than the entire binding site.

"Human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries (see e.g., Hoogenboom and Winter (1991), JMB 227: 381; Marks et al. (1991) JMB 222: 581). Also available for the preparation of human monoclonal antibodies are methods described in Cole et al. (1985) Monoclonal Antibodies and Cancer Therapy, Alan R. Liss, page 77; Boerner et al. (1991), J. Immunol 147(l): 86; van Dijk and van de Winkel (2001) Curr. Opin. Pharmacol 5: 368). Human antibodies can be prepared by administering the antigen to a transgenic animal that has been modified to produce such antibodies in response to antigenic challenge but whose endogenous loci have been disabled, e.g., immunized xenomice (see e.g., U.S. Pat. Nos. 6,075,181; and 6,150,584 regarding XENOMOUSE technology). See also, for example, Li et al. (2006) PNAS USA, 103: 3557, regarding human antibodies generated via a human B-cell hybridoma technology.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit, or non-human primate having the desired specificity, affinity and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and no more than 3 in the L chain. The humanized antibody optionally will also comprise at least a portion of an immunoglobulin constant region (Fc), typically that of a human immunoglobulin. For further details, see e.g., Jones et al. (1986) Nature 321: 522; Riechmann et al. (1988), Nature 332: 323; Presta (1992) Curr. Op. Struct. Biol. 2: 593; Vaswani and Hamilton (1998), Ann. Allergy, Asthma & Immunol. 1: 105; Harris (1995) Biochem. Soc. Transactions 23: 1035; Hurle and Gross (1994) Curr. Op. Biotech. 5: 428; and U.S. Pat. Nos. 6,982,321 and 7,087,409.

"Immunoglobulin" (Ig) is used interchangeably with "antibody" herein. The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intra-chain disulfide bridges. Each H chain has, at the N-terminus, a variable domain (VH) followed by three constant domains (CH) for each of the α and γ chains and four CH domains for μ and ε isotypes. Each L chain has at the N-terminus, a variable domain (VL) followed by a constant domain at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see e.g., Basic and Clinical Immunology, 8th Edition, Sties et al. (eds.), Appleton & Lange, Norwalk, CT, 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1, and IgK1.

"Infusion" or "infusing" refers to the introduction of a drug-containing solution into the body through a vein for therapeutic purposes. Generally, this is achieved via an intravenous (IV) bag.

"In combination with" or "in conjunction with" refers to the administration of one compound in addition to one or more other compound. As such, "in combination with" or "in conjunction with" refers to the administration of one compound in addition to the administration of one or more other compound in any order. For instance, the one compound may be administered before, during, or after administration of the one or more other compound to the individual. As used herein, the term "in combination" with regard to the administration of the combination comprising the ADC bearing an DNA alkylating agent and an ATR inhibitor means that these compounds are administered to the patient in any order. For instance, the compounds may be administered simultaneously or sequentially. Also, two compounds may be administered simultaneously, followed by the sequential administration of the third compound, in case there is additional chemotherapy. Also, the compounds may be administered as a single or separate compositions, formulations or unit dosage forms. Also, two compounds may be administered as a single composition, formulation or unit dosage form, whereas the third compound is administered as a separate composition, formulation or unit dosage form. It will be appreciated that the ADC bearing an DNA alkylating agent, the ATR inhibitor and the potential additional chemotherapeutic agent or radiotherapy or radiochemotherapy are administered on the same day or on different days and in any order as according to an appropriate dosing protocol.

"Metastatic" cancer refers to cancer which has spread from one part of the body (e.g., the lung) to another part of the body.

"Monoclonal antibody", as used herein, refers to an antibody obtained from a population of substantially homogeneous antibodies, i.e., the individual antibodies comprising the population are identical except for possible naturally occurring mutations and/or post-translation modifications (e.g., isomerizations and amidations) that may be present in minor amounts. Monoclonal antibodies are highly specific, being directed against a single antigenic site. In contrast to polyclonal antibody preparations, which typically include different antibodies directed against different determinants (epitopes), each monoclonal antibody is directed against a single determinant on the antigen. In addition to their specificity, the monoclonal antibodies are advantageous in that they are synthesized by the hybridoma culture and uncontaminated by other immunoglobulins. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by a variety of techniques, including, for example, the hybridoma method (e.g., Kohler and Milstein (1975) Nature 256: 495; Hongo et al. (1995) Hybridoma 14 (3): 253; Harlow et al. (1988) Antibodies: A Laboratory Manual (Cold Spring Harbor Laboratory Press, 2nd ed.; Hammerling et al. (1981) In: Monoclonal Antibodies and T-Cell Hybridomas 563 (Elsevier; N.Y.), recombinant DNA methods (see e.g., U.S. Pat. No. 4,816,567), phage-display technologies (see e.g., Clackson et al. (1991) Nature 352: 624; Marks et al. (1992) JMB 222: 581; Sidhu et al. (2004) JMB 338(2): 299; Lee et al. (2004) JMB 340(5): 1073; Fellouse (2004) PNAS USA 101(34): 12467; and Lee et al. (2004) J. Immunol. Methods 284(1-2): 119), and technologies for producing human or human-like antibodies in animals that have parts or all of the human immunoglobulin loci or genes encoding human immunoglobulin sequences (see e.g., WO 1998/24893; WO 1996/34096; WO 1996/33735; WO 1991/10741; Jakobovits et al. (1993) PNAS USA 90: 2551; Jakobovits et al. (1993) Nature 362: 255; Bruggemann et al. (1993) Year in Immunol. 7: 33; U.S. Pat. Nos. 5,545,807; 5,545,806; 5,569,825; 5,625,126; 5,633,425; and U.S. Pat. No. 5,661,016; Marks et al. (1992) Bio/Technology 10: 779; Lonberg et al. (1994) Nature 368: 856; Morrison (1994) Nature 368: 812; Fishwild et al. (1996) Nature Biotechnol. 14: 845; Neuberger (1996), Nature Biotechnol. 14: 826; and Lonberg and Huszar (1995), Intern. Rev. Immunol. 13: 65-93). The monoclonal antibodies herein specifically include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (see e.g., U.S. Pat. No. 4,816,567; Morrison et al. (1984) PNAS USA, 81: 6851).

"Objective response" refers to a measurable response, including complete response (CR) or partial response (PR).

"Partial response" refers to a decrease in the size of one or more tumors or lesions, or in the extent of cancer in the body, in response to treatment.

"Patient" and "subject" are used interchangeably herein to refer to a mammal in need of treatment for a cancer. Generally, the patient is a human diagnosed or at risk for suffering from one or more symptoms of a cancer. In certain embodiments a "patient" or "subject" may refer to a non-human mammal, such as a non-human primate, a dog, cat, rabbit, pig, mouse, or rat, or animals used in screening, characterizing, and evaluating drugs and therapies.

"Pharmaceutically acceptable" indicates that the substance or composition must be chemically and/or toxicologically suitable for the treatment of mammals.

The term "pharmaceutically acceptable adjuvant" refers to any and all substances which enhance the body's immune response to an antigen. Non-limiting examples of pharmaceutically acceptable adjuvants are: Alum, Freund's Incomplete Adjuvant, MF59, synthetic analogs of dsRNA such as poly(I:C), bacterial LPS, bacterial flagellin, imidazolquinolines, oligodeoxynucleotides containing specific CpG motifs, fragments of bacterial cell walls such as muramyl dipeptide and Quil-A®.

As used herein, "pharmaceutically acceptable carrier" or "pharmaceutically acceptable diluent" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and, without limiting the scope of the present invention, include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone. Other pharmaceutically acceptable carriers, excipients, or stabilizers, such as those described in Remington's Pharmaceutical Sciences 16th edition, Osol, A. Ed. (1980) may also be included in a pharmaceutical composition described herein, provided that they do not adversely affect the desired characteristics of the pharmaceutical composition.

"Pharmaceutically acceptable salt" of a molecule refers to the salt form of the molecule. A pharmaceutically acceptable salt may involve the inclusion of another molecule, such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion. If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic, acid, an aromatic acid, such as benzoic acid or cinnamic acid, a sulfonic acid, such as p-toluenesulfonic acid or ethanesulfonic acid, or the like. If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

"Recurrent" cancer is one which has regrown, either at the initial site or at a distant site, after a response to initial therapy, such as surgery. A locally "recurrent" cancer is cancer that returns after treatment in the same place as a previously treated cancer.

"Reduction" of a symptom or symptoms (and grammatical equivalents of this phrase) refers to decreasing the severity or frequency of the symptom(s), or elimination of the symptom(s).

"Serum" refers to the clear liquid that can be separated from clotted blood. Serum differs from plasma, the liquid portion of normal unclotted blood containing the red and white cells and platelets. Serum is the component that is neither a blood cell (serum does not contain white or red blood cells) nor a clotting factor. It is the blood plasma not including the fibrinogens that help in the formation of blood clots. It is the clot that makes the difference between serum and plasma.

"Single-chain Fv", also abbreviated as "sFv" or "scFv", are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of the sFv, see e.g., Pluckthun (1994), In: The Pharmacology of Monoclonal Antibodies, vol. 113, Rosenburg and Moore (eds.), Springer-Verlag, New York, pp. 269.

"Sustained response" means a sustained therapeutic effect after cessation of treatment with a therapeutic agent, or a combination therapy described herein. In some embodiments, the sustained response has a duration that is at least the same as the treatment duration, or at least 1.5, 2.0, 2.5 or 3 times longer than the treatment duration.

"Systemic" treatment is a treatment, in which the drug substance travels through the bloodstream, reaching and affecting cells all over the body.

"Therapeutically effective amount" of an ADC bearing a DNA alkylating agent or an ATR inhibitor, in each case of the invention, refers to an amount effective, at dosages and for periods of time necessary, that, when administered to a patient with a cancer, will have the intended therapeutic effect, e.g., alleviation, amelioration, palliation, or elimination of one or more manifestations of the cancer in the patient, or any other clinical result in the course of treating a cancer patient. A therapeutic effect does not necessarily occur by administration of one dose and may occur only after administration of a series of doses. Thus, a therapeutically effective amount may be administered in one or more administrations. Such therapeutically effective amount may vary according to factors such as the disease state, age, sex, and weight of the individual, and the ability of the ADC bearing an alkylating agent or the ATR inhibitor elicit a desired response in the individual. A therapeutically effective amount is also one in which any toxic or detrimental effects of the ADC bearing an alkylating agent or the ATR inhibitor are outweighed by the therapeutically beneficial effects.

"Treating" or "treatment of" a condition or patient refers to taking steps to obtain beneficial or desired results, including clinical results. For purposes of this invention, beneficial or desired clinical results include, but are not limited to, alleviation, amelioration of one or more symptoms of a cancer; diminishment of extent of disease; delay or slowing of disease progression; amelioration, palliation, or stabilization of the disease state; or other beneficial results. It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors.

"Unit dosage form" as used herein refers to a physically discrete unit of therapeutic formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

"Variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al. (1991) Sequences of Immunological Interest, 5th edition, National Institute of Health, Bethesda, MD). The constant domains are not involved directly in the binding of antibody to an antigen, but exhibit various effector functions, such as participation of the antibody in antibody-dependent cellular toxicity.

"Variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Abbreviations

Some abbreviations used in the description include:

ATR: Ataxia Telangiectasia and RAD3-related protein
BID: Twice daily
CDR: Complementarity determining region
CRC: Colorectal cancer
CRT: Chemoradiotherapy
CT: Chemotherapy
DNA: Deoxyribonucleic acid
Ig: Immunoglobulin
IHC: Immunohistochemistry
IV: Intravenous
mCRC: Metastatic colorectal cancer
MSI-H: Microsatellite status instable high
MSI-L: Microsatellite status instable low
MSS: Microsatellite status stable
NK: Natural killers
NSCLC: Non-small-cell lung cancer
OS: Overall survival
PFS: Progression free survival
QD: Once daily
QID: Four times a day
Q2W: Every two weeks
Q3W: Every three weeks
RNA: Ribonucleic acid
RR: Relative risk
RT: Radiotherapy
SCCHN: Squamous cell carcinoma of the head and neck
SCLC: Small-cell lung cancer
SoC: Standard of care
TID: Three times a day
TR: Tumor response
TTP: Time to tumor progression
TTR: Time to tumor recurrence Duocarmycins, first isolated from a culture broth of *Streptomyces* species, are members of a family of antitumor antibiotics that include duocarmycin A, duocarmycin SA, and CC-1065. Duocarmycins bind to the minor groove of DNA and subsequently cause irreversible alkylation of DNA. This disrupts the nucleic acid architecture, which eventually leads to tumor cell death.

Duocarmycins are a class of natural compounds originally isolated from *Streptomyces*. These highly potent molecules have a common molecular build-up, consisting of a DNA-alkylating unit and a DNA-binding unit as illustrated by the duocarmycin derivative DUBA (11). After binding the minor groove of AT-rich regions of the DNA double strand, an addition of N3 of adenine to the activated cyclopropane ring of DUBA occurs, leading to the alkylation of the DNA. Although duocarmycins comprise the reactive cyclopropane ring, they are considerably stable in aqueous media. However, duocarmycins exhibit remarkable alkylation efficiencies and rates in the presence of DNA. Complexes of Duocarmycin SA (DSA, 13) and DNA were studied using nuclear magnetic resonance (NMR) spectroscopy to elucidate this phenomenon. The two subunits of duocarmycins are coplanar in the absence of a ligand. Upon binding in the minor groove of DNA, hydrophobic contacts are maximized, leading to a conformational change of DSA. The two subunits are twisted with respect to each other, activating the molecule for alkylation.

A duocarmycin-based ADC currently in clinical development by the Dutch pharmaceutical company Synthon is SYD985. This ADC consists of the duocarmycin prodrug seco-DUBA which is connected via a cathepsin B-cleavable dipeptide linker to the anti-HER2 antibody trastuzumab.

WO2015/104373 discloses the use of duocarmycin bearing ADCs for the treatment of endometrial cancer.

WO 2011/133039 discloses a series of analogues of the DNA-alkylating agent CC-1065 and HER2-targeting ADCs thereof. In Example 15, a number of trastuzumab-duocarmycin conjugates were tested against N87 (i.e., HER2 IHC (immunohistochemistry) 3+ gastric tumor) xenografts in nude mice. The results are shown in FIGS. 4A, 4B and 4C of WO 2011/133039. After treatment with a single dose of 12 mg/kg i.v., all six ADCs reduced the tumor volume and improved survival compared to the antibody trastuzumab itself and control vehicle, without affecting body weight.

WO 2015/104385 discloses duocarmycin-containing ADCs for use in the treatment of human solid tumors and haematological malignancies expressing HER2.

The duocarmycins and derivatives thereof described in the art can be used for the purposes of the present invention.

The present invention arose in part from the discovery of a combination benefit for a DNA-alkylating ADC and an ATR inhibitor. Surprisingly, the combination of the present invention was shown to be superior to the combined treatment only. The inventors have shown that the potentiating effect of the combination is synergistic in cell culture and in vivo models.

Thus, in one aspect, the present invention provides a DNA-alkylating ADC and an ATR inhibitor for use in a method for treating a cancer in a subject in need thereof, comprising administering to the subject the DNA-alkylating ADC and the ATR inhibitor. Similarly, the present invention provides the use of the combination in a method for treating a cancer in a subject in need thereof, comprising administering to the subject the DNA-alkylating ADC and the ATR inhibitor. Similarly, the present invention provides the use of the DNA-alkylating ADC and an ATR inhibitor for the manufacture of a medicament for the treatment of cancer in a subject in need thereof, comprising administering to the subject the DNA-alkylating ADC and the ATR inhibitor.

It shall be understood that in all embodiments of the invention a therapeutically effective amount of the DNA-alkylating ADC and the ATR inhibitor is applied.

In some aspects, the ATR inhibitor is a compound represented by Formula A-I:

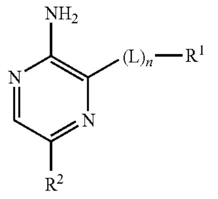

A-I or a pharmaceutically acceptable salt thereof, wherein:

$R^1$ is a 5-6 membered monocyclic aryl or heteroaryl ring having 0-4 heteroatoms independently selected from the group consisting of nitrogen, oxygen, and sulfur, wherein said monocyclic aryl or heteroaryl ring is optionally fused to another ring to form an 8-10 membered bicyclic aryl or heteroaryl ring having 0-6 heteroatoms independently selected from the group consisting of nitrogen, oxygen, and sulfur; each $R^1$ is optionally substituted with 1-5 $J^1$ groups;

$R^2$ is a 5-6 membered monocyclic aryl or heteroaryl ring having 0-3 heteroatoms independently selected from the group consisting of nitrogen, oxygen, and sulfur, wherein said monocyclic aryl or heteroaryl ring is optionally fused to another ring to form an 8-10 membered bicyclic aryl or heteroaryl ring having 0-4 heteroatoms independently selected from the group consisting of nitrogen, oxygen, and sulfur; each $R^2$ is optionally substituted with 1-5 $J^2$ groups;

L is —C(O)NH— or —C(O)N($C_{1-6}$alkyl)-;

n is 0 or 1;

each $J^1$ and $J^2$ is independently halo, —CN, —$NO_2$, —$V^1$—R, or —$(V^2)_m$-Q;

$V^1$ is a $C_{1-10}$aliphatic chain, wherein 0-3 methylene units are optionally and independently replaced with O, NR", S, C(O), S(O), or $S(O)_2$; $V^1$ is optionally substituted with 1-6 occurrences of $J^{V1}$;

$V^2$ is a $C_{1-10}$aliphatic chain, wherein 0-3 methylene units are optionally and independently replaced with O, NR", S, C(O), S(O), or $S(O)_2$; $V^2$ is optionally substituted with 1-6 occurrences of $J^{V2}$;

m is 0 or 1;

Q is a 3-8 membered saturated or unsaturated monocyclic ring having 0-4 heteroatoms independently selected from the group consisting of nitrogen, oxygen, and sulfur, or a 9-10 membered saturated or unsaturated bicyclic ring having 0-6 heteroatoms independently selected from the group consisting of nitrogen, oxygen, and sulfur; each Q is optionally substituted with 0-5 $J^Q$;

each $J^{V1}$ or $J^{V2}$ is independently halogen, CN, $NH_2$, $NO_2$, $C_{1-4}$aliphatic, NH($C_{1-4}$aliphatic), N($C_{1-4}$aliphatic)$_2$, OH, O($C_{1-4}$aliphatic), $CO_2H$, $CO_2$($C_{1-4}$aliphatic), C(O)$NH_2$, C(O)NH($C_{1-4}$aliphatic), C(O)N($C_{1-4}$aliphatic)$_2$, NHCO($C_{1-4}$aliphatic), N($C_{1-4}$aliphatic)CO($C_{1-4}$aliphatic), $SO_2$($C_{1-4}$aliphatic), $NHSO_2$($C_{1-4}$aliphatic), or N($C_{1-4}$aliphatic)$SO_2$($C_{1-4}$aliphatic), wherein said $C_{1-4}$aliphatic is optionally substituted with halo;

R is H or $C_{1-6}$aliphatic, wherein said $C_{1-6}$aliphatic is optionally substituted with 1-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2H$, $CO_2$($C_{1-4}$aliphatic), CO($C_{1-4}$aliphatic), O(halo$C_{1-4}$aliphatic), or halo$C_{1-4}$aliphatic;

each $J^Q$ is independently halo, oxo, CN, $NO_2$, X—R, or —$(X)_p$-$Q^4$;

p is 0 or 1;

X is $C_{1-10}$aliphatic, wherein 1-3 methylene units of said $C_{1-6}$aliphatic are optionally replaced with —NR, —O—, —S—, C(O), $S(O)_2$, or S(O); wherein X is optionally and independently substituted with 1-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, CO($C_{1-4}$aliphatic), $CO_2H$, $CO_2$($C_{1-4}$aliphatic), C(O)$NH_2$, C(O)NH($C_{1-4}$aliphatic), C(O)N($C_{1-4}$aliphatic)$_2$, SO($C_{1-4}$aliphatic), $SO_2$($C_{1-4}$aliphatic), $SO_2$NH($C_{1-4}$aliphatic), $SO_2$N($C_{1-4}$aliphatic)$_2$, NHC(O)($C_{1-4}$aliphatic), N($C_{1-4}$aliphatic)C(O)($C_{1-4}$aliphatic), wherein said $C_{1-4}$aliphatic is optionally substituted with 1-3 occurrences of halo;

$Q^4$ is a 3-8 membered saturated or unsaturated monocyclic ring having 0-4 heteroatoms independently selected from the group consisting of nitrogen, oxygen, and sulfur, or a 8-10 membered saturated or unsaturated bicyclic ring having 0-6 heteroatoms independently selected from the group consisting of nitrogen, oxygen, and sulfur; each $Q^4$ is optionally substituted with 1-5 $J^{Q4}$;

$J^{Q4}$ is halo, CN, or $C_{1-4}$alkyl, wherein up to 2 methylene units are optionally replaced with O, NR*, S, C(O), S(O), or $S(O)_2$;

R is H or $C_{1-4}$alkyl, wherein said $C_{1-4}$alkyl is optionally substituted with 1-4 halo;

R" and R* are each independently H, $C_{1-4}$alkyl, or is absent; wherein said $C_{1-4}$alkyl is optionally substituted with 1-4 halo.

In some embodiments, L is —C(O)NH—; and $R^1$ and $R^2$ are phenyl.

In another embodiment, the ATR inhibitor is a compound represented by Formula A-1-a:

A-I-a

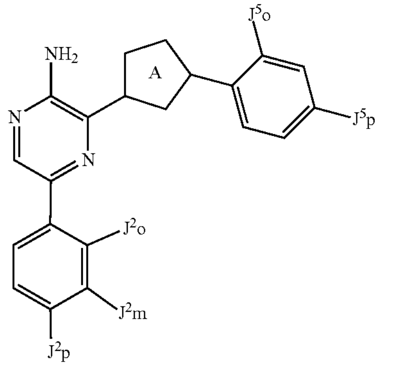

or a pharmaceutically salt thereof, wherein:

Ring A is

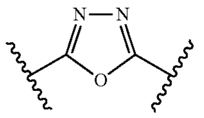

or

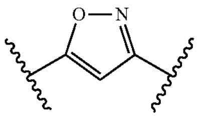

, $J^5$o is H, F, Cl, $C_{1-4}$aliphatic, O($C_{1-3}$aliphatic), or OH;

$J^5$p is

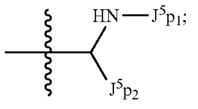

$J^5p_1$ is H, $C_{1-4}$aliphatic, oxetanyl, tetrahydrofuranyl, tetrahydropyranyl;

wherein $J^5p_1$ is optionally substituted with 1-2 occurrences of OH or halo;

$J^5p_2$ is H, methyl, ethyl, $CH_2F$, $CF_3$, or $CH_2OH$;

$J^2$o is H, CN, or $SO_2CH_3$;

$J^2$m is H, F, Cl, or methyl;

$J^2$p is —$SO_2$($C_{1-6}$alkyl), —$SO_2$($C_{3-6}$cycloalkyl), —$SO_2$ (4-6 membered heterocyclyl), —$SO_2$($C_{1-4}$alkyl)N ($C_{1-4}$alkyl)$_2$, or —$SO_2$($C_{1-4}$alkyl)-(4-6 membered heterocyclyl), wherein said heterocyclyl contains 1 heteroatom selected from the group consisting of oxygen, nitrogen, and sulfur; and wherein said $J^2$p is optionally substituted with 1-3 occurrences halo, OH, or O($C_{1-4}$alkyl).

In some embodiments, Ring A is

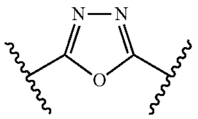

.

In other embodiments, Ring A is

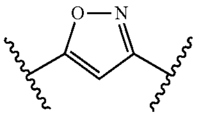

.

In some preferred embodiments, the ATR inhibitor is a compound represented by the following formula (Compound 1):

Compound 1

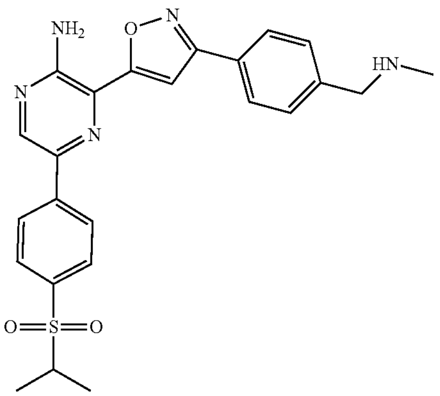

or a pharmaceutically acceptable salt thereof. Compound 1 is also referred to as 3-[3-(4-Methylaminomethyl-phenyl)-isoxazol-5-yl]-5-[4-(propane-2-sulfonyl)-phenyl]-pyrazin-2-ylamine.

In another aspect, the ATR inhibitor is represented by Formula A-II:

A-II

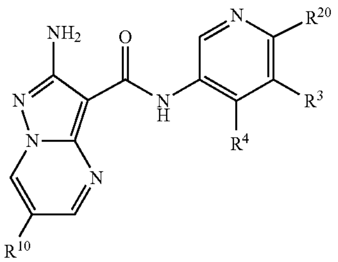

or a pharmaceutically salt or derivative thereof, wherein:

$R^{10}$ is selected from fluoro, chloro, or —$C(J^{10})_2CN$;

$J^{10}$ is independently H or $C_{1-2}$alkyl; or two occurrences of $J^{10}$, together with the carbon atom to which they are attached, form a 3-4 membered optionally substituted carbocyclic ring;

$R^{20}$ is H, halo, —CN, $NH_2$, a $C_{1-2}$alkyl optionally substituted with 0-3 occurrences of fluoro; or a $C_{1-3}$aliphatic chain, wherein up to two methylene units of the aliphatic chain are optionally replaced with —O—, —$NR^a$—, —C(O)—, or —$S(O)_z$;

$R^3$ is H, halo, $C_{1-4}$alkyl optionally substituted with 1-3 occurrences of halo, $C_{3-4}$cycloalkyl, —CN, or a $C_{1-3}$aliphatic chain, wherein up to two methylene units of the aliphatic chain are optionally replaced with —O—, —$NR^a$—, —C(O)—, or —$S(O)_z$;

$R^4$ is Q1 or a $C_{1-10}$aliphatic chain, wherein up to four methylene units of the aliphatic chain are optionally replaced with —O—, —$NR^a$—, —C(O)—, or —$S(O)_z$—;

each $R^4$ is optionally substituted with 0-5 occurrences of $J^{Q1}$; or $R^3$ and $R^4$, taken together with the atoms to which they are bound, form a 5-6 membered aromatic or non-aromatic ring having 0-2 heteroatoms selected from the group consisting of oxygen, nitrogen, and sulfur; the ring formed by $R^3$ and $R^4$ is optionally substituted with 0-3 occurrences of $J^Z$;

$Q^1$ is a 3-7 membered fully saturated, partially unsaturated, or aromatic monocyclic ring, the 3-7 membered ring having 0-3 heteroatoms selected from the group consisting of oxygen, nitrogen, and sulfur; or an 7-12 membered fully saturated, partially unsaturated, or aromatic bicyclic ring having 0-5 heteroatoms selected from the group consisting of oxygen, nitrogen, and sulfur;

$J^Z$ is independently $C_{1-6}$aliphatic, =O, halo, or →O;

$J^{Q1}$ is independently-CN, halo, =O, $Q^2$, or a $C_{1-8}$aliphatic chain, wherein up to three methylene units of the aliphatic chain are optionally replaced with —O—, —$NR^a$—, —C(O)—, or —$S(O)_z$—; each occurrence of $J^{Q1}$ is optionally substituted by 0-3 occurrences of $J^R$; or two occurrences of $J^{Q1}$ on the same atom, taken together with the atom to which they are joined, form a 3-6 membered ring having 0-2 heteroatoms selected from the group consisting of oxygen, nitrogen, and sulfur; wherein the ring formed by two occurrences of $J^{Q1}$ is optionally substituted with 0-3 occurrences of $J^X$; or two occurrences of $J^{Q1}$, together with $Q^1$, form a 6-10 membered saturated or partially unsaturated bridged ring system;

$Q^2$ is independently selected from a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;

$J^R$ is independently —CN, halo, =O, →O; $Q^3$, or a $C_{1-6}$aliphatic chain, wherein up to three methylene units of the aliphatic chain are optionally replaced with —O—, —$NR^a$—, —C(O)—, or —$S(O)_z$—; each $J^R$ is optionally substituted with 0-3 occurrences of $J^T$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or two occurrences of $J^R$, together with $Q^2$, form a 6-10 membered saturated or partially unsaturated bridged ring system;

$Q^3$ is a 3-7 membered fully saturated, partially unsaturated, or aromatic monocyclic ring having 0-3 heteroatoms selected from the group consisting of oxygen, nitrogen, and sulfur; or an 7-12 membered fully saturated, partially unsaturated, or aromatic bicyclic ring having 0-5 heteroatoms selected from the group consisting of oxygen, nitrogen, and sulfur;

$J^X$ is independently —CN, =O, halo, or a $C_{1-4}$aliphatic chain; wherein up to two methylene units of the aliphatic chain are optionally replaced with —O—, —$NR^a$—, —C(O)—, or —$S(O)_z$—;

$J^T$ is independently halo, —CN, →O; =O, —OH, a $C_{1-6}$aliphatic chain, wherein up to two methylene units of the aliphatic chain are optionally replaced with —O—, —$NR^a$—, —C(O)—, or —$S(O)_z$—; or a 3-6 membered non-aromatic ring having 0-2 heteroatoms selected from the group consisting of oxygen, nitrogen, and sulfur; each occurrence of $J^T$ is optionally substituted with 0-3 occurrences of $J^M$; or two occurrences of $J^T$ on the same atom, together with the atom to which they are joined, form a 3-6 membered ring having 0-2 heteroatoms selected from the group consisting of oxygen, nitrogen, and sulfur; or two occurrences of $J^T$, together with $Q^3$, form a 6-10 membered saturated or partially unsaturated bridged ring system;

$J^M$ is independently halo or $C_{1-6}$aliphatic;

z is 0, 1 or 2; and $R^a$ is independently H or $C_{1-4}$aliphatic.

In some embodiments, $R^{10}$ and $R^3$ are fluoro.

In other embodiments, $R^4$ is Q1.

In still other embodiments, $Q^1$ is independently piperidinyl and imidazolyl.

In another embodiment, the ATR inhibitor is represented by Formula A-II-a:

A-II-a

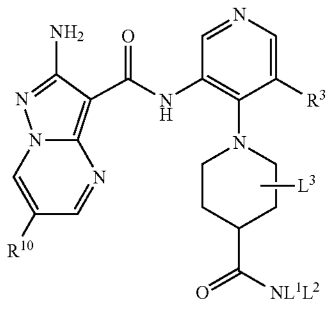

or a pharmaceutically acceptable salt or prodrug thereof, wherein:

$R^{10}$ is fluoro, chloro, or —$C(J^{10})_2CN$;

$J^{10}$ is independently H or $C_{1-2}$alkyl; or two occurrences of $J^{10}$, together with the carbon atom to which they are attached, form an optionally substituted 3-4 membered carbocyclic ring;

$R^3$ is H; chloro; fluoro; $C_{1-4}$alkyl optionally substituted with 1-3 occurrences of halo; C3-4cycloalkyl; —CN; or a $C_{1-3}$aliphatic chain, wherein up to two methylene units of the aliphatic chain are optionally replaced with —O—, —$NR^a$—, —C(O)—, or —$S(O)_z$;

$L^1$ is H; a 3-7 membered aromatic or non-aromatic ring having 0-2 heteroatoms selected from the group consisting of oxygen, nitrogen, and sulfur; or a $C_{1-6}$aliphatic chain, wherein up to two methylene units of the aliphatic chain are optionally replaced with —O—, —$NR^a$—, —C(O)—, or —$S(O)_z$;

each $L^1$ is optionally substituted with $C_{1-4}$aliphatic; —CN; halo; —OH; or a 3-6 membered non-aromatic ring having 0-2. heteroatoms selected from the group consisting of oxygen, nitrogen, and sulfur;

$L^2$ is H; a 3-7 membered aromatic or non-aromatic ring having 0-2 heteroatoms selected from the group consisting of oxygen, nitrogen, and sulfur; or a $C_{1-6}$aliphatic chain, wherein up to two methylene units of the aliphatic chain are optionally replaced with —O—, —$NR^a$—, —C(O)—, or —$S(O)_z$; each $L^2$ is optionally substituted with $C_{1-4}$aliphatic; —CN; halo; —OH; or a 3-6 membered non-aromatic ring having 0-2 heteroatoms selected from the group consisting of oxygen, nitrogen, and sulfur; or $L^1$ and $L^2$, together with the nitrogen to which they are attached, form a Ring D; Ring D is optionally substituted with 0-5 occurrences of $J^G$;

$L^3$ is H, $C_{1-3}$aliphatic, or CN;

Ring D is a 3-7 membered heterocyclyl ring having 1-2 heteroatoms selected from the group consisting of oxygen, nitrogen, and sulfur; or an 7-12 membered fully saturated or partially unsaturated bicyclic ring having 1-5 heteroatoms selected from the group consisting of oxygen, nitrogen, and sulfur;

$J^G$ is independently halo; —CN; —$N(R^o)_2$; →O; a 3-6 membered carbocyclyl; a 3-6 membered heterocyclyl having 1-2 heteroatoms selected from the group consisting of oxygen, nitrogen, and sulfur; or a $C_{1-4}$alkyl chain, wherein up to two methylene units of the alkyl chain are optionally replaced with —O—, —$NR^a$—, —C(O)—, or —$S(O)_z$; each $J^G$ is optionally substituted with 0-2 occurrences of $J^K$;

two occurrences of $J^G$ on the same atom, together with the atom to which they are joined, form a 3-6 membered ring having 0-2 heteroatoms selected from the group consisting of oxygen, nitrogen, and sulfur; or two occurrences of $J^G$, together with Ring D, form a 6-10 membered saturated or partially unsaturated bridged ring system;

$J^K$ is a 3-7 membered aromatic or non-aromatic ring having 0-2 heteroatoms selected from the group consisting of oxygen, nitrogen, and sulfur;

z is 0, 1, or 2; and $R^a$ and $R^o$ are independently H or $C_{1-4}$alkyl.

In another embodiment, $R^{10}$ and $R^3$ are fluoro.

In other preferred embodiments, the ATR inhibitor is a compound represented by the following formula (Compound 2):

Compound 2

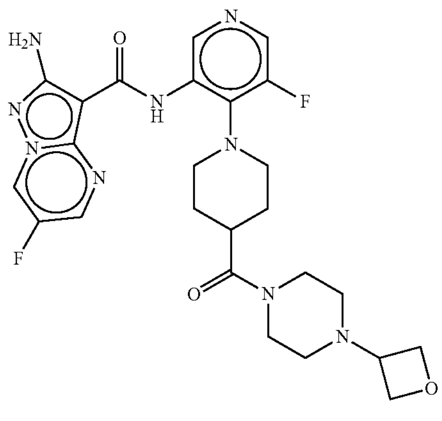

or a pharmaceutically acceptable salt thereof. Compound 2 is also referred to as 2-amino-6-fluoro-N-(5-fluoro-4-{4-[4-(oxetan-3-yl)piperazine-1-carbonyl]piperidin-1-yl}pyridin-3-yl)pyrazolo[1,5-a]pyrimidine-3-carboxamide.

In some preferred embodiments, the ATR inhibitor is a compound represented by the following formula (Compound 3):

Compound 3

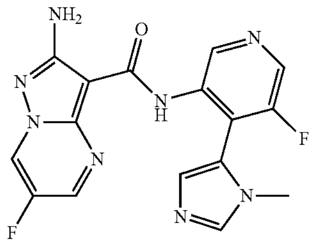

or a pharmaceutically acceptable salt thereof. Compound 3 is also referred to as 2-Amino-6-fluoro-N-[5-fluoro-4-(1-methyl-1H-imidazol-5-yl)pyridin-3-yl]pyrazolo[1,5-a]pyrimidine-3-carboxamide.

Another preferred ATR inhibitor is AZD6738, which is also known as ceralasertib (CAS Registry Number 1352226-88-0), or a pharmaceutically acceptable salt thereof. It has the chemical formula 4-{4-[(3R)-3-methylmorpholin-4-yl]-6-[1-(S-methylsulfonimidoyl)cyclopropyl]pyrimidin-2-yl}-1H-pyrrolo[2,3-b]pyridine and is represented by the following formula (Compound 4):

Compound 4

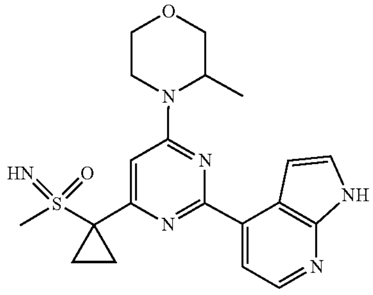

or a pharmaceutically acceptable salt thereof.

Another preferred ATR inhibitor has the chemical formula 2-[(3R)-3-methylmorpholin-4-yl]-4-(1-methyl-1H-pyrazol-5-yl)-8-(1H-pyrazol-5-yl)-1,7-naphthyridine and is represented by the following formula (Compound 5):

Compound 5

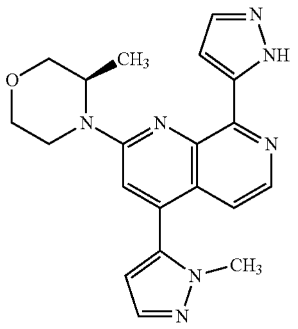

or a pharmaceutically acceptable salt thereof.

In some embodiments, the ATR inhibitor is selected from the following group:

Compound 6

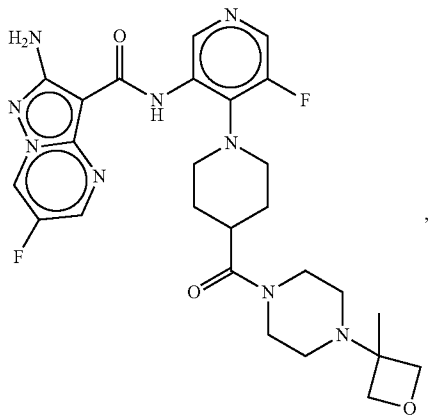

,

Compound 7

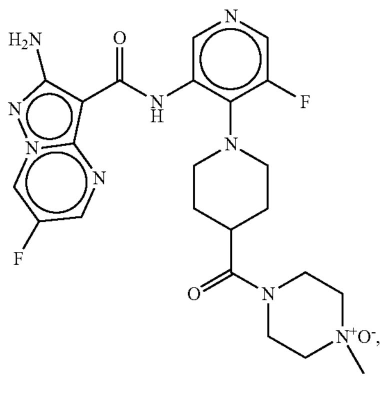

-continued

Compound 8

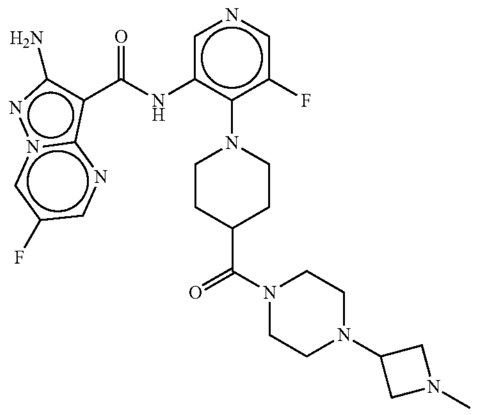

, or a pharmaceutically acceptable salt thereof.

Further preferred examples of ATR inhibitors that can be used in combination therapy of the invention are compounds of the formula I below

I

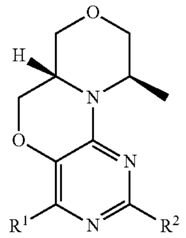

in which $R^1$ denotes $C(CH_3)_2SO_2A'$, $CH_2OSO_2A'$, $C(CH_3)_2OH$, $—[C(R^3)_2]_nHet^1$, or 1-methylsulfonyl-cycloprop-1-yl, $R^2$ denotes $Het^2$, $NR^3(CH2)_nHet^2$, $OHet^2$, $Ar^1$, $CONHHet^3$, $COHet^3$ or CONHA, $R^3$ denotes H or A', $Het^1$ denotes imidazolyl, pyrazolyl, triazolyl or pyridyl, each of which is unsubstituted or monosubstituted by COOH, COOA', $CH_2OH$, $CH_2OA'$ or A, $Het^2$ denotes 1H-pyrrolo[2,3-b]pyridinyl, 1H-pyrrolo[2,3-c]pyridinyl, indolyl, benzimidazolyl, imidazolyl, 1,2,3,4-tetrahydroisoquinolyl, pyridyl, triazolyl, pyrazolyl, quinolyl, isoquinolyl, quinazolinyl or 1,3-dihydro-2lamda6-2,2-dioxo-1-benzothiazolyl, each of which is unsubstituted or mono- or disubstituted by Hal, A', $—[C(R^3)_2]_nOR^3$, $CONH_2$, $SO_2$phenyl, benzyl, CN, $—[C(R^3)_2]_nNH_2$, $—[C(R^3)_2]_nNHA$, oxetanyl-NH— and/or NHCOA, $Het^3$ denotes triazolyl, pyridazinyl, pyrimidinyl, pyrazolyl or pyrrolidinyl each of which is unsubstituted or monosubstituted by $—[C(R^3)_2]_nOR^3$, $—[C(R^3)_2]_nNH_2$ or $=O$, $Ar^1$ denotes phenyl monosubstituted by $—[C(R^3)_2]_nOR^3$, imidazolyl, $—[C(R^3)_2]_nNH_2$, pyrazolyl, aziridinyl or oxetanyl, each of which may be unsubstituted or monosubstituted by $—[C(R^3)_2]_nOR^3$ or $—[C(R^3)_2]_nNH_2$, A denotes unbranched or branched alkyl having 1-6 C-atoms, in which 1-7 H atoms may be replaced by OH, F, Cl and/or Br and/or in which one or two non-adjacent CH2 groups may be replaced by 0 and/or NH groups, A' denotes unbranched or branched alkyl having 1-4 C-atoms, Hal denotes F, Cl, Br or I, n denotes 0, 1, 2 or 3, and pharmaceutically acceptable salts, tautomers and stereoisomers thereof, including mixtures thereof in all ratios.

In preferred embodiments $R^1$ denotes $C(CH_3)_2SO_2A'$ or $C(CH_3)_2OH$.

In further preferred embodiments $R^2$ denotes $Het^2$.

In further preferred embodiments $R^3$ denotes H.

In further preferred embodiments A denotes unbranched or branched alkyl having 1-6 C-atoms, in which 1-5 H atoms may be replaced by OH and/or F.

In further preferred embodiments $Het^2$ denotes 1H-pyrrolo[2,3-b]pyridinyl, 1H-pyrrolo[2,3-c]pyridinyl, indolyl, benzimidazolyl or imidazolyl, each of which is mono- or disubstituted by Hal, $—[C(R^3)_2]_nNH_2$ and/or $—[C(R^3)_2]_n$ NHA, In further preferred embodiments $R^1$ denotes $C(CH_3)_2SO_2A'$ or $C(CH_3)_2OH$, $R^2$ denotes $Het^2$,

- $Het^2$ denotes 1H-pyrrolo[2,3-b]pyridinyl, 1H-pyrrolo[2,3-c]pyridinyl, indolyl, benzimidazolyl or imidazolyl, each of which is unsubstituted or mono- or disubstituted by Hal, OH, $—[C(R^3)_2]_nNH_2$, $—[C(R^3)_2]_nNHA$, oxetanyl-NH- and/or NHCOA,
- A denotes denotes unbranched or branched alkyl having 1-6 C-atoms, in
- which 1-5 H atoms may be replaced by OH and/or F,
- A' denotes unbranched or branched alkyl having 1-4 C-atoms,
- Hal denotes F, Cl, Br or I,
- n denotes 0, 1, 2 or 3.

In further preferred embodiments $R^1$ denotes $C(CH3)_2SO_2CH_3$ or $C(CH_3)_{20}H$, $R^2$. denotes $Het^2$, $R^3$ denotes H, $Het^2$ denotes 1H-pyrrolo[2,3-b]pyridinyl, 1H-pyrrolo[2,3-c]pyridinyl, indolyl, benzimidazolyl or imidazolyl, each of which is mono- or disubstituted by Hal, $—[C(R^3)_2]_nNH_2$ and/or $—[C(R^3)_2]_nNHA$,

- A denotes unbranched or branched alkyl having 1-6 C-atoms, in which 1-5 H atoms may be replaced by OH and/or F, A' denotes unbranched or branched alkyl having 1-4 C-atoms, Hal denotes F, Cl, Br or I, n denotes 0, 1, 2 or 3

Specially preferred embodiments of the ATRi of the present invention are depicted below

| No. | Structure |
| --- | --- |
| "A1" | 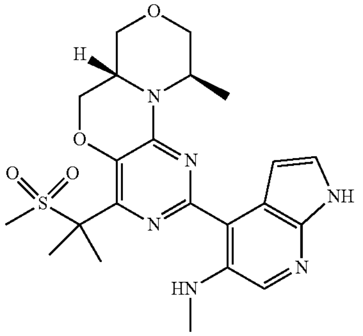 [SMILES: CNc1cnc2[nH]ccc2c1-c1nc2c(c(C(C)(C)S(C)(=O)=O)n1)OC[C@@H]1COC[C@@H](C)N21] |

-continued

| No. | Structure |
| --- | --- |
| "A2" | 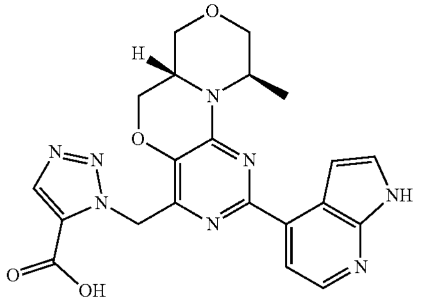 [SMILES: C[C@@H]1COC[C@H]2COc3c(Cn4nncc4C(=O)O)nc(-c4ccnc5[nH]ccc45)nc3N21] |
| "A3" | 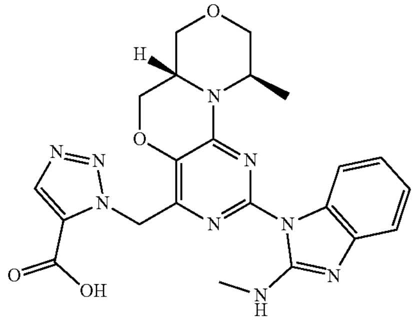 [SMILES: CNc1nc2ccccc2n1-c1nc(Cn2nncc2C(=O)O)c2c(n1)N1[C@@H](COC[C@H]1C)CO2] |
| "A4" | 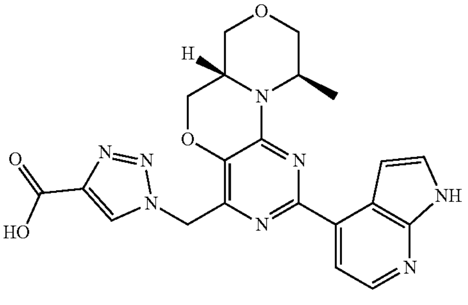 [SMILES: C[C@@H]1COC[C@H]2COc3c(Cn4cc(C(=O)O)nn4)nc(-c4ccnc5[nH]ccc45)nc3N21] |
| "A5" | 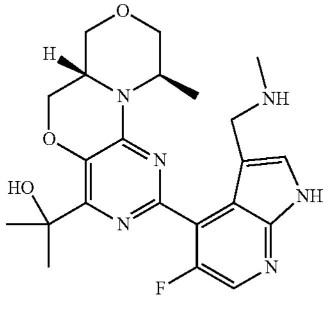 [SMILES: CNCc1c[nH]c2ncc(F)c(-c3nc4c(c(C(C)(C)O)n3)OC[C@@H]3COC[C@@H](C)N43)c12] |
| "A6" | 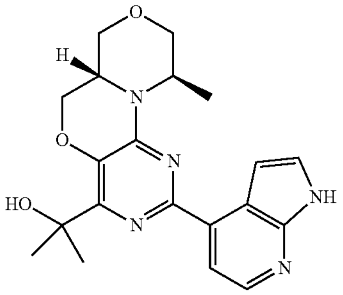 [SMILES: C[C@@H]1COC[C@H]2COc3c(nc(-c4ccnc5[nH]ccc45)nc3C(C)(C)O)N21] |

-continued
| No. | Structure |
| --- | --- |
| "A7" | 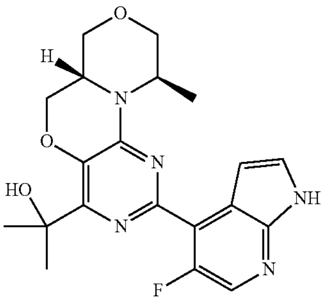 [SMILES: C[C@@H]1COC[C@H]2COc3c(nc(-c4c(F)cnc5[nH]ccc45)nc3C(C)(C)O)N21] |
| "A8" | 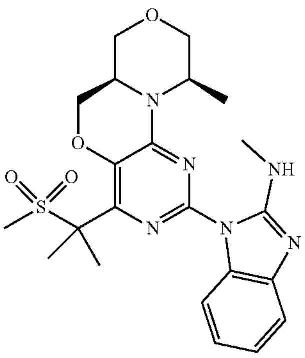 [SMILES: CNc1nc2ccccc2n1-c1nc2c(c(C(C)(C)S(C)(=O)=O)n1)OC[C@H]1COC[C@@H](C)N21] |
| "A9" | 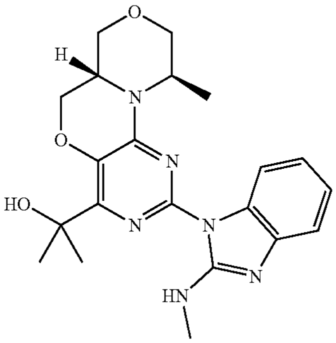 [SMILES: CNc1nc2ccccc2n1-c1nc2c(c(C(C)(C)O)n1)OC[C@@H]1COC[C@@H](C)N21] |
| "A10" | 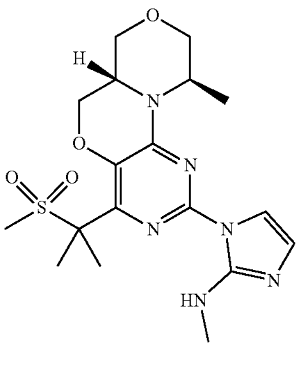 [SMILES: CNc1nccn1-c1nc2c(c(C(C)(C)S(C)(=O)=O)n1)OC[C@@H]1COC[C@@H](C)N21] |
-continued
| No. | Structure |
| --- | --- |
| "A11" | 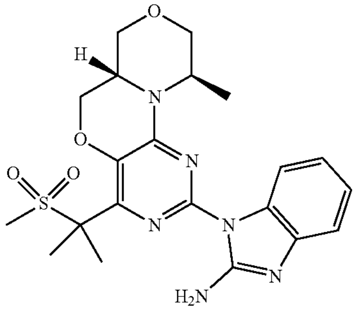 [SMILES: C[C@@H]1COC[C@H]2COc3c(nc(-n4c(N)nc5ccccc54)nc3C(C)(C)S(C)(=O)=O)N21] |
| "A12" | 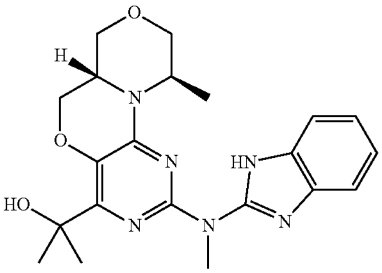 [SMILES: C[C@@H]1COC[C@H]2COc3c(nc(N(C)c4nc5ccccc5[nH]4)nc3C(C)(C)O)N21] |
| "A13" | 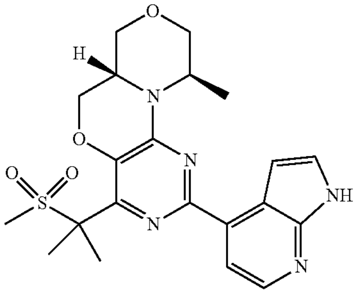 [SMILES: C[C@@H]1COC[C@H]2COc3c(nc(-c4ccnc5[nH]ccc45)nc3C(C)(C)S(C)(=O)=O)N21] |
| "A14" | 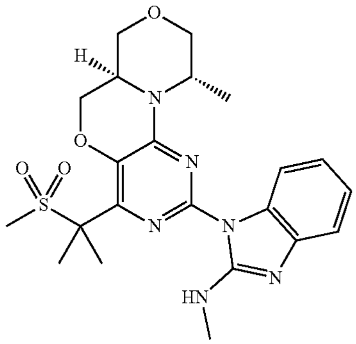 [SMILES: CNc1nc2ccccc2n1-c1nc2c(c(C(C)(C)S(C)(=O)=O)n1)OC[C@H]1COC[C@H](C)N21] |
| "A15" | 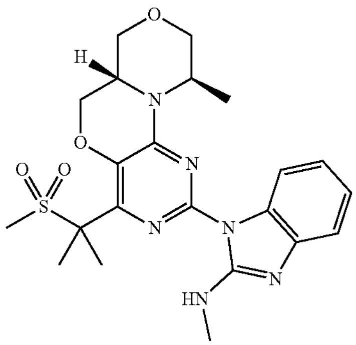 [SMILES: CNc1nc2ccccc2n1-c1nc2c(c(C(C)(C)S(C)(=O)=O)n1)OC[C@@H]1COC[C@@H](C)N21] |

| No. | Structure |
|---|---|
| "A16" | 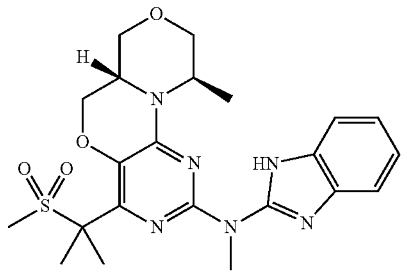 [SMILES: C[C@@H]1COC[C@H]2COc3c(nc(N(C)c4nc5ccccc5[nH]4)nc3C(C)(C)S(C)(=O)=O)N21] |
| "A17" | 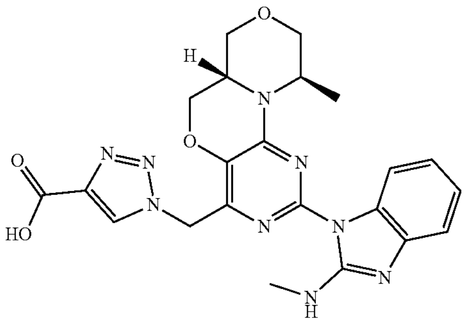 [SMILES: CNc1nc2ccccc2n1-c1nc(Cn2cc(C(=O)O)nn2)c2c(n1)N1[C@@H](COC[C@H]1C)CO2] |
| "A18" | 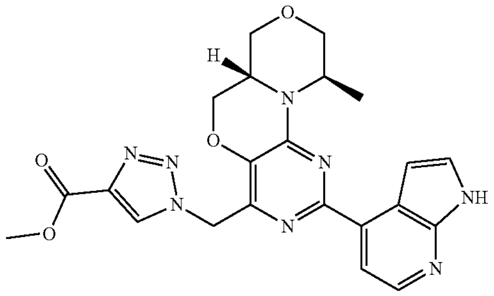 [SMILES: COC(=O)c1cn(Cc2nc(-c3ccnc4[nH]ccc34)nc3c2OC[C@@H]2COC[C@@H](C)N32)nn1] |
| "A19" | 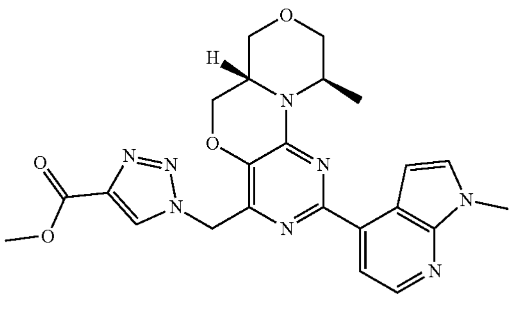 |
| "A20" | 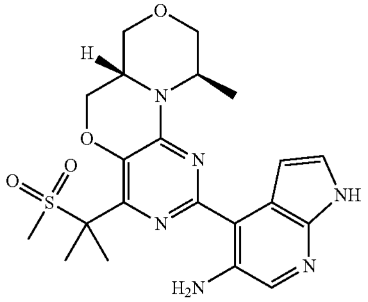 [SMILES: C[C@@H]1COC[C@H]2COc3c(nc(-c4c(N)cnc5[nH]ccc45)nc3C(C)(C)S(C)(=O)=O)N21] |
| No. | Structure |
|---|---|
| "A21" | 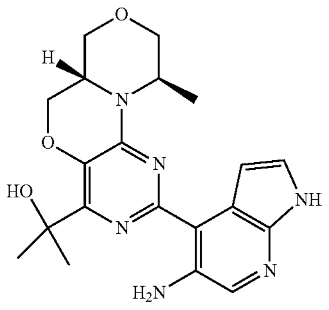 [SMILES: C[C@@H]1COC[C@H]2COc3c(nc(-c4c(N)cnc5[nH]ccc45)nc3C(C)(C)O)N21] |
| "A22" | 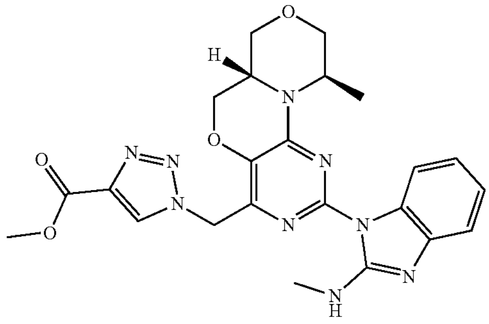 [SMILES: CNc1nc2ccccc2n1-c1nc(Cn2cc(C(=O)OC)nn2)c2c(n1)N1[C@@H](COC[C@H]1C)CO2] |
| "A23" | 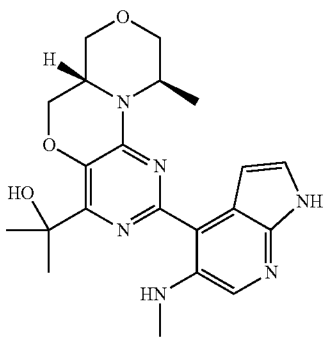 [SMILES: CNc1cnc2[nH]ccc2c1-c1nc2c(c(C(C)(C)O)n1)OC[C@@H]1COC[C@@H](C)N21] |
| "A24" | 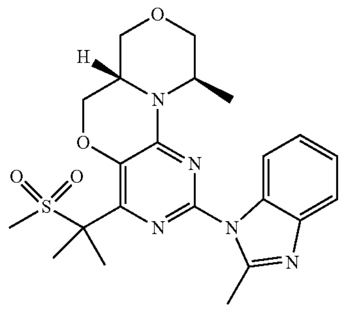 [SMILES: Cc1nc2ccccc2n1-c1nc2c(c(C(C)(C)S(C)(=O)=O)n1)OC[C@@H]1COC[C@@H](C)N21] |

-continued
| No. | Structure |
|---|---|
| "A25" | 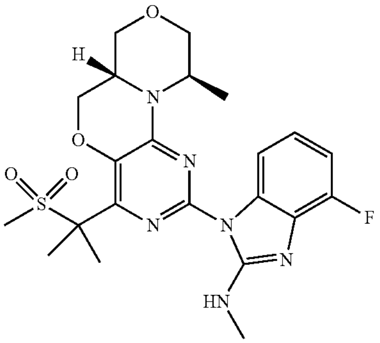 [SMILES: CNc1nc2c(F)cccc2n1-c1nc2c(c(C(C)(C)S(C)(=O)=O)n1)OC[C@@H]1COC[C@@H](C)N21] |
| "A26" | 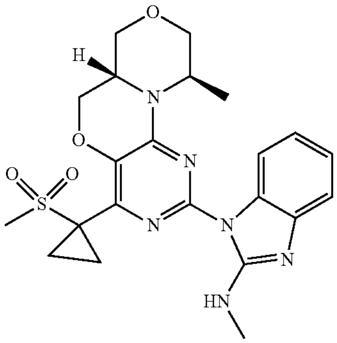 [SMILES: CNc1nc2ccccc2n1-c1nc2c(c(C3(S(C)(=O)=O)CC3)n1)OC[C@@H]1COC[C@@H](C)N21] |
| "A27" | 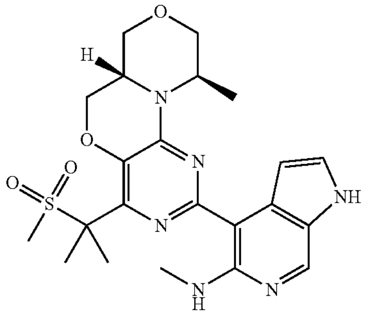 [SMILES: CNc1ncc2[nH]ccc2c1-c1nc2c(c(C(C)(C)S(C)(=O)=O)n1)OC[C@@H]1COC[C@@H](C)N21] |
| "A28" | 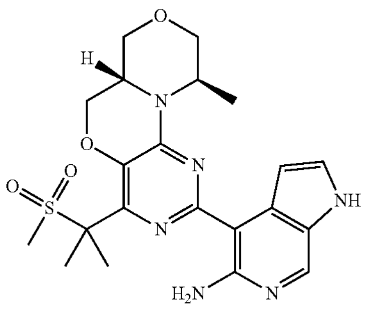 [SMILES: C[C@@H]1COC[C@H]2COc3c(nc(-c4c(N)ncc5[nH]ccc45)nc3C(C)(C)S(C)(=O)=O)N21] |
-continued
| No. | Structure |
|---|---|
| "A29" | 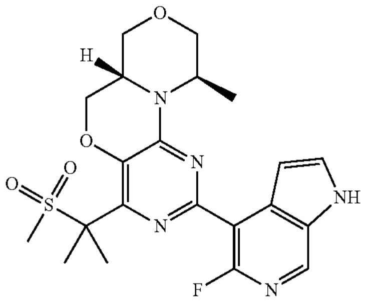 [SMILES: C[C@@H]1COC[C@H]2COc3c(nc(-c4c(F)ncc5[nH]ccc45)nc3C(C)(C)S(C)(=O)=O)N21] |
| "A30" | 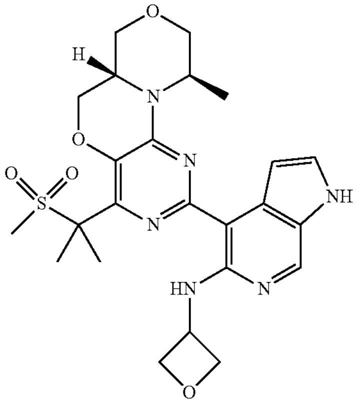 [SMILES: C[C@@H]1COC[C@H]2COc3c(nc(-c4c(NC5COC5)ncc5[nH]ccc45)nc3C(C)(C)S(C)(=O)=O)N21] |
| "A31" | 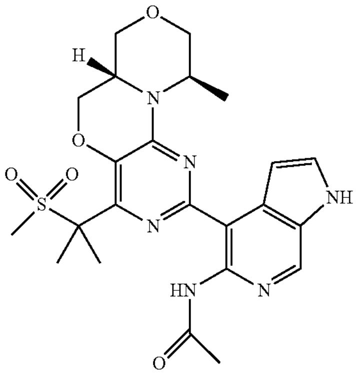 [SMILES: CC(=O)Nc1ncc2[nH]ccc2c1-c1nc2c(c(C(C)(C)S(C)(=O)=O)n1)OC[C@@H]1COC[C@@H](C)N21] |
| "A32" | 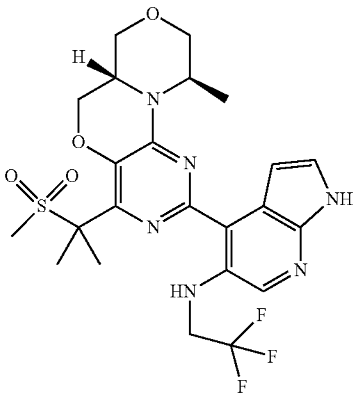 [SMILES: C[C@@H]1COC[C@H]2COc3c(nc(-c4c(NCC(F)(F)F)cnc5[nH]ccc45)nc3C(C)(C)S(C)(=O)=O)N21] |

-continued
| No. | Structure |
|---|---|
| "A33" | 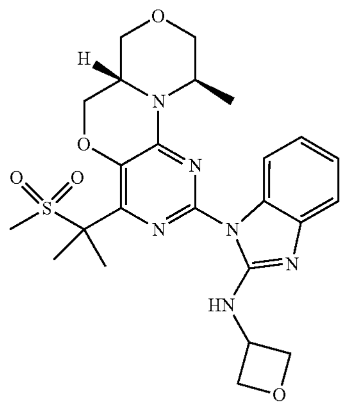 [SMILES: C[C@@H]1COC[C@H]2COc3c(nc(-n4c(NC5COC5)nc5ccccc54)nc3C(C)(C)S(C)(=O)=O)N21] |
| "A34" | 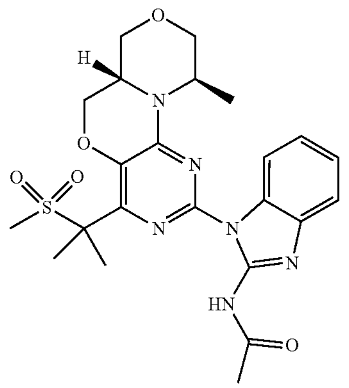 [SMILES: CC(=O)Nc1nc2ccccc2n1-c1nc2c(c(C(C)(C)S(C)(=O)=O)n1)OC[C@@H]1COC[C@@H](C)N21] |
| "A35" | 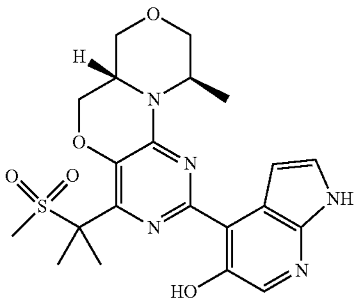 [SMILES: C[C@@H]1COC[C@H]2COc3c(nc(-c4c(O)cnc5[nH]ccc45)nc3C(C)(C)S(C)(=O)=O)N21] |
| "A36" | 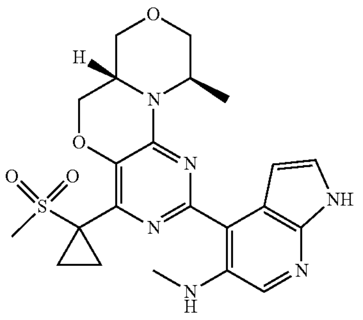 [SMILES: CNc1cnc2[nH]ccc2c1-c1nc2c(c(C3(S(C)(=O)=O)CC3)n1)OC[C@@H]1COC[C@@H](C)N21] |
-continued
| No. | Structure |
|---|---|
| "A37" | 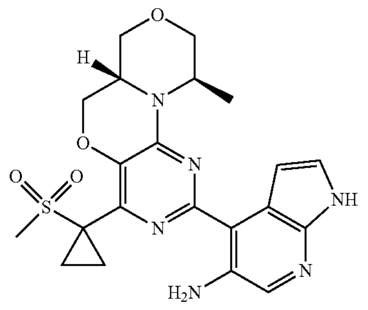 [SMILES: C[C@@H]1COC[C@H]2COc3c(nc(-c4c(N)cnc5[nH]ccc45)nc3C3(S(C)(=O)=O)CC3)N21] |
| "A38" | 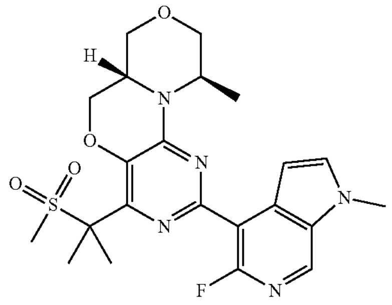 [SMILES: C[C@@H]1COC[C@H]2COc3c(nc(-c4c(F)ncc5c4ccn5C)nc3C(C)(C)S(C)(=O)=O)N21] |
| "A39" | 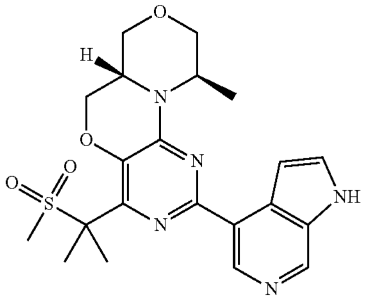 [SMILES: C[C@@H]1COC[C@H]2COc3c(nc(-c4cncc5[nH]ccc45)nc3C(C)(C)S(C)(=O)=O)N21] |
| "A40" | 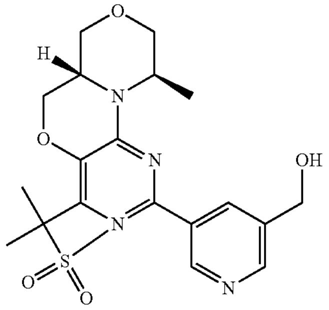 |
| "A41" | 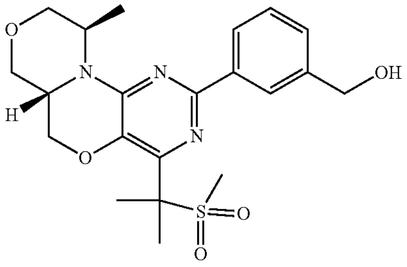 [SMILES: C[C@@H]1COC[C@H]2COc3c(nc(-c4cccc(CO)c4)nc3C(C)(C)S(C)(=O)=O)N21] |

-continued
| No. | Structure |
|---|---|
| "A42" | 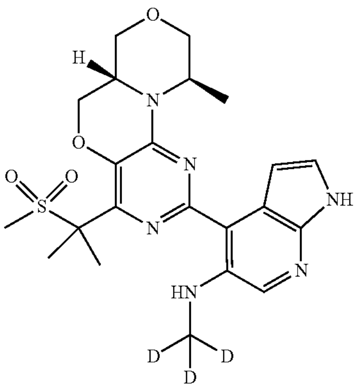 [SMILES: [2H]C([2H])([2H])Nc1cnc2[nH]ccc2c1-c1nc2c(c(C(C)(C)S(C)(=O)=O)n1)OC[C@@H]1COC[C@@H](C)N21] |
| "A43" | 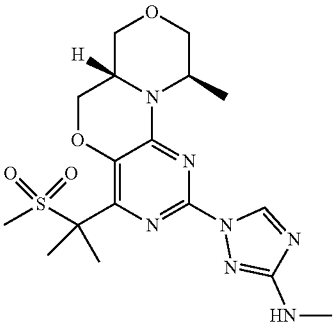 |
| "A44" | 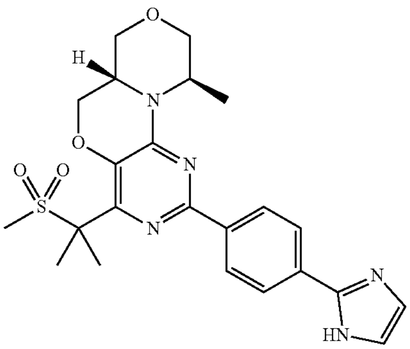 [SMILES: C[C@@H]1COC[C@H]2COc3c(nc(-c4ccc(-c5ncc[nH]5)cc4)nc3C(C)(C)S(C)(=O)=O)N21] |
| "A45" | 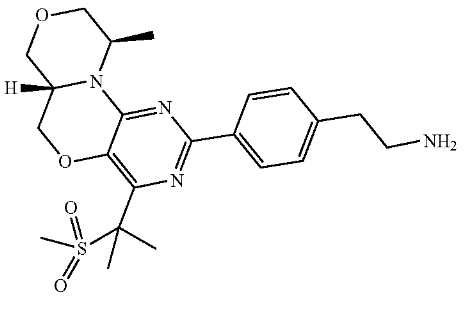 [SMILES: C[C@@H]1COC[C@H]2COc3c(nc(-c4ccc(CCN)cc4)nc3C(C)(C)S(C)(=O)=O)N21] |
-continued
| No. | Structure |
|---|---|
| "A46" | 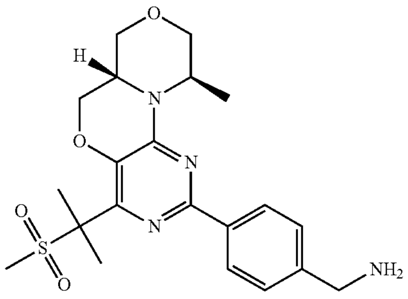 [SMILES: C[C@@H]1COC[C@H]2COc3c(nc(-c4ccc(CN)cc4)nc3C(C)(C)S(C)(=O)=O)N21] |
| "A47" | 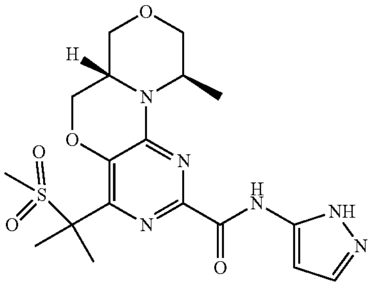 [SMILES: C[C@@H]1COC[C@H]2COc3c(nc(C(=O)Nc4ccn[nH]4)nc3C(C)(C)S(C)(=O)=O)N21] |
| "A48" | 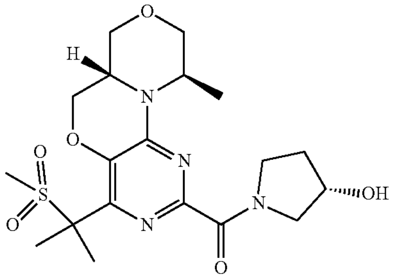 [SMILES: C[C@@H]1COC[C@H]2COc3c(nc(C(=O)N4CC[C@H](O)C4)nc3C(C)(C)S(C)(=O)=O)N21] |
| "A49" | 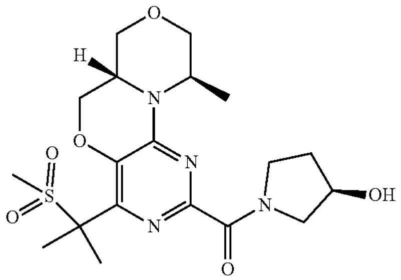 [SMILES: C[C@@H]1COC[C@H]2COc3c(nc(C(=O)N4CC[C@@H](O)C4)nc3C(C)(C)S(C)(=O)=O)N21] |
| "A50" | 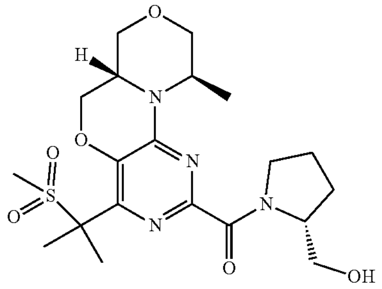 [SMILES: C[C@@H]1COC[C@H]2COc3c(nc(C(=O)N4CCC[C@@H]4CO)nc3C(C)(C)S(C)(=O)=O)N21] |

-continued
| No. | Structure |
| --- | --- |
| "A51" | 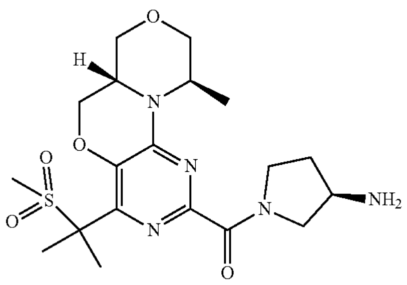 [SMILES: C[C@@H]1COC[C@H]2COc3c(nc(C(=O)N4CC[C@@H](N)C4)nc3C(C)(C)S(C)(=O)=O)N21] |
| "A52" | 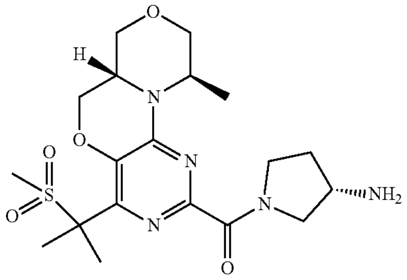 [SMILES: C[C@@H]1COC[C@H]2COc3c(nc(C(=O)N4CC[C@H](N)C4)nc3C(C)(C)S(C)(=O)=O)N21] |
| "A53" | 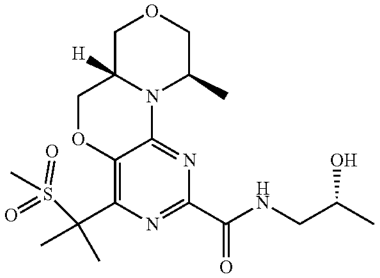 [SMILES: C[C@@H]1COC[C@H]2COc3c(nc(C(=O)NC[C@@H](C)O)nc3C(C)(C)S(C)(=O)=O)N21] |
| "A54" | 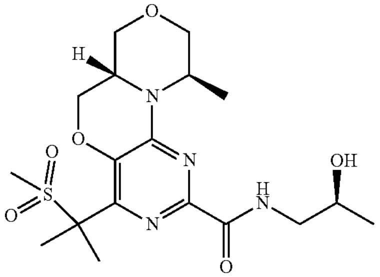 [SMILES: C[C@H](O)CNC(=O)c1nc2c(c(C(C)(C)S(C)(=O)=O)n1)OC[C@@H]1COC[C@@H](C)N21] |
| "A55" | 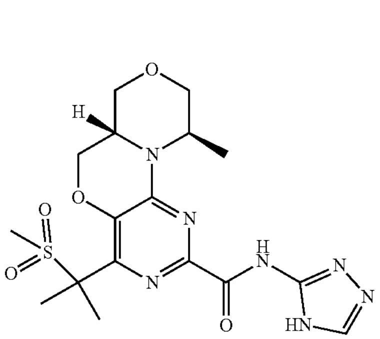 [SMILES: C[C@@H]1COC[C@H]2COc3c(nc(C(=O)Nc4nnc[nH]4)nc3C(C)(C)S(C)(=O)=O)N21] |
| "A56" | 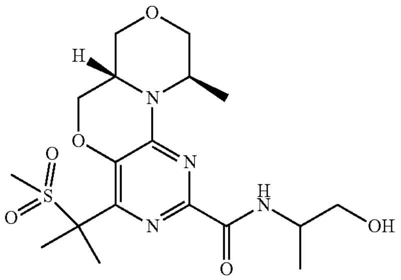 [SMILES: CC(CO)NC(=O)c1nc2c(c(C(C)(C)S(C)(=O)=O)n1)OC[C@@H]1COC[C@@H](C)N21] |
| "A57" | 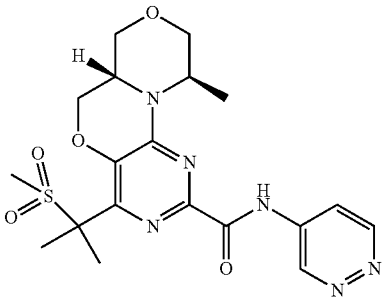 [SMILES: C[C@@H]1COC[C@H]2COc3c(nc(C(=O)Nc4ccnnc4)nc3C(C)(C)S(C)(=O)=O)N21] |
| "A58" | 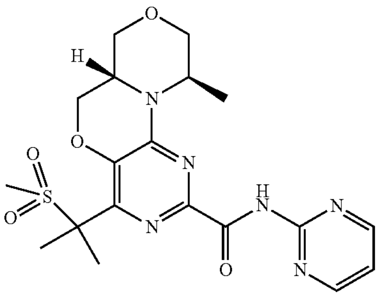 [SMILES: C[C@@H]1COC[C@H]2COc3c(nc(C(=O)Nc4ncccn4)nc3C(C)(C)S(C)(=O)=O)N21] |
| "A59" | 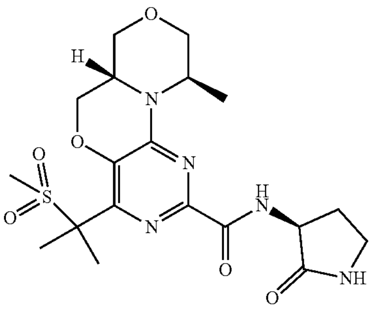 [SMILES: C[C@@H]1COC[C@H]2COc3c(nc(C(=O)N[C@H]4CCNC4=O)nc3C(C)(C)S(C)(=O)=O)N21] |
| "A60" | 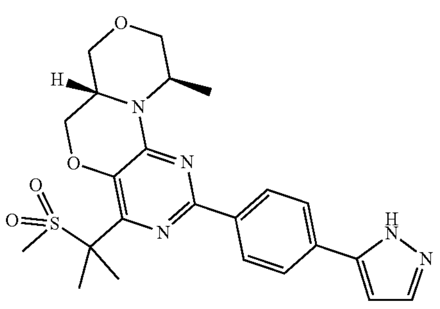 [SMILES: C[C@@H]1COC[C@H]2COc3c(nc(-c4ccc(-c5ccn[nH]5)cc4)nc3C(C)(C)S(C)(=O)=O)N21] |

-continued
| No. | Structure |
| --- | --- |
| "A61" | 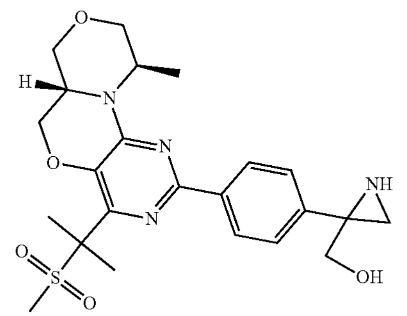 [SMILES: C[C@@H]1COC[C@H]2COc3c(nc(-c4ccc(C5(CO)CN5)cc4)nc3C(C)(C)S(C)(=O)=O)N21] |
| "A62" | 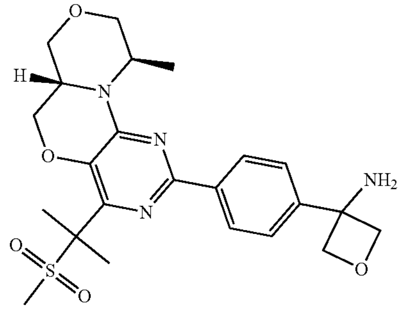 [SMILES: C[C@@H]1COC[C@H]2COc3c(nc(-c4ccc(C5(N)COC5)cc4)nc3C(C)(C)S(C)(=O)=O)N21] |
| "A63" | 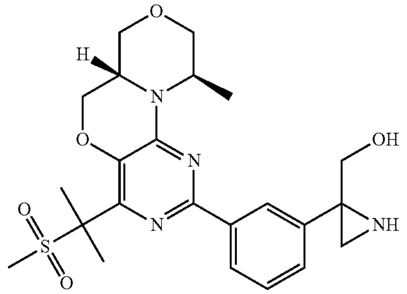 [SMILES: C[C@@H]1COC[C@H]2COc3c(nc(-c4cccc(C5(CO)CN5)c4)nc3C(C)(C)S(C)(=O)=O)N21] |
| "A64" | 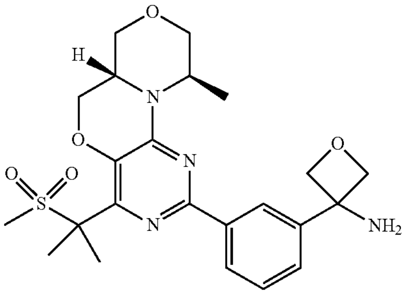 [SMILES: C[C@@H]1COC[C@H]2COc3c(nc(-c4cccc(C5(N)COC5)c4)nc3C(C)(C)S(C)(=O)=O)N21] |
| "A65" | 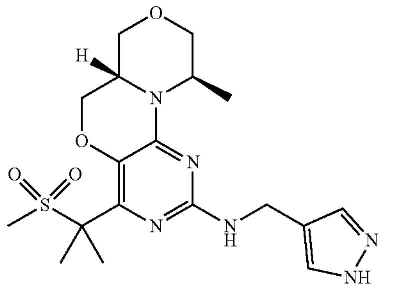 [SMILES: C[C@@H]1COC[C@H]2COc3c(nc(NCc4cn[nH]c4)nc3C(C)(C)S(C)(=O)=O)N21] |
-continued
| No. | Structure |
| --- | --- |
| "A66" | 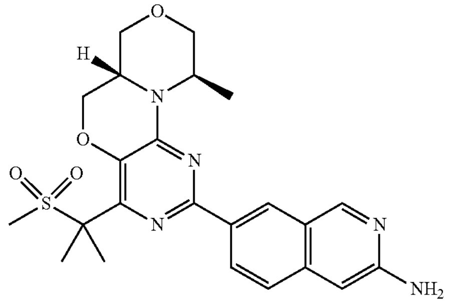 [SMILES: C[C@@H]1COC[C@H]2COc3c(nc(-c4ccc5cc(N)ncc5c4)nc3C(C)(C)S(C)(=O)=O)N21] |
| "A67" | 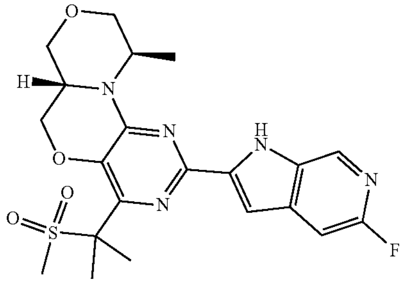 [SMILES: C[C@@H]1COC[C@H]2COc3c(nc(-c4cc5cc(F)ncc5[nH]4)nc3C(C)(C)S(C)(=O)=O)N21] |
| "A68" | 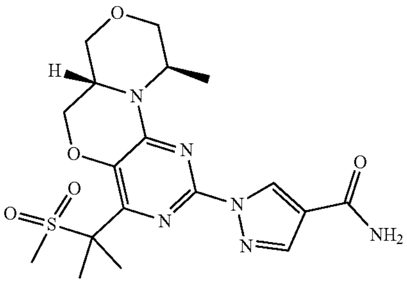 [SMILES: C[C@@H]1COC[C@H]2COc3c(nc(-n4cc(C(N)=O)cn4)nc3C(C)(C)S(C)(=O)=O)N21] |
| "A69" | 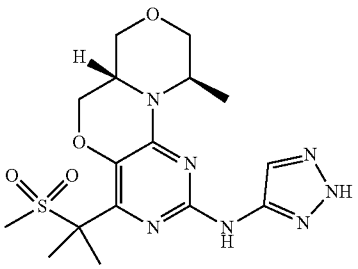 [SMILES: C[C@@H]1COC[C@H]2COc3c(nc(Nc4cn[nH]n4)nc3C(C)(C)S(C)(=O)=O)N21] |
| "A70" | 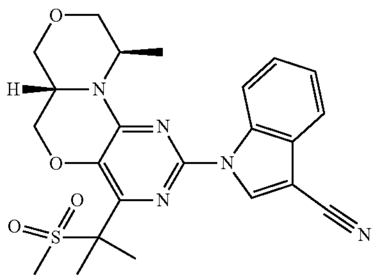 [SMILES: C[C@@H]1COC[C@H]2COc3c(nc(-n4cc(C#N)c5ccccc54)nc3C(C)(C)S(C)(=O)=O)N21] |

-continued
| No. | Structure |
|---|---|
| "A71" | 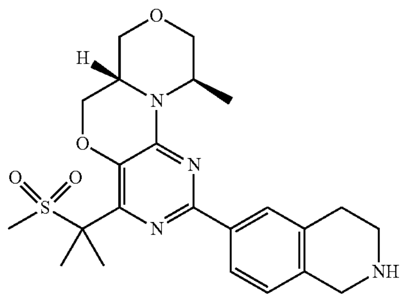 [SMILES: C[C@@H]1COC[C@H]2COc3c(nc(-c4ccc5c(c4)CCNC5)nc3C(C)(C)S(C)(=O)=O)N21] |
| "A72" | 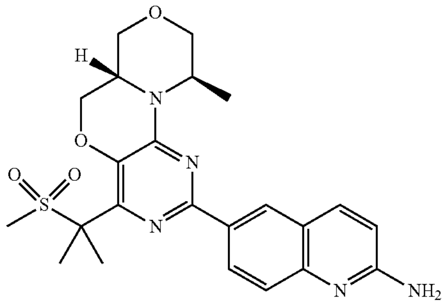 [SMILES: C[C@@H]1COC[C@H]2COc3c(nc(-c4ccc5nc(N)ccc5c4)nc3C(C)(C)S(C)(=O)=O)N21] |
| "A73" | 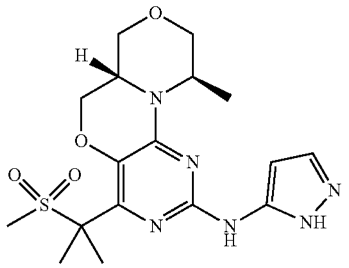 [SMILES: C[C@@H]1COC[C@H]2COc3c(nc(Nc4ccn[nH]4)nc3C(C)(C)S(C)(=O)=O)N21] |
| "A74" | 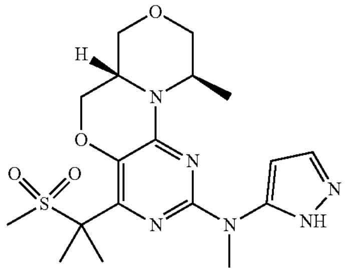 [SMILES: C[C@@H]1COC[C@H]2COc3c(nc(N(C)c4ccn[nH]4)nc3C(C)(C)S(C)(=O)=O)N21] |
| "A75" | 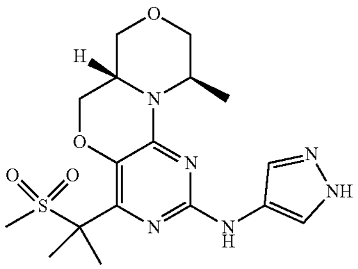 [SMILES: C[C@@H]1COC[C@H]2COc3c(nc(Nc4cn[nH]c4)nc3C(C)(C)S(C)(=O)=O)N21] |
-continued
| No. | Structure |
|---|---|
| "A76" | 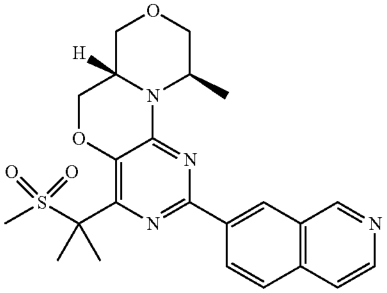 [SMILES: C[C@@H]1COC[C@H]2COc3c(nc(-c4ccc5ccncc5c4)nc3C(C)(C)S(C)(=O)=O)N21] |
| "A77" | 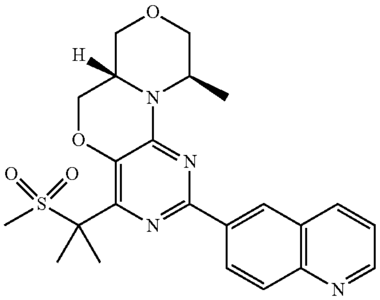 [SMILES: C[C@@H]1COC[C@H]2COc3c(nc(-c4ccc5ncccc5c4)nc3C(C)(C)S(C)(=O)=O)N21] |
| "A78" | 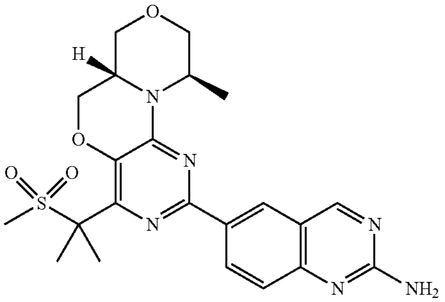 [SMILES: C[C@@H]1COC[C@H]2COc3c(nc(-c4ccc5nc(N)ncc5c4)nc3C(C)(C)S(C)(=O)=O)N21] |
| "A79" | 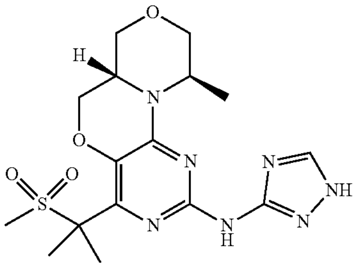 [SMILES: C[C@@H]1COC[C@H]2COc3c(nc(Nc4nc[nH]n4)nc3C(C)(C)S(C)(=O)=O)N21] |
| "A80" | 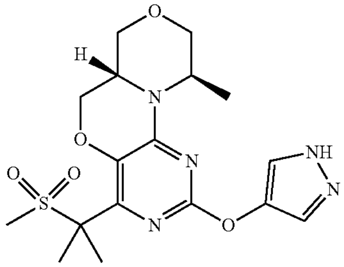 [SMILES: C[C@@H]1COC[C@H]2COc3c(nc(Oc4cn[nH]c4)nc3C(C)(C)S(C)(=O)=O)N21] |

-continued
| No. | Structure |
|---|---|
| "A81" | 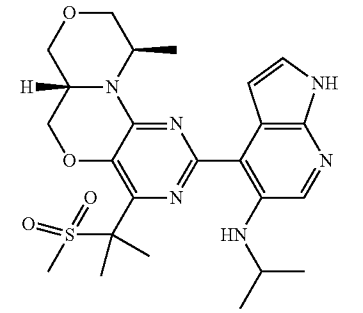 [SMILES: CC(C)Nc1cnc2[nH]ccc2c1-c1nc2c(c(C(C)(C)S(C)(=O)=O)n1)OC[C@@H]1COC[C@@H](C)N21] |
| "A82" | 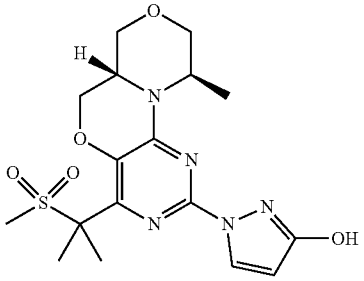 [SMILES: C[C@@H]1COC[C@H]2COc3c(nc(-n4ccc(O)n4)nc3C(C)(C)S(C)(=O)=O)N21] |
| "A83" | 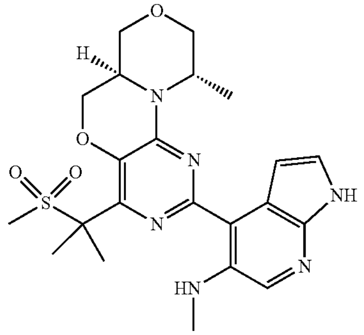 [SMILES: CNc1cnc2[nH]ccc2c1-c1nc2c(c(C(C)(C)S(C)(=O)=O)n1)OC[C@H]1COC[C@H](C)N21] |
| "A84" | 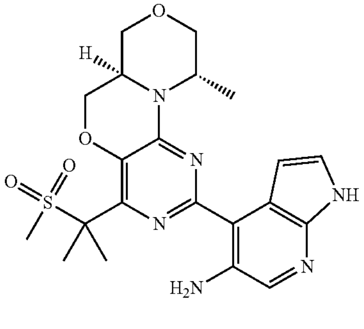 [SMILES: C[C@H]1COC[C@@H]2COc3c(nc(-c4c(N)cnc5[nH]ccc45)nc3C(C)(C)S(C)(=O)=O)N21] |
| "A85" | 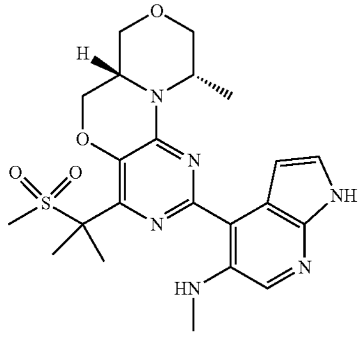 [SMILES: CNc1cnc2[nH]ccc2c1-c1nc2c(c(C(C)(C)S(C)(=O)=O)n1)OC[C@@H]1COC[C@H](C)N21] |
-continued
| No. | Structure |
|---|---|
| "A86" | 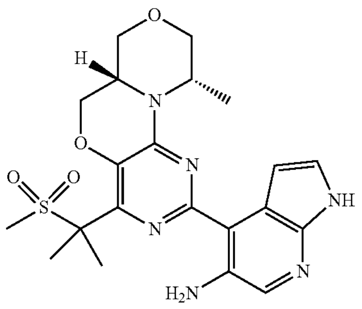 [SMILES: C[C@H]1COC[C@H]2COc3c(nc(-c4c(N)cnc5[nH]ccc45)nc3C(C)(C)S(C)(=O)=O)N21] |
| "A87" | 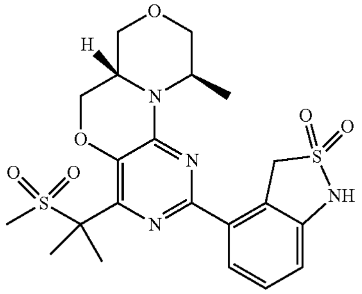 [SMILES: C[C@@H]1COC[C@H]2COc3c(nc(-c4cccc5c4CS(=O)(=O)N5)nc3C(C)(C)S(C)(=O)=O)N21] |
| "A88" | 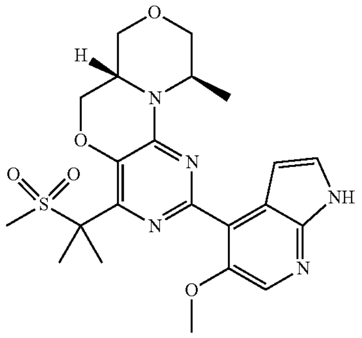 [SMILES: COc1cnc2[nH]ccc2c1-c1nc2c(c(C(C)(C)S(C)(=O)=O)n1)OC[C@@H]1COC[C@@H](C)N21] |
| "A89" | 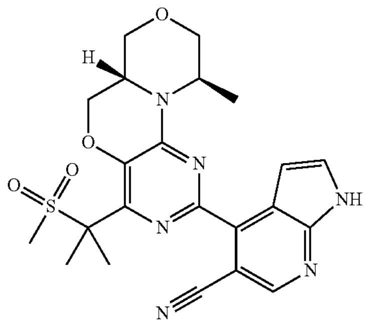 [SMILES: C[C@@H]1COC[C@H]2COc3c(nc(-c4c(C#N)cnc5[nH]ccc45)nc3C(C)(C)S(C)(=O)=O)N21] |

-continued

| No. | Structure |
|---|---|
| "A90" | 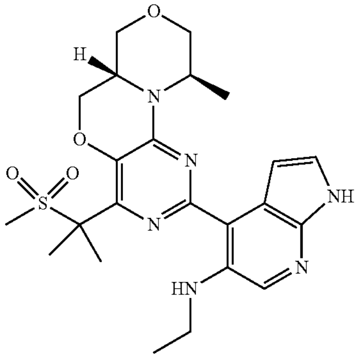 [SMILES: CCNc1cnc2[nH]ccc2c1-c1nc2c(c(C(C)(C)S(C)(=O)=O)n1)OC[C@@H]1COC[C@@H](C)N21] |
| "A91" | 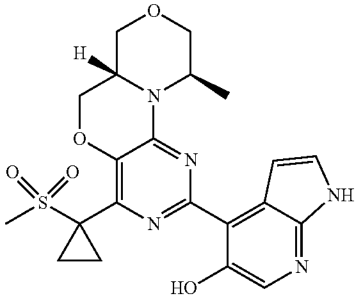 [SMILES: C[C@@H]1COC[C@H]2COc3c(nc(-c4c(O)cnc5[nH]ccc45)nc3C3(S(C)(=O)=O)CC3)N21] |
| "A92" | 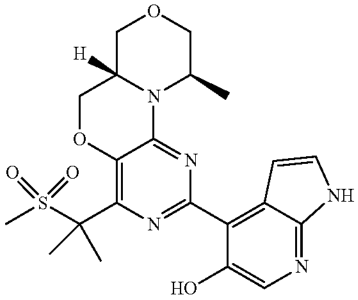 [SMILES: C[C@@H]1COC[C@H]2COc3c(nc(-c4c(O)cnc5[nH]ccc45)nc3C(C)(C)S(C)(=O)=O)N21] |
| "A93" | 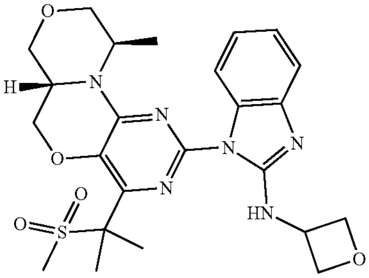 [SMILES: C[C@@H]1COC[C@H]2COc3c(nc(-n4c(NC5COC5)nc5ccccc54)nc3C(C)(C)S(C)(=O)=O)N21] |

and pharmaceutically acceptable solvates, salts, tautomers and stereoisomers thereof, including mixtures thereof in all ratios.

Further preferred embodiments of ATRi usable in the present invention are depicted in table 6.

In one embodiment, the therapeutic combination of the invention is used in the treatment of a human subject. The main expected benefit in the treatment with the therapeutic combination is a gain in risk/benefit ratio for these human patients.

In various embodiments, the therapeutic combination of the invention is employed as a first, second, third or later line of treatment. A line of treatment refers to a place in the order of treatment with different medications or other therapies received by a patient. First-line therapy regimens are treatments given first, whereas second- or third-line therapy is given after the first-line therapy or after the second-line therapy, respectively. Therefore, first-line therapy is the first treatment for a disease or condition. In patients with cancer, first-line therapy, sometimes referred to as primary therapy or primary treatment, can be surgery, chemotherapy, radiation therapy, or a combination of these therapies. Typically, a patient is given a subsequent chemotherapy regimen (second- or third-line therapy), either because the patient did not show a positive clinical outcome or only showed a sub-clinical response to a first- or second-line therapy or showed a positive clinical response but later experienced a relapse, sometimes with disease now resistant to the earlier therapy that elicited the earlier positive response.

As the mode of action differs between ATR inhibitors and DNA-alkylating ADCs, the chances to have enhanced immune-related adverse events is low. The absence of overlapping immune features in nonclinical findings or in published clinical results makes the risk low for the combination therapy of the invention to show enhanced adverse events above what is generally observed in these agents when administered alone. The identified and potential risks for the DNA-alkylating ADC and the ATR inhibitor, preferably Compound 1 or 2, of the invention, in each case as single agent, are considered to represent the potential risks for the combination treatment as well.

It is preferred that the therapeutic combination of the invention is applied in a later line of treatment, particularly a second-line or higher treatment of the cancer. There is no limitation to the prior number of therapies provided that the subject underwent at least one round of prior cancer therapy. The round of prior cancer therapy refers to a defined schedule/phase for treating a subject with, e.g., one or more chemotherapeutic agents, radiotherapy or chemoradiotherapy, and the subject failed with such previous treatment, which was either completed or terminated ahead of schedule. One reason could be that the cancer was resistant or became resistant to prior therapy. The current standard of care (SoC) for treating cancer patients often involves the administration of toxic and old chemotherapy regimens. The SoC is associated with high risks of strong adverse events that are likely to interfere with the quality of life (such as secondary cancers). In one embodiment, the combination of an ATR inhibitor and a DNA-alkylating agent may be as effective and better tolerated than SoC chemotherapy in patients with cancer resistant to mono- and/or poly-chemotherapy, radiotherapy or chemoradiotherapy.

In some embodiments, the ATR inhibitor is administered intravenously or orally. In some embodiments, the ATR inhibitor is administered by continuous infusion. Compound 1, or a pharmaceutically acceptable salt thereof, is preferably administered intravenously. Compound 2, or a pharmaceutically acceptable salt thereof, Compound 3, or a pharmaceutically acceptable salt thereof, and Compound 4, or a pharmaceutically acceptable salt thereof, are preferably administered orally. In some embodiments, the ATR inhibitor that is employed in the combination therapy may be administered at a dose of between about 20 mg/m$^2$ and about 300 mg/m$^2$, between about 30 mg/m$^2$ and about 240 mg/m$^2$, between about 40 mg/m$^2$ and about 240 mg/m$^2$, between about 40 mg/m$^2$ and about 180 mg/m$^2$, between about 60 mg/m$^2$ and about 120 mg/m$^2$, between about 80 mg/m$^2$ and about 120 mg/m$^2$, between about 90 mg/m$^2$ and about 120 mg/m$^2$, or between about 80 mg/m$^2$ and about 100 mg/m$^2$. In certain embodiments, the ATR inhibitor may be administered at a dose between about 40 $mg/m^2$ and about 300 $mg/m^2$ (e.g., about 240 $mg/m^2$). In some instances, the ATR inhibitor may be administered at a dose between about 60 $mg/m^2$ and about 180 $mg/m^2$ (e.g., 120 $mg/m^2$). In certain cases, the ATR inhibitor may be administered at a dose between about 80 $mg/m^2$ and about 100 $mg/m^2$ (e.g., about 90 $mg/m^2$). In some embodiments, the ATR inhibitor may be administered at a dose of about 40 $mg/m^2$, about 60 $mg/m^2$, about 90 $mg/m^2$ or about 120 $mg/m^2$. Preferably, the ATR inhibitor of the therapeutic combination is administered at a dose of about 90 $mg/m^2$.

In some embodiments, the ATR inhibitor is Compound 1, or a pharmaceutically acceptable salt thereof, and administered at a dose of between about 20 $mg/m^2$ and about 300 $mg/m^2$, between about 30 $mg/m^2$ and about 240 $mg/m^2$, between about 40 $mg/m^2$ and about 240 $mg/m^2$, between about 40 $mg/m^2$ and about 180 $mg/m^2$, between about 60 $mg/m^2$ and about 120 $mg/m^2$, between about 80 $mg/m^2$ and about 120 $mg/m^2$, between about 90 $mg/m^2$ and about 120 $mg/m^2$, or between about 80 $mg/m^2$ and about 100 $mg/m^2$. In some embodiments, Compound 1, or a pharmaceutically acceptable salt thereof, is administered at a dose of about 40 $mg/m^2$, about 60 $mg/m^2$, about 90 $mg/m^2$ or about 120 $mg/m^2$, preferably at a dosage of about 90 $mg/m^2$.

It should be understood that all combinations of the above-referenced ranges for dosage for use in a combination therapy, as described herein, may be possible. In addition, the dosing of the two compounds employed in the combination therapy can be adapted to one another to improve convenience and compliance.

In some embodiments, the combination regimen comprises a lead phase, optionally followed by a maintenance phase after completion of the lead phase. As used herein, the combination treatment comprises a defined period of treatment (i.e., a first phase or lead phase). After completion of such a period or phase, another defined period of treatment may follow (i.e., a second phase or maintenance phase).

The ATR inhibitor and the DNA-alkylating ADC may be administered in any order. For instance, all may be administered substantially simultaneously or sequentially. The ATR inhibitor and the DNA-alkylating ADC are administered to the patient in any order in separate compositions, formulations or unit dosage forms, or the compounds are administered together in one composition, formulation or unit dosage form.

In certain embodiments, the patient further obtains radiation therapy. In certain embodiments, the radiotherapy comprises about 35-70 Gy/20-35 fractions. In some embodiments, the radiotherapy is given either with standard fractionation (1.8 to 2 Gy for day 5 days a week) up to a total dose of 50-70 Gy in once daily. In one embodiment, stereotactic radiotherapy as well as the gamma knife are used. In the palliative setting, other fractionation schedules are also widely used for example 25 Gy in 5 fractions or 30 Gy in 10 fractions. For radiotherapy, the duration of treatment will be the time frame when radiotherapy is given. These interventions apply to treatment given with electrons, photons and protons, alfa-emitters or other ions, treatment with radio-nucleotides, for example, treatment with $^{131}I$ given to patients with thyroid cancer, as well in patients treated with boron capture neutron therapy.

Exemplary such pharmaceutically acceptable compositions are described further below and herein.

Typically, the ATR inhibitor or DNA-alkylating ADC is incorporated into a pharmaceutical composition suitable for administration to a subject, wherein the pharmaceutical composition comprises the compound and a pharmaceutically acceptable carrier. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the compound.

The compositions of the present invention may be in a variety of forms. These include, for example, liquid, semi-solid and solid dosage forms, such as liquid solutions (e.g., injectable and infusible solutions), dispersions or suspensions, tablets, pills, powders, liposomes, and suppositories. The preferred form depends on the intended mode of administration and therapeutic application. In a preferred embodiment, the DNA-alkylating ADC is administered by intravenous infusion or injection. In another preferred embodiment, the DNA-alkylating ADC is administered by intramuscular or subcutaneous injection. In a preferred embodiment, the ATR inhibitor is administered by intravenous infusion, injection or orally.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion, and by the use of surfactants. Prolonged absorption of injectable compositions can be brought about by including in the composition an agent that delays absorption, for example, monostearate salts and gelatin.

In a further aspect, a kit is provided comprising a DNA-alkylating ADC and an ATR inhibitor.

In a further aspect, a kit is provided comprising a DNA-alkylating ADC and a package insert comprising instructions for using the DNA-alkylating ADC in combination with an ATR inhibitor to treat or delay progression of a cancer in a subject. Also provided is a kit comprising an ATR inhibitor, and a package insert comprising instructions for using the ATR inhibitor in combination with a DNA-alkylating ADC to treat or delay progression of a cancer in a subject. The kit can comprise a first container and a second container, and a package insert, wherein the first container comprises at least one dose of a medicament comprising the DNA-alkylating ADC and the second container comprises at least one dose of a medicament comprising the ATR inhibitor, and the package insert comprises instructions for treating a subject for cancer using the medicaments. The ATR inhibitor and the DNA-alkylating ADC may also be comprised in a single container. The containers may be comprised of the same or different shape (e.g., vials, syringes and bottles) and/or material (e.g., plastic or glass). The kit may further comprise other materials that may be useful in administering the medicaments, such as diluents, filters, IV bags and lines, needles and syringes.

Figure 23:
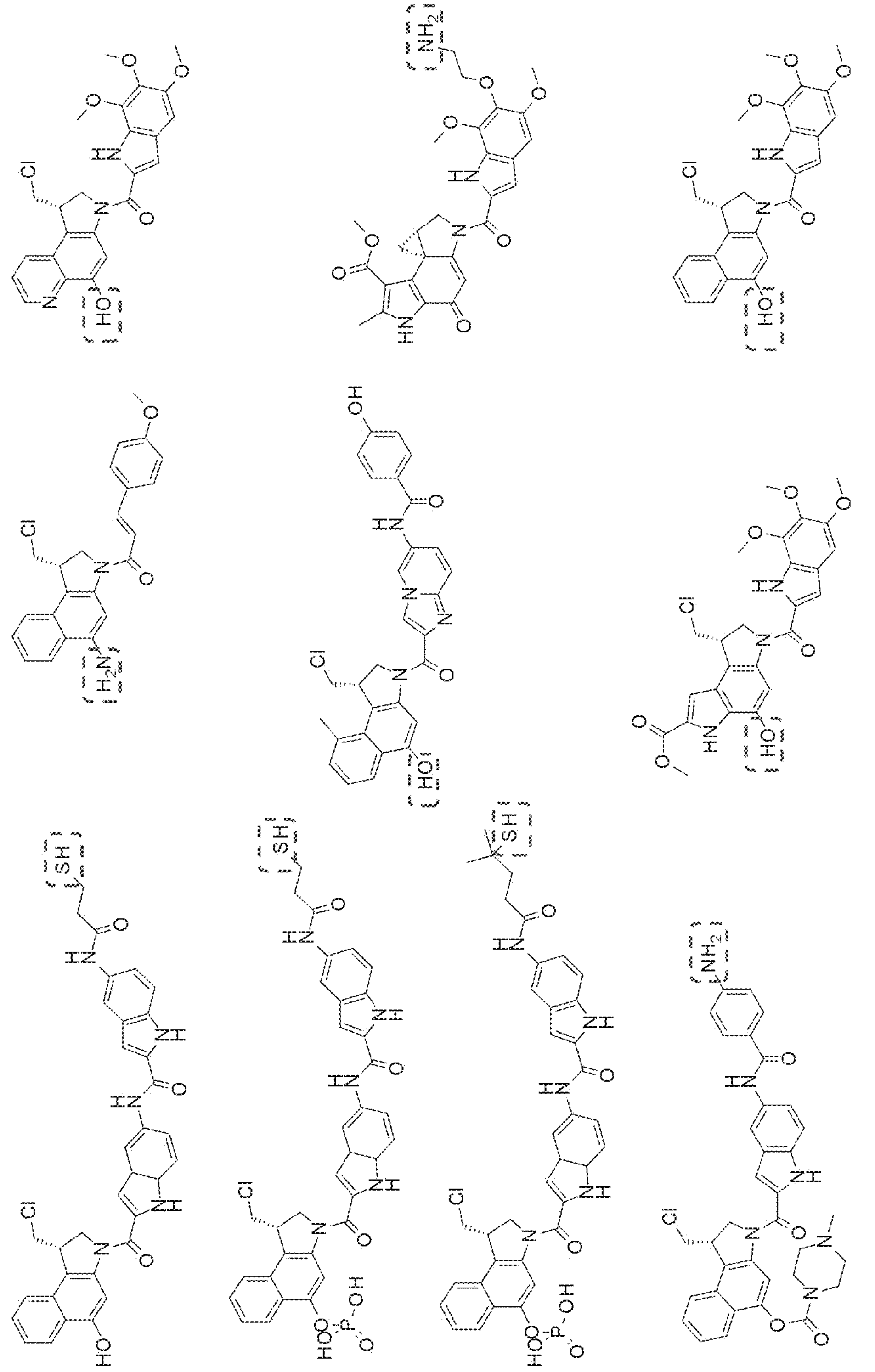
FIG. 23: Chemical structures of duocarmycin derivatives applied in the ADC format. The structures of DC1 (19), DC4 (20), DC44 (21), DU-257 (22), a minor groove binder (23), seco-DUBA (10), DSA (13), CBI-TMI (24) and a derivative of this molecule (26) are depicted. Dotted boxes indicate the attachment point of the linker.
Figure 24:
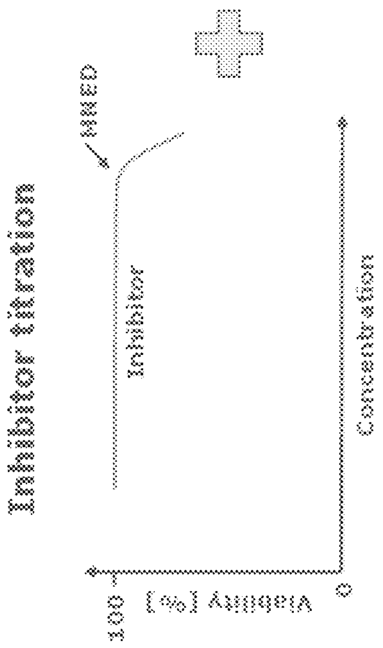
FIG. 24 is an inhibitor titration graph.
Figure 25:
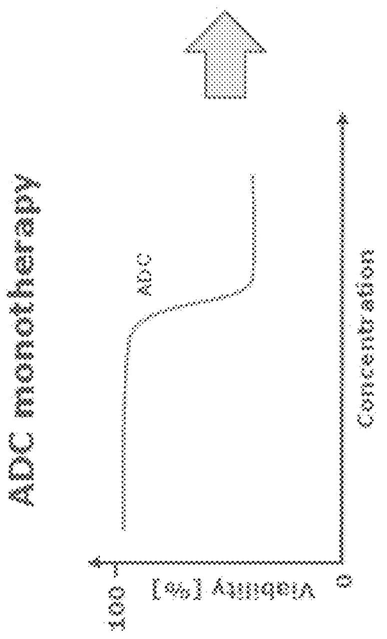
FIG. 25 is an ADC monotherapy graph.
Figure 26:
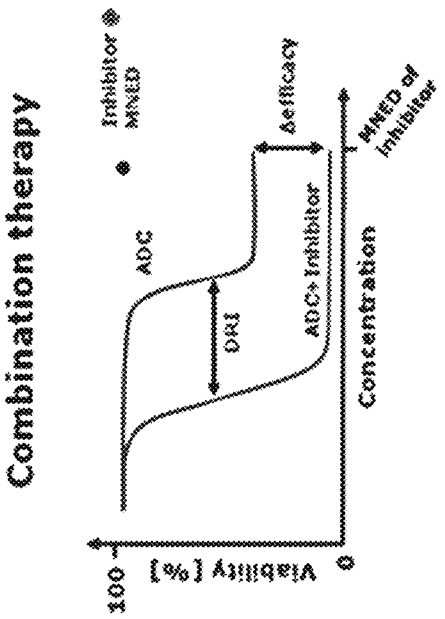
FIG. 26 is a combination therapy graph.

FIG. 23 shows several examples of duocarmycins.

Pools of siRNA agains CHK1 (CHEK1), ATR, PLK1 and a non-targeting siRNA was purchased from Dharmacon with the following sequences:

```
siGENOME Human CHEK1 (1111) SMARTpool siRNA:
                                        (SEQ ID NO: 1)
GCAACAGUAUUUCGGUAUA

                                        (SEQ ID NO: 2)
GGACUUCUCUCCAGUAAAC

                                        (SEQ ID NO: 3)
AAAGAUAGAUGGUACAACA

                                        (SEQ ID NO: 4)
AGAUAUGAAGCGUGCCGUA

ON-TARGETplus Human ATR (545) SMARTpool siRNA:
                                        (SEQ ID NO: 5)
GAGAAAGGAUUGUAGACUA

                                        (SEQ ID NO: 6)
GCAACUCGCCUAACAGAUA

                                        (SEQ ID NO: 7)
CCACGAAUGUUAACUCUAU

                                        (SEQ ID NO: 8)
CCGCUAAUCUUCUAACAUU

ON-TARGETplus Human PLK1 (5347) SMARTpool siRNA:
                                        (SEQ ID NO: 9)
GCACAUACCGCCUGAGUCU

                                       (SEQ ID NO: 10)
CCACCAAGGUUUUCGAUUG

                                       (SEQ ID NO: 11)
GCUCUUCAAUGACUCAACA

                                       (SEQ ID NO: 12)
UCUCAAGGCCUCCUAAUAG

siGenome Non-Targeting siRNA Pool #1:
                                       (SEQ ID NO: 13)
UAGCGACUAAACACAUCAA

                                       (SEQ ID NO: 32)
UAAGGCUAUGAAGAGAUAC

                                       (SEQ ID NO: 33)
AUGUAUUGGCCUGUAUUAG

                                       (SEQ ID NO: 16)
AUGAACGUGAAUUGCUCAA
```

The antibodies used in the present invention have the following amino acid sequences a) Amino acid sequence of αHER2 antibody as published by drug bank accession entry DB00072 in the year 2009. Genetic modifications are marked in bold font.

Heavy chain:
(SEQ ID NO: 17)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWGG

DGFYAMDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTYI

CNVNHKPSNTKVDKKVEPPKSCDKTHTCPPCPAPELLGGPSVFLFPPKPK

-continued

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

Light Chain with SrtA recognition motif:
(SEQ ID NO: 18)
MKLPVRLLVLMFWIPASLSDIQMTQSPSSLSASVGDRVTITCRASQDVNTA

VAWYQQKPGKAPKLLIYSASFLYSGVPSRFSGSRSGTDFTLTISSLQPEDF

ATYYCQQHYTTPPTFGQGTKVEIKRTVAAPSVFIFPPSDEQLKSGTASVVC

LLNNFYPREAKVQWKVDNALQSGNSQESVTEQDSKDSTYSLSSTLTLSKAD

YEKHKVYACEVTHQGLSSPVTKSFNRGECGGGGSGGGGSGGGGSLPETGS b) Amino acid sequence of αEGFR antibody Cetuximab. Genetic modifications are marked in bold font.

Native heavy chain:
(SEQ ID NO: 19)
QVQLKQSGPGLVQPSQSLSITCTVSGFSLTNYGVHWVRQSPGKGLEWLG

VIWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

Heavy chain with SrtA recognition motif
(SEQ ID NO: 20)
QVQLKQSGPGLVQPSQSLSITCTVSGFSLTNYGVHWVRQSPGKGLEWLG

VIWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGKLPE

TGS

Light chain with spacer and SrtA recognition motif:
(SEQ ID NO: 21)
DILLTQSPVILSVSPGERVSFSCRASQSIGTNIHWYQQRTNGSPRLLIKYA

SESISGIPSRFSGSGSGTDFTLSINSVESEDIADYYCQQNNNWPTTFGAGT

KLELKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGECGGGGSGGGGSGGGGSLPETGS

Light chain with SrtA recognition motif:
(SEQ ID NO: 22)
DILLTQSPVILSVSPGERVSFSCRASQSIGTNIHWYQQRTNGSPRLLIKYA
SESISGIPSRFSGSGSGTDFTLSINSVESEDIADYYCQQNNNWPTTFGAGT
KLELKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGECLPETGS c) Amino acid sequence of αHEL antibody. Genetic modifications are marked in bold font.

Light chain with spacer and SrtA recognition motif:
(SEQ ID NO: 23)
DIQMTQSPSSLSASVGDRVTITCRASGNIHNYLAWYQQKPGKAPKLLIYYT
TTLADGVPSRFSGSGSGTDYTFTISSLQPEDIATYYCQHFWSTPRTFGQGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGECGGGGSGGGGSGGGGSLPETGS

Native heavy chain:
(SEQ ID NO: 24)
QVQLQESGPGLVRPSQTLSLTCTVSGFSLTGYGVNWVRQPPGRGLEWIG
MIWGDGNTDYNSALKSRVTMLKDTSKNQFSLRLSSVTAADTAVYYCARER
DYRLDYWGQGSLVTVSSASTKGPSVFPLAPSSKSTSGGTAALGCLVKDYF
PEPVTVSWNSGALTSGVHTFPAVLQSSGLYSLSSVVTVPSSSLGTQTYICN
VNHKPSNTKVDKRVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK d) Amino acid sequence of αMET×EGFR antibody. Genetic modifications are marked in bold font.

SEED GA heavy chain with scFv:
(SEQ ID NO: 25)
DIQMTQSPSSLSASVGDRVTITCRASQSIGTNIHWYQQKPGKAPKLLIKYA
SESISGVPSRFSGSGYGTDFTLTISSLQPEDVATYYCQQNYNWPTTFGQGT
KVEIKGGGGSGGGGSGGGGSGGGGSEVQLVQSGAEVKKPGASVKVSCKA
SGFSLTNYGVHWMRQAPGQGLEWIGVIWSGGNTDYNTPFTSRVTITSDKS
TSTAYMELSSLRSEDTAVYYCARALTYYDYEFAYWGQGTLVTVSS SEED AG heavy chain:
(SEQ ID NO: 26)
METDTLLLWVLLLWVPGSTGEVQLVQSGGGLVQPGGSLRLSCAASGFTFS
SYAMSWVRQAPGKGLEWVSAISGSGGSTYY
ADSVKGRFTISRDNSKNTLYLQMNSLRAEDTAVYYCAKDRRITHTYWGQG
TLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVD
KRVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQD
WLNGKEYKCKVSNKALPAPIEKTISKAKGQPFRPEVHLLPPSREEMTKNQV
SLTCLARGFYPKDIAVEWESNGQPENNYKTTPSRQEPSQGTTTFAVTSKLT
VDKSRWQQGNVFSCSVMHEALHNHYTQKTISLSPGK Light chain with SrtA recognition motif:
(SEQ ID NO: 27)
METDTLLLWVLLLWVPGSTGEPVLTQPPSVSVAPGETATIPCGGDSLGSKI
VHWYQQRPGQAPLLVVYDDAARPSGIPERFSGSKSGTTATLTISSVEAGDE
ADYFCQVYDYHSDVEVFGGGTKLTVLGQPKAAPSVTLFPPSSEELQANKA
TLVCLISDFYPGAVTVAWKADSSPVKAGVETTTPSKQSNNKYAASSYLSLT
PEQWKSHKSYSCQVTHEGSTVEKTVAPTECSLPETGS e) Amino acid sequence of αMET antibody. Genetic modifications are marked in bold font.

Light chain with SrtA recognition motif:
(SEQ ID NO: 28)
METDTLLLWVLLLWVPGSTGEPVLTQPPSVSVAPGETATIPCGGDSLGSKI
VHWYQQRPGQAPLLVVYDDAARPSGIPERFSGSKSGTTATLTISSVEAGDE
ADYFCQVYDYHSDVEVFGGGTKLTVLGQPKAAPSVTLFPPSSEELQANKA
TLVCLISDFYPGAVTVAWKADSSPVKAGVETTTPSKQSNNKYAASSYLSLT
PEQWKSHKSYSCQVTHEGSTVEKTVAPTECSLPETGS

Heavy chain:
(SEQ ID NO: 29)
EVQLVQSGGGLVQPGGSLRLSCAASGFTFSSYAMSWVRQAPGKGLEWVS
AISGSGGSTYYADSVKGRFTISRDNSKNTLYLQMNSLRAEDTAVYYCAKDR
RITHTYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICNV
NHKPSNTKVDKRVEPKSCDKTHTCPPCPAPELLGGPSVFLFPPKPKDTLMI
SRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSF
FLYSKLTVDKSRWQQGNVFSCSVMHEALHNHYTQKSLSLSPGK TABLE 1
| Pharmaceutical active compounds used in the present invention | | |
|---|---|---|
| Name | No. | Structure |
| ATRi 1 | 1 | 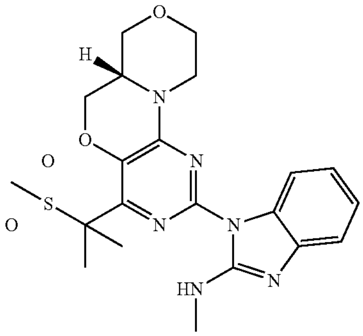 |
| AZ20 | 2 | 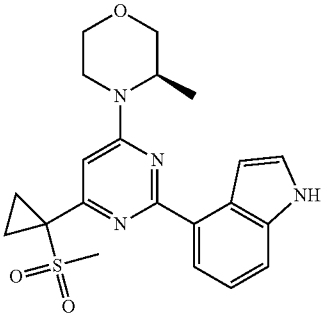 [SMILES: C[C@@H]1COCCN1c1cc(C2(S(C)(=O)=O)CC2)nc(-c2cccc3[nH]ccc23)n1] |
| AZD6738 | 3 | 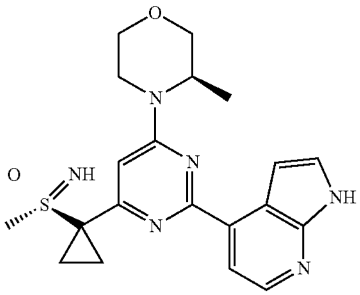 |
| BAY1895344 | 4 | 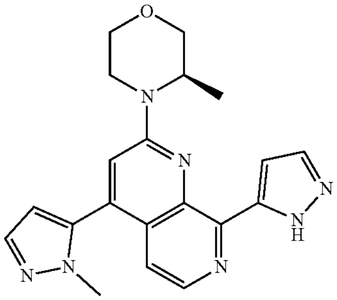 [SMILES: C[C@@H]1COCCN1c1cc(-c2ccnn2C)c2ccnc(-c3ccn[nH]3)c2n1] |
| BAY286 | 5 | 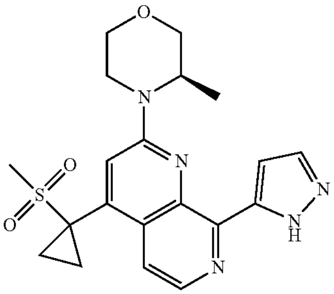 [SMILES: C[C@@H]1COCCN1c1cc(C2(S(C)(=O)=O)CC2)c2ccnc(-c3ccn[nH]3)c2n1] |

TABLE 1-continued
| Pharmaceutical active compounds used in the present invention | | |
|---|---|---|
| Name | No. | Structure |
| BAY73 | 6 | 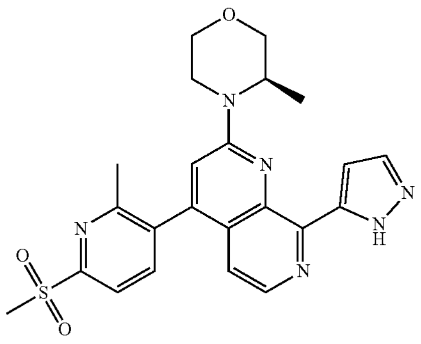 [SMILES: Cc1nc(S(C)(=O)=O)ccc1-c1cc(N2CCOC[C@H]2C)nc2c(-c3ccn[nH]3)nccc12] |
| VE-822 (VX-970, M6620 Berzosertib) | 7 | 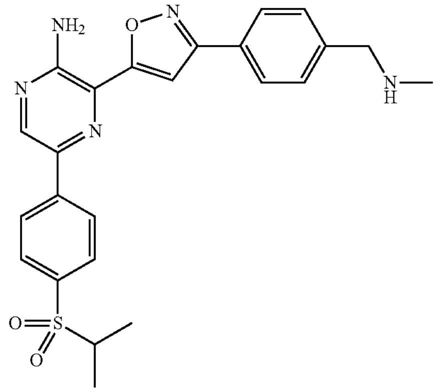 [SMILES: CNCc1ccc(-c2cc(-c3nc(-c4ccc(S(=O)(=O)C(C)C)cc4)cnc3N)on2)cc1] |
| | 13 | 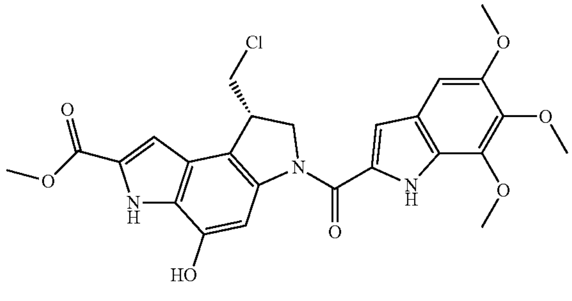 |
| | 24 | 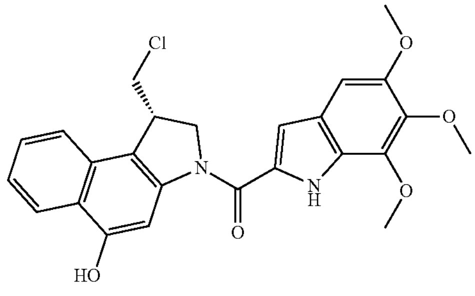 [SMILES: COc1cc2cc(C(=O)N3C[C@@H](CCl)c4c3cc(O)c3ccccc43)[nH]c2c(OC)c1OC] |

TABLE 1-continued
| Pharmaceutical active compounds used in the present invention | | |
|---|---|---|
| Name | No. | Structure |
| | 29 | 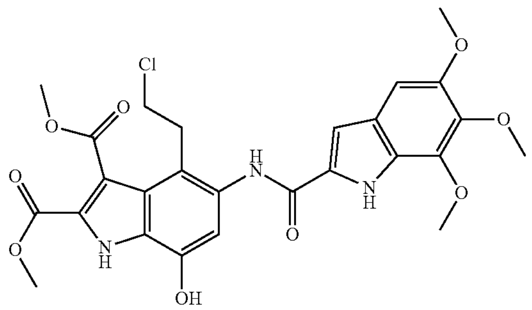 [SMILES: COC(=O)c1[nH]c2c(O)cc(NC(=O)c3cc4cc(OC)c(OC)c(OC)c4[nH]3)c(CCCl)c2c1C(=O)OC] |
| | 30 | 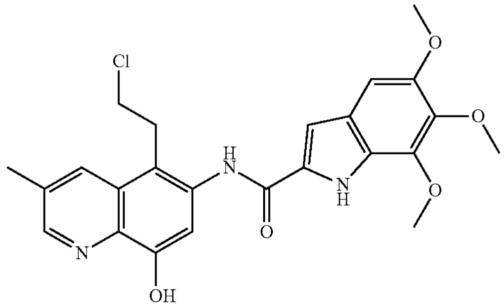 |
| | 31 | 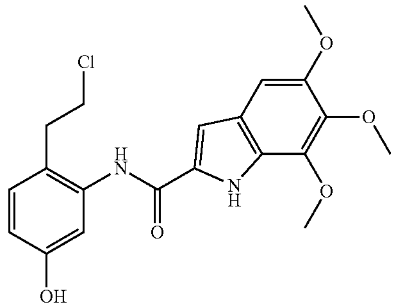 [SMILES: COc1cc2cc(C(=O)Nc3cc(O)ccc3CCCl)[nH]c2c(OC)c1OC] |
| | 32 | 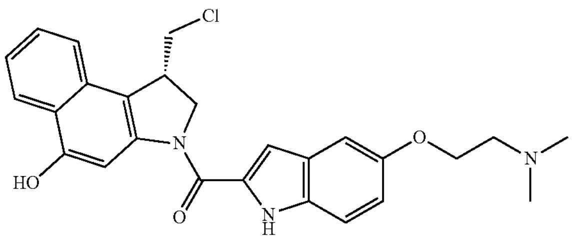 [SMILES: CN(C)CCOc1ccc2[nH]c(C(=O)N3C[C@@H](CCl)c4c3cc(O)c3ccccc43)cc2c1] |
| | 33 | 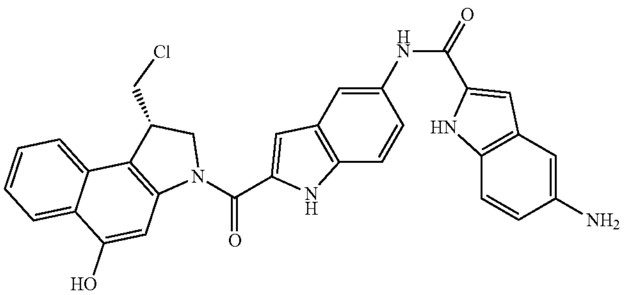 [SMILES: Nc1ccc2[nH]c(C(=O)Nc3ccc4[nH]c(C(=O)N5C[C@@H](CCl)c6c5cc(O)c5ccccc65)cc4c3)cc2c1] |

TABLE 1-continued
| Pharmaceutical active compounds used in the present invention | | |
|---|---|---|
| Name | No. | Structure |
| | 34 | 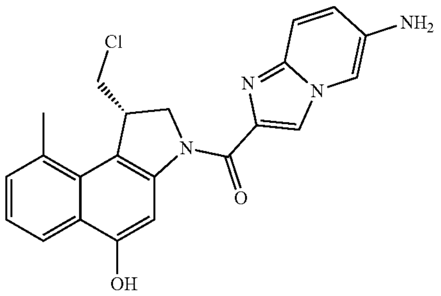 [SMILES: Cc1cccc2c(O)cc3c(c12)[C@H](CCl)CN3C(=O)c1cn2cc(N)ccc2n1] |
| | 10 | 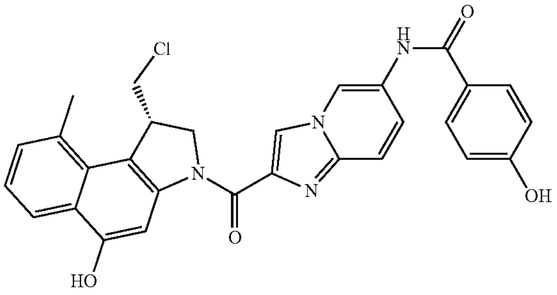 [SMILES: Cc1cccc2c(O)cc3c(c12)[C@H](CCl)CN3C(=O)c1cn2cc(NC(=O)c3ccc(O)cc3)ccc2n1] |
| KU-55933 | | 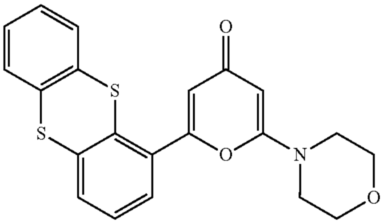 [SMILES: O=c1cc(-c2cccc3c2Sc2ccccc2S3)oc(N2CCOCC2)c1] |
| NU7441 | | 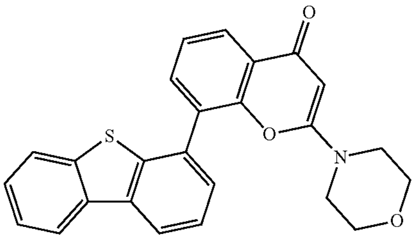 [SMILES: O=c1cc(N2CCOCC2)oc2c(-c3cccc4c3sc3ccccc34)cccc12] |
| AZD7762 | | 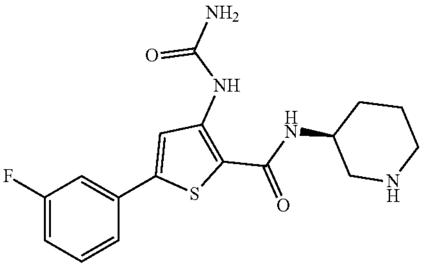 [SMILES: NC(=O)Nc1cc(-c2cccc(F)c2)sc1C(=O)N[C@H]1CCCNC1] |

TABLE 1-continued
| Pharmaceutical active compounds used in the present invention | | |
|---|---|---|
| Name | No. | Structure |
| LY2603618 | | 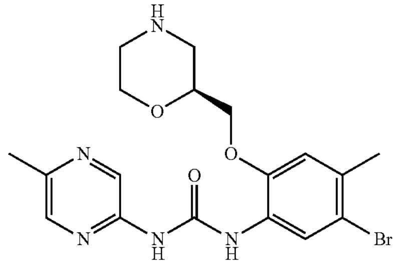 [SMILES: Cc1cnc(NC(=O)Nc2cc(Br)c(C)cc2OC[C@@H]2CNCCO2)cn1] |
| Amuvatinib | | 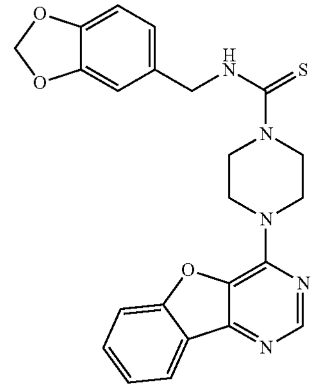 [SMILES: S=C(NCc1ccc2c(c1)OCO2)N1CCN(c2ncnc3c2oc2ccccc23)CC1] |
| AZD1775 | | 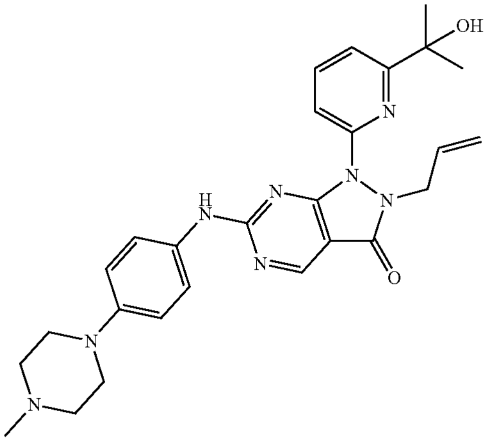 [SMILES: C=CCn1c(=O)c2cnc(Nc3ccc(N4CCN(C)CC4)cc3)nc2n1-c1cccc(C(C)(C)O)n1] |
| Bleomycin A5 | | 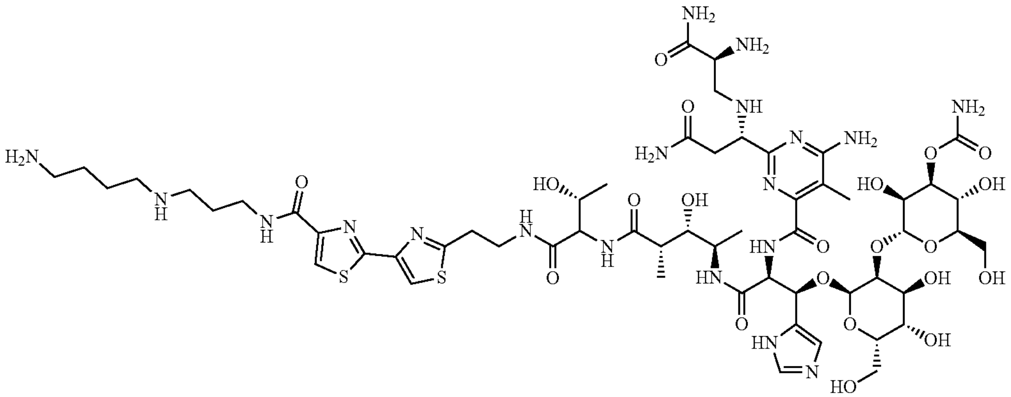 [SMILES: Cc1c(N)nc([C@H](CC(N)=O)NC[C@H](N)C(N)=O)nc1C(=O)N[C@H](C(=O)N[C@H](C)[C@@H](O)[C@H](C)C(=O)NC(C(=O)NCCc1nc(-c2nc(C(=O)NCCCNCCCCN)cs2)cs1)[C@@H](C)O)[C@@H](O[C@@H]1O[C@@H](CO)[C@@H](O)[C@H](O)[C@@H]1O[C@H]1O[C@H](CO)[C@@H](O)[C@H](OC(N)=O)[C@@H]1O)c1cnc[nH]1] |

TABLE 1-continued
| Name | No. | Structure |
|---|---|---|
| Pharmaceutical active compounds used in the present invention | | |
| Ciliobrevin D | | 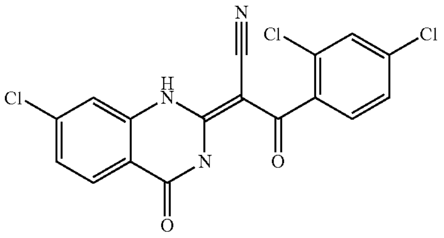 [SMILES: N#C/C(C(=O)c1ccc(Cl)cc1Cl)=C1/NC(=O)c2ccc(Cl)cc2N1] |
| Cmpd31 | | 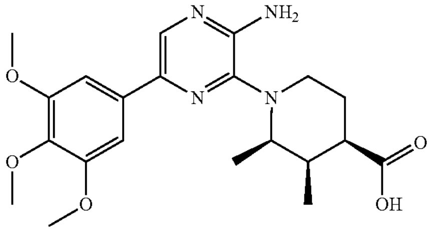 [SMILES: COc1cc(-c2cnc(N)c(N3CC[C@@H](C(=O)O)[C@@H](C)[C@H]3C)n2)cc(OC)c1OC] |
| CP724714 | | 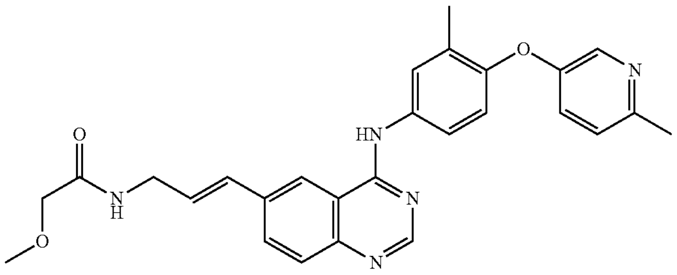 |
| Etoposide | | 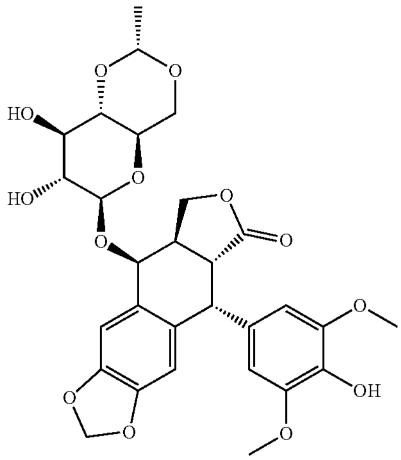 [SMILES: COc1cc([C@@H]2c3cc4c(cc3[C@@H](O[C@@H]3O[C@@H]5CO[C@@H](C)O[C@H]5[C@H](O)[C@H]3O)[C@H]3COC(=O)[C@H]23)OCO4)cc(OC)c1O] |
| Hycanthone | | 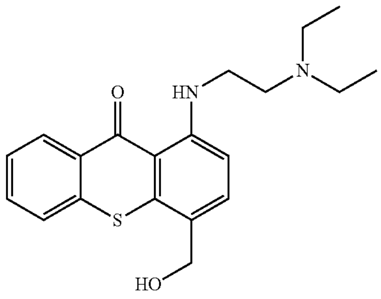 [SMILES: CCN(CC)CCNc1ccc(CO)c2sc3ccccc3c(=O)c12] |

TABLE 1-continued
| Pharmaceutical active compounds used in the present invention | | |
|---|---|---|
| Name | No. | Structure |
| Lapatinib | | 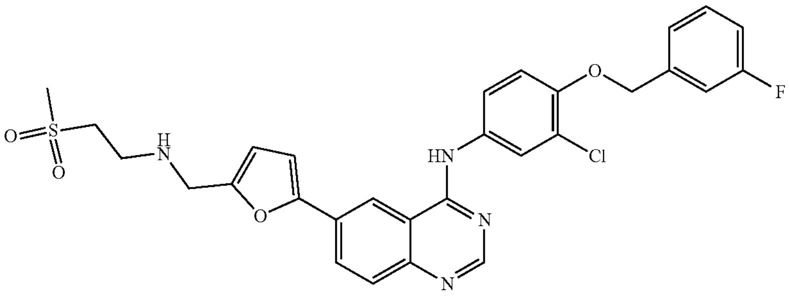 [SMILES: CS(=O)(=O)CCNCc1ccc(-c2ccc3ncnc(Nc4ccc(OCc5cccc(F)c5)c(Cl)c4)c3c2)o1] |
| Olaparib | | 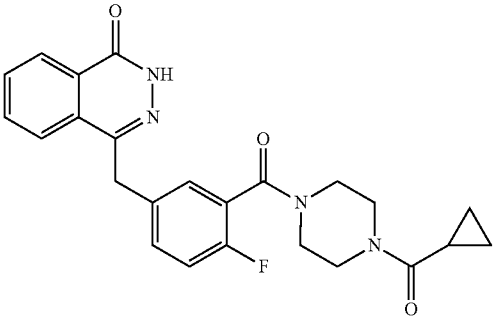 [SMILES: O=C(c1cc(Cc2n[nH]c(=O)c3ccccc23)ccc1F)N1CCN(C(=O)C2CC2)CC1] |
| Tranespimycin | | 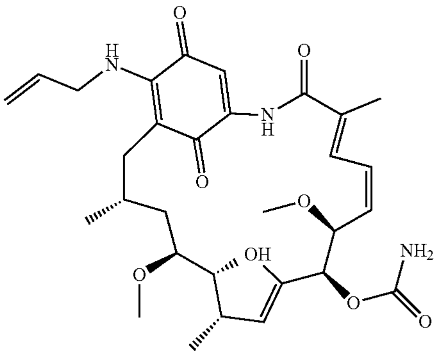 [SMILES: C=CCNC1=C2C[C@@H](C)C[C@H](OC)[C@H](C)[C@@H](C)/C=C(\O)[C@H](OC(N)=O)[C@@H](OC)/C=C\C=C(/C)C(=O)NC(=CC1=O)C2=O] |
| TH588 | | 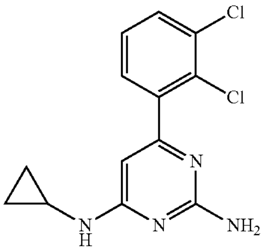 [SMILES: Nc1nc(NC2CC2)cc(-c2cccc(Cl)c2Cl)n1] |
| Gemcitabine | | 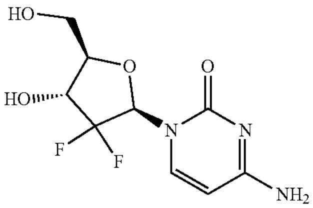 [SMILES: Nc1ccn([C@@H]2O[C@H](CO)[C@@H](O)C2(F)F)c(=O)n1] |

TABLE 1-continued
| Pharmaceutical active compounds used in the present invention | | |
|---|---|---|
| Name | No. | Structure |
| SN-38 | | 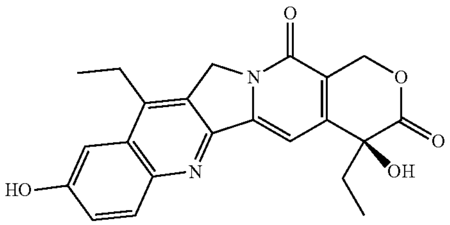 [SMILES: CCc1c2c(nc3ccc(O)cc13)-c1cc3c(c(=O)n1C2)COC(=O)[C@]3(O)CC] |
| MMAE | | 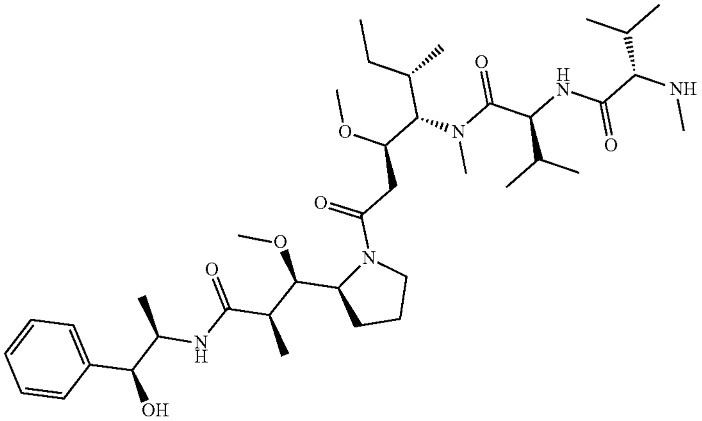 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C] |
| LD-1 | | 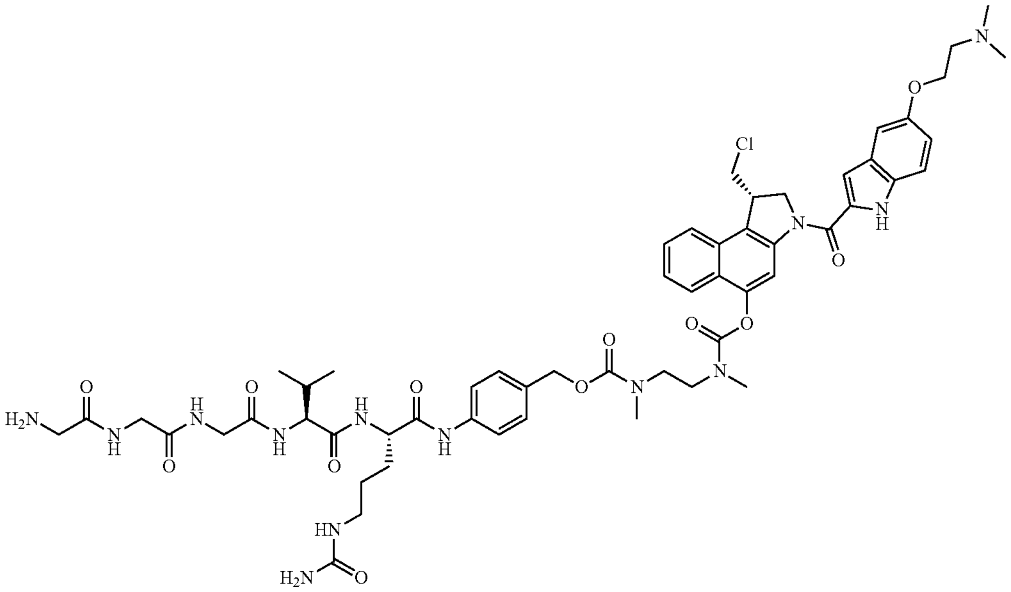 [SMILES: CC(C)[C@H](NC(=O)CNC(=O)CNC(=O)CN)C(=O)N[C@@H](CCCNC(N)=O)C(=O)Nc1ccc(COC(=O)N(C)CCN(C)C(=O)Oc2cc3c(c4ccccc24)[C@H](CCl)CN3C(=O)c2cc3cc(OCCN(C)C)ccc3[nH]2)cc1] |

TABLE 1-continued
| Pharmaceutical active compounds used in the present invention | | |
|---|---|---|
| Name | No. | Structure |
| LD-2 | | 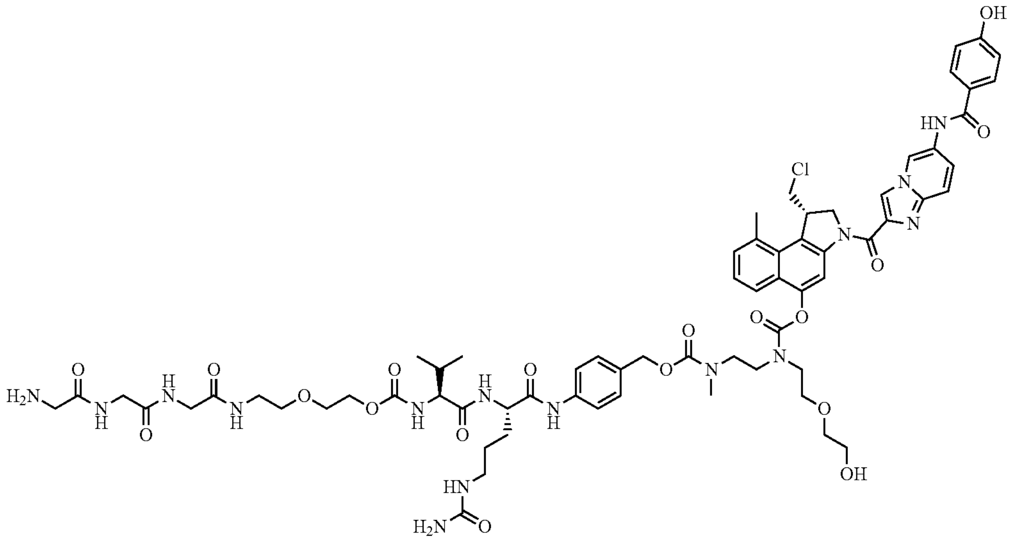 [SMILES: Cc1cccc2c(OC(=O)N(CCOCCO)CCN(C)C(=O)OCc3ccc(NC(=O)[C@H](CCCNC(N)=O)NC(=O)[C@@H](NC(=O)OCCOCCNC(=O)CNC(=O)CNC(=O)CN)C(C)C)cc3)cc3c(c12)[C@H](CCl)CN3C(=O)c1cn2cc(NC(=O)c3ccc(O)cc3)ccc2n1] |
| LD-3 | | 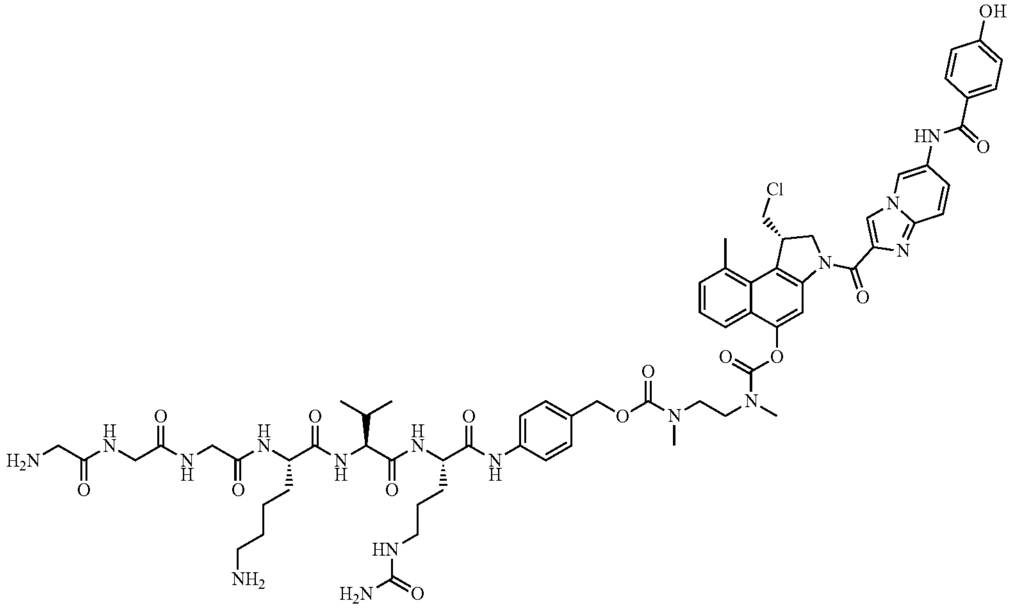 [SMILES: Cc1cccc2c(OC(=O)N(C)CCN(C)C(=O)OCc3ccc(NC(=O)[C@H](CCCNC(N)=O)NC(=O)[C@@H](NC(=O)[C@H](CCCCN)NC(=O)CNC(=O)CNC(=O)CN)C(C)C)cc3)cc3c(c12)[C@H](CCl)CN3C(=O)c1cn2cc(NC(=O)c3ccc(O)cc3)ccc2n1] |

TABLE 1-continued
| Pharmaceutical active compounds used in the present invention | | |
|---|---|---|
| Name | No. | Structure |
| LD-4 | | 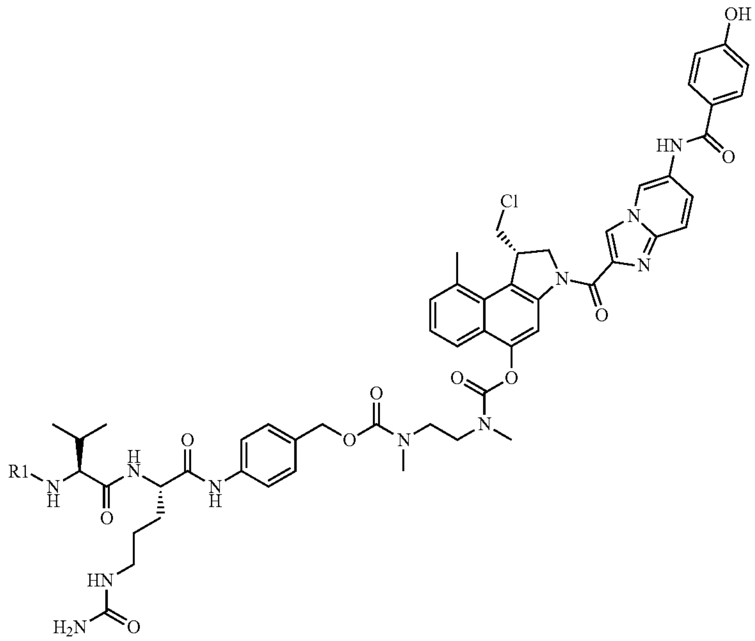 |
| LD-5 | | 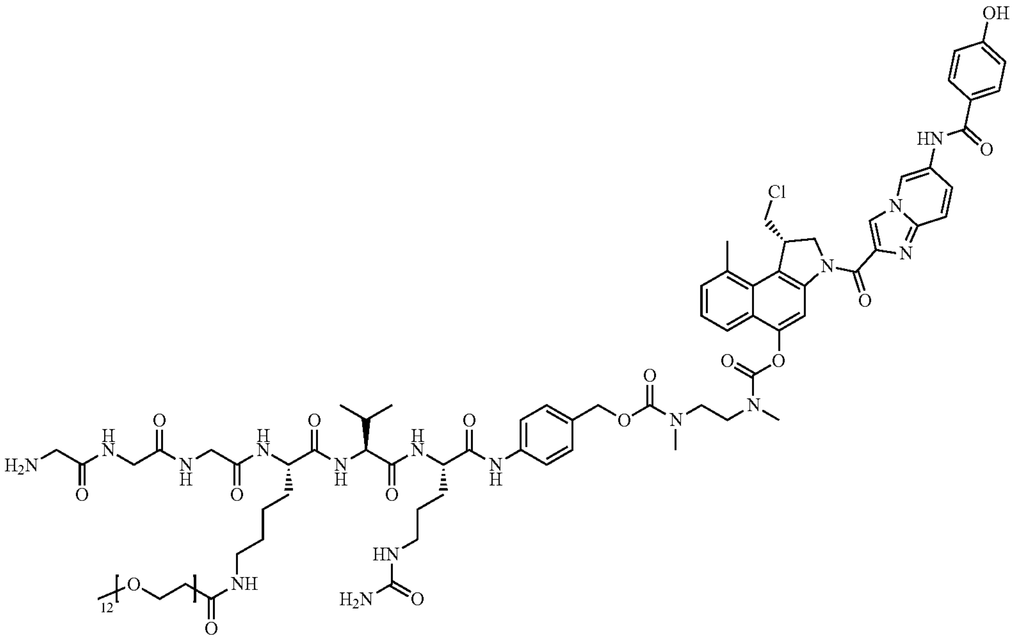 |

TABLE 1-continued
| Pharmaceutical active compounds used in the present invention | | |
|---|---|---|
| Name | No. | Structure |
| LD-6 | | 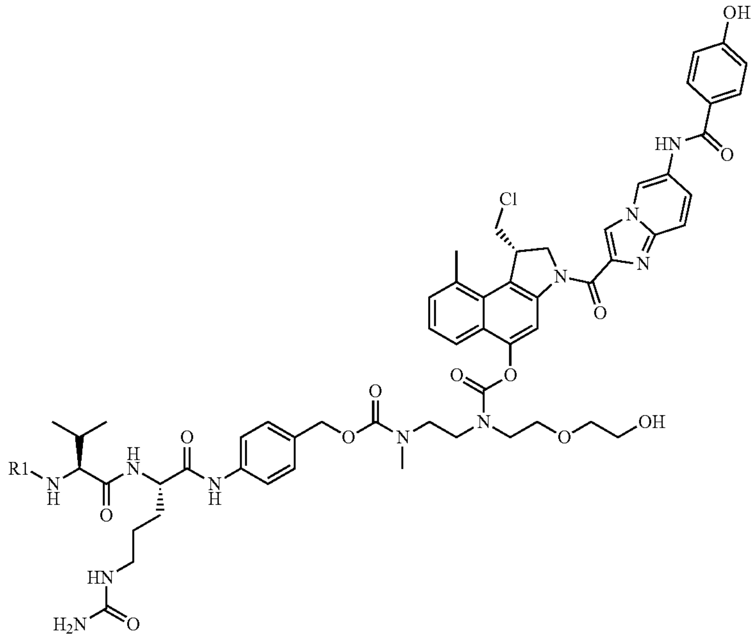 |
| LD-7 | | 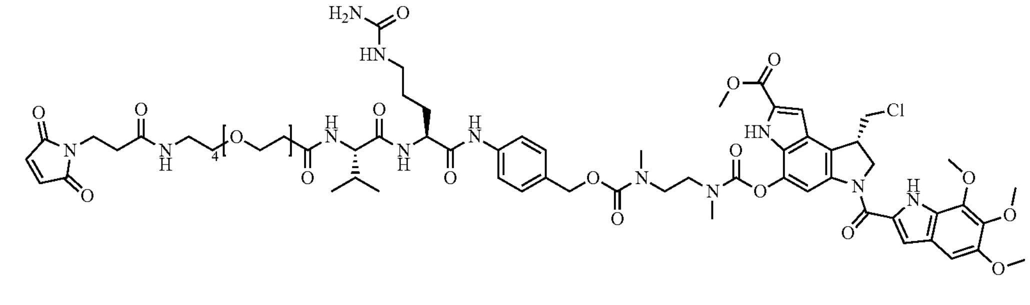 |
| LD-8 | | 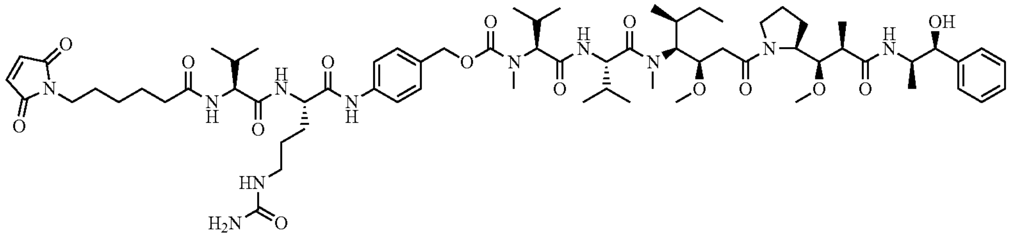 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C] |

TABLE 1-continued

| Pharmaceutical active compounds used in the present invention | | |
|---|---|---|
| Name | No. | Structure |
| LD-9 | | 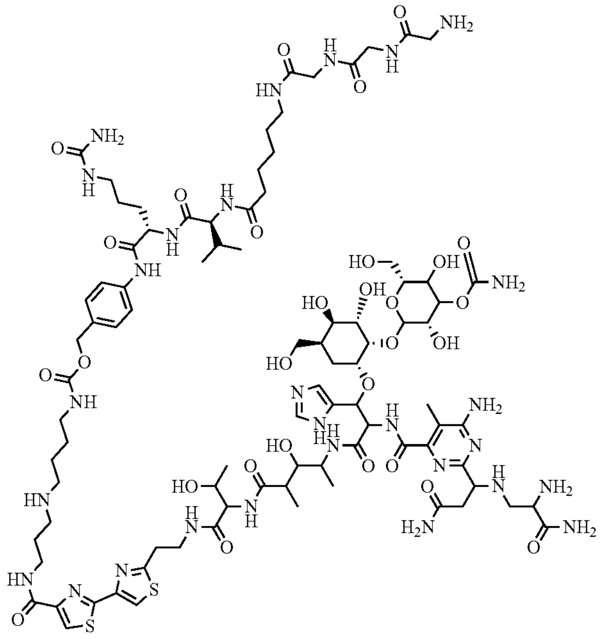 [SMILES: Cc1c(N)nc(C(CC(N)=O)NCC(N)C(N)=O)nc1C(=O)NC(C(=O)NC(C)C(O)C(C)C(=O)NC(C(=O)NCCc1nc(-c2nc(C(=O)NCCCNCCCCNC(=O)OCc3ccc(NC(=O)[C@H](CCCNC(N)=O)NC(=O)[C@@H](NC(=O)CCCCCNC(=O)CNC(=O)CNC(=O)CN)C(C)C)cc3)cs2)cs1)C(C)O)C(O[C@@H]1C[C@@H](CO)[C@@H](O)[C@H](O)[C@@H]1OC1O[C@H](CO)C(O)C(OC(N)=O)[C@@H]1O)c1cnc[nH]1] |

In the following methods are described which were used in the context of research that led to the present invention. In general, these methods are well known in the art, and presented here for the sake of completeness.

a) Antibody Expression

The expression of antibodies is based on the protocol supplied for ExpiFectamine™ 293 Transfection Kit (Life Technologies Corp.). 1250 μL Opti-MEM are mixed with 80 μL Expifectamine and incubate for max. 5 min. Afterwards 12.5 μg of heavy and light chain plasmid are diluted in 1250 μL Opti-MEM. SEED-antibodies carry two different heavy chains. Heavy chain plasmid for GA- and AG-strand and light chain, are mixed in the mass-ratio 1:1:1. Both solutions are united, forming reaction mixture, and incubated for 30 min. Meanwhile cell density of Expi293™ cells is determined using ViCell cell counter (Beckman Coulter). The cells were used if the viability is greater than 95%. Cells are diluted to $3.0\times10^6$ cells $mL^{-1}$ in Expi293™ Expression Medium to a total volume of 21 mL, which was tempered at 37° C. The reaction mixture is added to the cell suspension while shaking. The cells are shaken at 37° C. and 5% C02. After 16-18 h 150 μL Enhancer 1 and 1.5 mL Enhancer 2 are added. The expression took place while shaking at 37° C. and 5% C02 for four days. The antibodies are isolated by collecting the supernatant after centrifugation (6000 g/10 min/4° C.). The supernatant is filtered sterilely using Steritop 0.22 μm or Steriflip 0.22 μm filters (Merck Millipore, Merck KGaA). Antibodies are purified by proceeding with Protein A chromatography. This procedure can be scaled-up by keeping the ratios of reagents equal.

b) Transformation

Transformations were performed using 50 μL chemically competent cells, which were thawed on ice and subsequently mixed with 50 ng plasmid solution. After 30 minutes incubation on ice, the cells were tempered for 30 seconds at 42° C. Afterwards 250 μL SOC-medium were added, followed by 45 minutes of incubation at 37° C. while shaking. The cell suspension was centrifuged for 1 min at 16 krcf. The supernatant was discarded, whereas the cells were resuspended in the remaining solution. The suspension was plated on agar-plates, containing antibiotic. The plates were incubated overnight at 37° C.

c) Plasmid Amplification

Plasmids were amplified by transformation of One Shot TOP 0 Chemically Competent *E. coli*. The purification was performed using JetStar™ 2.0 Plasmid Purification Kit if high plasmid yield is needed for protein expression. The purification procedure began with harvesting of the overnight culture. The cells were lysed, followed by precipitation and centrifugation. The supernatant is applied on a prepacked anion exchange column. Since the deoxyribonucleic acid (DNA) backbone is negatively charged, the DNA is bound by the positively charged column matrix. A low salt washing step removes ribonucleic acid (RNA), carbohydrates and proteins. DNA was then eluted under high salt conditions. By precipitation of DNA using alcohol, the DNA was desalted. For the amplification of plasmid for sequencing purposes QIAPrep Spin Miniprep Kit was used. The purification procedure is comparable to JetStar™ 2.0 Plasmid Purification Kit procedure, but DNA is adsorbed to the silica membrane of QiaPrep columns at high salt concentrations and eluted at low salt concentrations.

d) ADC Generation and Purification

The conjugation of linker-drugs can be achieved using several techniques.

Some of these techniques require prior modification of the antibody. The antibody formats used are depicted in FIG. 1. Formats A, B and C are designed for enzymatic modification using sortase A. In the case of format A and B, a conventional IgG molecule is elongated C-terminally by a (G4S)

3-spacer and the sortase A recognition sequence LPETGS or by the sortase A recognition sequence LPETGS only. Format C is a bispecific antibody-format generated using the strand-exchange engineered domain (SEED) technology. This allows to combine a scFv and a Fab portion that bind to different antigens. Additionally, the Fab is elongated C-terminally by the sortase A recognition motif LPETGS. Format D enables the production of ADCs with up to four drugs per mAb. Therefore LCs contain (G4S)3-spacer and the sortase A recognition sequence LPETGS and the HCs are extended C-terminally by the SrtA recognition motif LPETGS. For the conjugation of maleimide containing linker-drugs native mAbs (format E) can be utilized.

Several purification methods were used. After conjugation of the mAb using either thiol coupling or enzymatic conjugation via SrtA, the crude ADC mixture needs to be purified to deplete excess linker-drug, conjugation reagents or enzymes. A convenient strategy is the purification via preparative SEC, which directly yields a purified ADC. The use of Protein A chromatography always implies additional purification step that exchange the buffer to ensure ADC storage in an appropriate buffer. Therefore, Protein A chromatography is followed by desalting. However, this method further dilutes the sample, which might require a concentration step. Another route uses Protein A chromatography, followed by desalting. If aggregates are present, preparative SEC can be used to deplete high molecular species. Due to dilution of the sample, concentration yields the purified ADC.

e) Sortase A-Mediated Conjugation Reaction

The reaction is carried out using 10 equivalents of oligo-glycine cytotoxic substrate per SrtA recognition motif of the antibody. 0.37 equivalents Sortase A are applied compared to antibody. Sortase A has a binding site for calcium ions. The binding of calcium ions slows the motion of Sortase A, thereby allowing the binding of the substrate to Sortase A. This leads to an eightfold increase in activity.

13.5 μM (1 eq) antibody construct
5 mM (375 eq) CaCl2
133 μM (10 eq) oligo-glycine substrate per SrtA recognition motif.
5 μM (0.37 eq) eSrtA The reagents and buffer are mixed in the described manner. The reaction mixture is diluted with reaction buffer to adjust the given concentrations. The reaction is performed by incubation of the mixture at 22° C. for 30 minutes. The addition of SrtA marks the start of reaction. The reaction is stopped by addition of 750 eq EDTA, which removes free calcium ions from the solution by forming a complex. The final concentration of antibody in solution is adjusted to 13.5 μM by addition of a sufficient amount of buffer.

f) Protein a Chromatography

The basis for the purification of IgG antibodies is the high binding affinity of *Staphylococcus aureus* protein A to the Fc region of IgG-type antibodies. The binding between protein A and IgG antibodies takes place at physiological pH and ionic strength, whereas the binding is disrupted at low pH resulting in elution of the antibody. It was shown, that IgG molecules usually elute at pH 3.0.

Antibody purification: Preparative protein A-affinity chromatography was performed on ÄKTAXpress (GE Healthcare) chromatography system using HiTrap™ 1 mL of 5 mL Protein A HP column (GE Healthcare). Upon binding of the antibody to the column, it was washed with binding buffer. Afterwards elution was performed in one step by washing the column with 100% elution buffer. The antibody was eluted in 1.5 mL fractions onto 100 μL neutralizing buffer into a 96-deepwell plate. The fractions were analyzed using SDS-PAGE regarding purity and pooled accordingly.

ADC purification: ADCs were purified as described before, but on an AKTA Purifier (GE Healthcare) chromatography system using HiTrap™ 1 mL 5 mL Protein A HP column (GE Healthcare). The sample was applied on the column using an autosampler by SunChrom. Fractions of 1 mL were eluted into 1.5 mL tubes containing 100 μL neutralization buffer. ADC containing fractions were pooled.

g) Preparative SEC

The separation principle of SEC is based on differences in elution time of analytes caused by differences in their size. The stationary phase of the SEC column is composed of spherical particles, which have pores. Small molecules can diffuse into the pores, while larger molecules cannot enter the pores and pass through the matrix directly. This leads to an elution of the largest molecules first, followed by smaller molecules in the order of their size. In the course of this work SEC was used to remove aggregates from antibody preparations, as well as to separate ADCs from conjugation reagents such as enzyme Sortase A and toxin excess. SEC purification was carried out on a Agilent 1260 HPLC system (Agilent Technologies). The flow rate was 0.5 mL min 1 and the samples were separated using a Superdex 200 10/30 increase column (GE Healthcare). Samples were eluted in 0.5 mL fractions and pooled to yield the final product. Preparative SEC for the preparation of αHER2-1 purified via route D was performed on ÄKTAXpress (GE Healthcare) chromatography system using HiLoad™ 16/600 Superdex™ 200 μg column. Therefore the column was washed with water with subsequent equilibration with the mobile phase. After injection, the sample was eluted isocratically at a flow rate of 1 mL $min^{-1}$ and peaks are collected fractionating.

h) Analytical HIC

The drug-to-antibody ratio (DAR) of an ADC can be determined using hydrophobic interaction chromatography (HIC). Therefore, proteins are applied in an aqueous mobile phase containing high concentration of chaotropic salt. The individual proteins bind to the stationary phase based on their hydrophobicity and are eluted by gradual reduction of salt content in the order of least to most hydrophobic.[123] The different ADC species and unreacted mAb are separated based on the drug-load. The weighted area-under-curve of the chromatogram can be used to calculate the DAR of the ADC.

All samples were prepared by dilution to a final concentration of 1.5 M ammonium sulfate using sample preparation buffer. Analytical HIC of Sortase A-generated ADCs was performed using HPLC-system (Agilent Technologies) which was equipped with MAB PAK Butyl, 4.6×50 mm column (Thermo Scientific). The UV-VIS detector used wavelengths 220 nm and 280 nm. Measurements were performed at a flow rate of 1 mL $min^{-1}$ applying a gradient of 0 to 100% buffer B in 20 min. The HPLC-runs were performed at 30° C. The column was washed subsequently with 100% buffer B. Data were processed using ChemStation of LC 3D systems (Agilent Technologies).

i) Analytical SEC

The monomeric content of mAb and ADC samples was determined by analytical SEC. It was performed on Infinity 1260 HPLC system by Agilent Technologies with a TSK-GEL Super SW 3000 SEC 4.6×300 mm column. Elution was performed isocratically at a flow rate of 0.35 mL $min^{-1}$.

j) Buffer Change

The change of buffer is performed using PD-10 Desalting Columns (GE Healthcare), which contain Sephadex G-25

Medium. The underlying chromatography method is size exclusion chromatography, where the sample is separated based on the size of the molecules.[122] The elution of proteins often uses harsh buffer conditions that may lead to a decrease in quality of the protein sample. As a consequence buffer has to be changed for storage. For desalting the column was equilibrated by application of three column volumes storage buffer. Then 2.5 mL protein solution were applied on the column, followed by elution using 3.5 mL storage buffer into a fresh falcon.

k) Thawing of Mammalian Cancer Cells

The cells provided as cryovial at −80° C. were thawed in a water bath at 37° C. until the ice was dissolved. The cells were resuspended and transferred to a 50 mL falcon tube. The cell suspension was centrifuged (5 min/500 rpm/RT). The supernatant was removed in vacuo and the pellet was resuspended in 5 mL cell culture medium. At this point, cells were either used in a cytotoxicity assay directly, or were given into a T75 flask containing 10 mL cell culture medium.

l) Culturing of Mammalian Cancer Cells

The cells were usually cultured in T75 cell culturing flasks in an incubator at 37° C. in a 5% C02 humid atmosphere and passaged every 3 to 4 days. For passaging, medium was removed in vacuo, cells were washed with PBS (3×) and 1 mL 0.05% Trypsin-EDTA were added. The completion of the detachment reaction was examined visually. When all cells were detached, 9 mL medium were added to the cells to stop the detachment reaction. Depending on the growth rate of the cells, they were splitted 1:2 to 1:4 and reseeded into a fresh T75 flask containing 10 mL of medium. The cells were incubated in an incubator at 37° C. in a 5% C02 humid atmosphere afterwards.

m) Curve-Shift Assays

Potentiation effects of duocarmycin-bearing ADCs with ATRi were studied to further elucidate the synergistic effects. Therefore a curve-shift assay system was established. In a first step, a dose-response curve (DRC) is obtained by treating a certain cell line with an inhibitor. The maximum non-efficacious dose (MNED) can be derived from this DRC. MNED is the highest dose, that can be added to a certain cell line without affecting the viability. The activity of the ADC is confirmed in a separate experiment. Finally, a combination experiment can be conducted. Therefore, the ADC and ADC plus inhibitor at MNED are added to the cells. The inhibitor is tested in parallel at MNED as a control. Due to the application of inhibitor at MNED, no reduction in cell viability caused by the inhibitor is expected. Three outcomes are possible: 1) The combination of ADC plus inhibitor is equipotent as the ADC only. This would suggest additive effects only. 2) The combination of ADC plus inhibitor is less potent than the ADC alone. Such a result would be interpreted as depotentiation. 3) The combination of ADC plus inhibitor is more potent than the ADC alone. In this case, the potency of the ADC is potentiated.

Potentiation effects are expressed as dose-reduction indices (DRI), which can be calculated by dividing the $IC_{50}$-value of ADC by the $IC_{50}$-value of ADC plus inhibitor according to eq. 1

$$DRI = \frac{IC_{50} \text{ of } ADC}{IC_{50} \text{ of } ADC \text{ plus inhibitor}} \qquad \text{Eq. 1}$$

Curve-shift assays were conducted as follows: The cell number and viability was determined using ViCell™-XR (Beckman Coulter) and seeded in opague 96-well plate (10k viable cells/well). After seeding, the plate was incubated (37° C., 5% C02) in a humid chamber overnight. Compounds were diluted in the appropriate medium, added to the cells and the plate was incubated (37° C., 5% CO2, 6 d) in a humid chamber. After 30 min equilibration at room temperature, CellTiter-Glo reagent (Promega) was added. After the plate was shaken (3 min, 550 rpm, rt) it was incubated (10 min, rt) and luminescence was read on a synergy 4 plate reader (BioTek). Evaluation was performed using GraphPad Prism version 6.05. Therefor luminescence values were normalized to luminescence values of non-treated cells and dose-response was fitted with 4-point logistic fit.

n) Dose-Matrix Assays

Dose-matrix combination assays were performed as described above, but performed in opague 384-well plates (2k viable cells/well). Compounds were added using Tecan D300e liquid. Protein solutions were supplemented with 0.3% Tween-20 (final) and diluted to 1 μM. All wells were normalized to the maximum amount of DMSO (maximum 0.4%) or Tween-20 added. Read out of luminescence was performed on Envision 2104 Multilabel Reader (Perkin Elmer) and data were evaluated using Genedata Screener® version 14.0.6-Standard (Genedata AG). Luminescence values were normalized to luminescence of non-treated cells and dose-response was fitted using Smart Fit. Synergy scores were calculated using LOEWE synergy model.

o) Knock-Down Experiments $0.7*10^6$ viable cells were seeded in a T25 flask, 5 mL of medium were added and the cells were incubated at 37° C. and 5% C02 overnight. The transfection was carried out as follows: 2.5 μL Lipofectamine RNAiMAX were diluted with 247.5 μL OptiMEM and a 0.3 μM siRNA (ATR, CHK1 or non-targeting siRNA) solution was prepared in OptiMEM to yield 250 μL final volume. The solutions were mixed and incubated for 20 min at room temperature, followed by the addition of 500 μL cell culture medium. The cell culture medium was removed from the cells, washed with PBS (3×) and the transfection mix was added to the cells. After 4 h incubation at 37° C. and 5% $CO_2$, the transfection mix was removed in vacuo. The cells were washed with medium (3×), 5 mL medium were added and the cells were incubated for 60 h at 37° C. and 5% CO2. Then cells were detached, and seeded into 384-well plates. Then a cytotoxicity assay was performed as described before, but with one compound only p) Statistical Analysis Statistical analysis was performed using the two-sided T.TEST formula in Microsoft Excel assuming unequal variance. The Null hypothesis for curve-shift assays was that the combination of two compounds is equally cytotoxic as the single agents alone. The Null hypothesis for synergy experiments was that the two combinations are equally synergistic. Graph annotations: *: $P<0.05$, : $P<0.01$, *: $P<0.001$, ****: $P<0.0001$.

q) Xenograft Experiment

Female H2d Rag2 mice, 6-8 weeks old, were obtained from Taconic Biosciences, LLC. A xenograft was established by harvesting NCI-N87 cells from cell culture, mixing the cells 1:1 with Matrigel and injecting 2.5×106 cells subcutaneously into the flank of the mice. The tumor volume was assessed twice weekly by length measurements in two dimensions using calipers. The volume was calculated following eq. 3 where the length L is the longest tumor length and W is the shortest tumor length.

$$V\_tumor = (L^* W^\wedge 2)/2 \quad \text{Eq. 3}$$

After an initial tumor growth phase, mice were randomized and assigned to treatment groups comprising 10 animals. The initial tumor volume amounted to approximately 100 $mm^3$ when treatment started. Vehicle treated mice obtained a solution of 0.5% Methocel, 0.25% Tween-20 in water. A single dose of 1.0 mg/kg ADC αHER2-6 dissolved in 10 mM histidine, 8% trehalose, 0.05% Tween-20, pH 6.0 buffer was given intravenously into the tail vein. The 50 mg/kg AZD6738 and ATRi 1 were given per oral dissolved in 0.5% Methocel, 0.25% Tween-20 in water once daily for two weeks. Mice were weighted twice weekly to assess the body-weight during the treatment period. The criteria to terminate the study for single animals were skin ulcerations, tumor length exceeding 15 mm or tumor exceeding 10% of the body weight. In addition, body weight loss was a criterium for termination if body weight loss exceeded 20% accompanied with a haggard appearance, body weight loss exceeded 20% on three successive days or if body weight loss exceeded 25% of the adjusted body weight. Treatment groups were completely terminated if less than eight animals/group were left and therefore no statistical analysis could have been performed. The tumor response criteria were as follows: 1) treatment result was termed tumor progression if the change in tumor volume was >73% at the end of the observation phase compared to the start of treatment. 2) Tumor stasis was reached if the tumor volume change was between −66% and 73% of initial tumor size at the end of treatment. 3) A tumor reduction of more than 66% at the end of treatment was termed regression. 4) Treatment result was termed complete regression if the tumor was non-palpable or <20 $mm^3$ at the end of treatment. The study was executed by Louisa Huettel and directed by Ana Hecht.

r) Cellular CHK1 Phosphorylation Inhibition 3500 HT29 cells (medium see appendix 1) per well were seeded in 30 μL into a black 384-well plate. Cells were incubated for 1 h at 22° C. followed by overnight incubation at 37° C., 10% C02, and 90% relative humidity. Serial dilutions of ATRi were added to the cells simultaneously with hydroxyurea at a final concentration of 3 mM. 5 μL 7×PBS/HEPES were added and DMSO yielding 0.5% final. The plate was incubated for 4 h at 37° C., 10% C02, and 90% relative humidity. Supernatant was removed using Tecan-Powerwasher. Cells were fixed by the addition of 30 μL/well 4% poly-formaldehyde in PBS and subsequent incubation for 15 min at 22° C. Cells were washed once with 80 μL PBS and supernatant was removed using Tecan Powerwasher. 40 μL per well −20° C. cold methanol were added and it was incubated 10 min at 22° C. Cells were washed once with 80 μL PBS and supernatant was removed using Tecan Powerwasher. 30 μL per well of 0.2% Triton solution in PBS were added to the cells and it was incubated for 10 min at 22° C. Cells were washed once with 80 μL PBS and supernatant was removed using Tecan Powerwasher. 25 μL of 10% goat serum, 1% BSA, 0.1% Tween-20, 0.1% sodium azide in PBS were added and it was incubated for 60 min at 37° C. The supernatant was removed and it was stained with 25 μL 1° antibody (phospho-CHK1 (Ser345, 133D3) rabbit mAb) in 1% BSA, 0.1% sodium azide in PBS overnight at 4-8° C. It was washed trice with 80 μL PBS and the supernatant was removed. 25 μL 2° antibody (Alexa Fluor®488 goat anti-rabbit $F(ab')_2$ fragment) and 0.2 μg/mL propidium iodide in 1% BSA, 0.1% sodium azide in PBS were added. The plate was incubated for 60-90 min at 37° C. It was washed trice with 80 μL PBS and 80 μL PBS supplemented with 0.1% sodium azide were added. The plate was sealed with transparent adhesive seals. Images were acquired at IMX Ultra and images were analyzed using Metaexpress 5.3.

Figure 2:
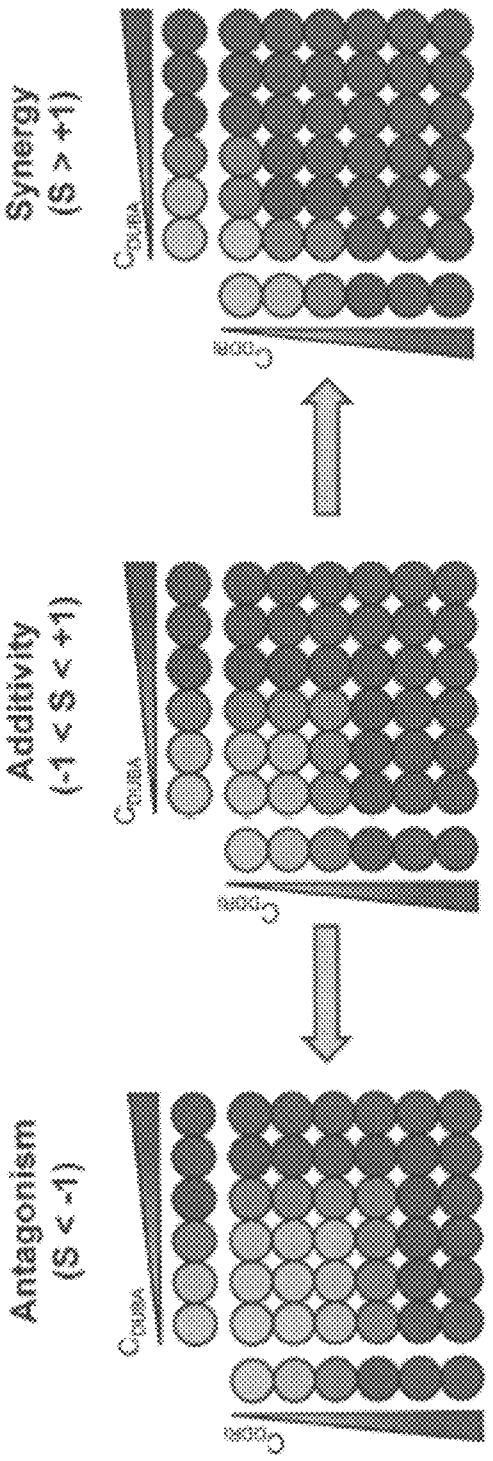
FIG. 2 shows a scheme of experimental set-up of dose-matrix assays for the determination of synergy scores. Serial dilutions of DUBA with increasing concentrations from left to right and serial dilutions of the DDRi from top to bottom are added to cells alone or in combination. The cells respond to the treatment strongly (dark) or weakly (light). Three cases have to be considered: 1) Additivity: The compounds do not interact and the resulting response of the cells does not exceed the response of the single agents. 2) Antagonism: The effect of the combination is weaker than the effect of the single agents. 3) The response to the combination treatment is stronger than the effect of the single agents.

Example 1: Screening for Synergistic Drug Combination Partner for Duocarmycins The screening of synergistic drug combinations can be accomplished by performing a dose-matrix assay. Therefore, two drugs are serial diluted and mixed at every dose level, yielding a dose-matrix. The drug combination can be additive if the effects of the combination are identical to the added effects of the single agents. However, the effects of the combination might also be stronger than the activity of the single agents. This scenario is termed synergy, whereas weaker combination effects compared to the single agents are termed antagonism. A dose-matrix assay is depicted schematically in FIG. 2 which illustrates the outcomes of a dose-matrix assay: additivity, antagonism and synergy.

The screening was conducted by serial diluting the duocarmycin derivative DUBA (10) and the DDR inhibitors. The serial dilutions were added to HCC-1954 or MDA-MB-468 cells either alone or in combination subsequently. DUBA was combined in a dose-matrix assay with hycanthone. The cell viability was measured after 6 d of treatment using the CellTiter-Glo assay kit. The signals of the cell viability assay were normalized to untreated cells and fitted. Subsequently, a prediction of additive effects according to Loewe additivity model was calculated for every dose-pair of DUBA and DDRi based on single agent activity. By subtracting the modeled data from the fitted data, an excess matrix was generated. The excess matrix can be considered as a visualization of the differences between model and actual data which also highlights spots of either high synergy or antagonism. The quantification of the combination effects, however, was performed by calculating synergy scores. Therefore, a weighted volume between the model and the fitted actual data was calculated using the GeneData Screener software which is expressed as a synergy score (S) according to the definition of the synergy score by Krueger et al. 22 In case of the combination of DUBA and Hycanthone, the synergy score amounts to 0.1 indicating additivity. The same procedure was repeated for the combination of DUBA and AZD6738. The excess matrix identified a hotspot of additional cytotoxicity at concentrations of 160 to 630 nM AZD6738 and 0.16 to 0.039 nM DUBA. In this range the activity of the combination killed up to 69% more of the cancer cells than the combination would have killed if the combination was additive. The additional cell cytotoxicity of the combination translated into a synergy score of 7.6. Besides synergy score, the potency of the drugs in monotherapy was obtained from these experiments. When plotting the activity data of the drugs DUBA and AZD6738 against the corresponding concentrations, a dose-response is yielded which was fitted using a logistic function. The potency was obtained from this dose-response curve.

The scattering of S was determined in a sham control experiment to define a cutoff for classifying a combination as truly synergistic or antagonistic. Thus seven different compounds were combined with itself on four different cell lines and the three-σ confidence interval was calculated around the mean of the measurement. According to these experiments, a combination with S in the range 0.6 to −0.7 had a probability of 99.7% to be additive. For the sake of convenience, the cutoff was set to a value of ±1.

Synergy scores (S) were obtained from the combination experiments that indicated additivity (−1>S<+1) if model and actual response were equal. If the actual response exceeded the model, a combination was synergistic (S>1) while it was antagonistic (S<1) if cells treated with the combination responded weaker compared to the single agents than to the combination treatment. The magnitude of the score determined the extent of the combination effects.

A low-throughput screening was performed to identify a synergistic combination partner for duocarmycin. Therefore, 17 small molecule DNA damage response inhibitors (DDRis) were selected that were either interfering with DNA damage repair, cell cycle regulation, DNA remodeling or that induced DNA damage based on literature data indicating a potential role in the repair of duocarmycin-induced lesions. The inhibitors with corresponding target and mode auf action are summarized in table 2.

First, inhibitors were selected that were directly involved in DNA repair. Fork collapse as a result of duocarmycin-induced replication fork stalling might lead to double-strand breaks. Thus, it was hypothesized that inhibitors of repair pathways involved in the repair of double-strand breaks might synergize with duocarmycin. Therefore amuvatinib, a down-regulator of homologous recombination repair or the DNA PK inhibitor NU7441 were combined with duocarmycin. The synergy score of KU-55933 plus DUBA exceeded the cutoff for synergy on HCC-1954 cells (S=2.1±1.2) barely, indicating either off-target inhibition or the formation of double strand breaks as a result of duocarmycin-treatment. The combination of duocarmycin-variant DUBA with DNA-PKi NU7441 or amuvatinib did not yield a synergy score exceeding the cutoff.

Besides the inhibition of double-strand repair, Bleomycin A5 and the topoisomerase II inhibitor Etoposide were combined with DUBA to overload repair capacities. On HCC-1954 cells Bleomycin A5 combined with DUBA exceeded the cutoff barely (S=1.6±1.0) while the combination was in the range of additivity on MDA-MB-468 cells (S=0.4+1.0). The combination of Etoposide with DUBA led to additive effects on both HCC-1954 (S=0.7±0.5) and MDA-MB-468 cells (S=−0.3±0.2).

The second group of selected DNA repair inhibitors was involved in the repair of damaged bases. Base excision repair is required for the direct removal of bulky DNA lesions. It was shown, that the base excision repair enzyme DNA glycosylase AlkD of *Bacillus cereus* mediates the removal of lesions caused by the duocarmycin-analogue yatakemycin. Therefore, the effects of inhibiting a human glycosylase using the O6-alkylguanine-DNA-alkyltransferase inhibitor Lomeguatrib were studied. Only weak synergistic effects with high variance were observed when Lomeguatrib was combined with duocarmycin on the cell line MDA-MB-468 (S=2.8±2.3) while additivity was observed on HCC-1954 cells (S=0.1±0.3). In addition to Lomeguatrib another BER inhibitor, TH588, was combined with DUBA. TH588 inhibits MTH1, which is involved in the resection of oxidatively damaged bases. However, on HCC-1954 (S=−0.2±0.3) and MDA-MB-468 cells (S=−0.4+0.3) additive effects were observed.

The repair pathway for the removal of damaged nucleobases is nucleotide excision repair (NER). It plays a role in the repair of duocarmycin alkylation lesions. In the presence of helicase II and DNA polymerase I, CC-1065 (15) lesions were excised by ABC excinuclease. However, NER was not recruited of cell extracts of NER-proficient HeLa cells. Only few NER inhibitors were commercially available, so the HSP90 inhibitor Tanespimycin was studied in combination experiments. The inhibitor down-regulated expression of ERCC1, a key enzyme in NER. On HCC-1954 the combination of DUBA with Tanespimycin (S=1.4±0.4) exceeded the cutoff.

A more general approach that impairs DNA damage repair was decreasing the capacity of the cells to import DNA damage response proteins to the nucleus. Microtubule-targeting agents like vincristine inhibited the translocation of the DNA repair enzymes to the nucleus leading to an accumulation of the proteins in the cytoplasm. It was hypothesized that, upon duocarmycin-treatment, the dynein inhibitor ciliobrevin D might hinder the transport of the DNA damage response enzymes to the nucleus and thereby increase the accumulation of DNA damage. However, the combination of ciliobrevin D with duocarmycin-derivative DUBA exceeded the cutoff only barely on the cell line HCC-1954 (S=1.2+0.6) while on MDA-MB-468 cells additive effects were observed (S=0.2±0.5). These results were in line with the combination experiments of the microtubule inhibiting ADC Kadcyla plus AZD6738. The synergy scores of Kadcyla combined with AZD6738 were S=1.1±0.3 on MDA-MB-453 and S=0.3+0.2 on NCI-N87 cells indicating only additivity.

The third group of studied inhibitors included drugs that abrogate checkpoint regulation. The WEE1 kinase is involved in checkpoint regulation. Activity of WEE1 lengthens the G2 phase to gain time for the repair of DNA damage accumulated in S phase. When WEE1 is inhibited by AZD1775, the G2/M checkpoint is abolished which leads to the cells entering mitosis. WEE1 inhibition synergizes with CHK1/2 inhibition in patient-derived xenograft models in mice and generally sensitizes cells for treatment with DNA damaging agents. The combination of DUBA and AZD1775 was additive in our study on HCC-1954 (S=0.8±0.1) and MDA-MB-468 (S=0.1±0.4) cells. The enzyme PARP1 plays an important role in several repair pathways like homologous recombination repair, non-homologous end joining and also base-excision repair. Furthermore, it binds to stalled-replication forks (SRFs) and is activated by the presence of SRF. Cells lacking PARP1 are sensitive to treatment with hydroxyurea and excess thymidine which causes replication fork collapse or stalling, respectively. Since the treatment with duocarmycin leads to the formation of stalled replication forks this suggests a potential role in the sensing of duocarmycin-induced DNA lesions. In this study, olaparib combined with DUBA displayed additive effects on HCC-1954 (S=0.6+0.4) and minor synergistic effects on MDA-MB-468 cells (S=1.1+0.1).

ATR and CHK1 kinases are crucial enzymes in the cell cycle but also DNA-damage response regulation. ATRi AZD6738 and the CHK1i LY2603618 as well as AZD7762 were identified as synergistic combination partners of DUBA. The ATRi AZD6738 strongly synergized with DUBA on HCC-1954 cells (S=6.9±0.7) and MDA-MB-468 cells (S=5.7±1.0). The synergy was stronger for ATRi AZD6738 plus DUBA than for LY2603618 plus DUBA on HCC-1954 (S=4.1+0.3, P=0.00002) and MDA-MB-468 cells (S=4.4+1.7, P=0.3). Again, the combination of AZD6738 with DUBA also exceeded the synergy observed for AZD7762 combined with DUBA on HCC-1954 (S=3.6±0.4, P=0.0002) and on MDA-MB-468 cells (S=2.6+0.2, P=0.01).

Functional HER2 was described to be essential for the activation of the G2/M checkpoint following irradiation of MCF7 cells. HER2 inhibition led to abolished ATR and CHK1 signaling following treatment of MCF7 with irradiation. It was shown that ATR and CHK1 synergized with DUBA, it was studied whether the dual-epidermal growth factor receptor and HER2 inhibitor Lapatinib or the HER2 inhibitor CP724714 synergized with DUBA. The combination of both inhibitors with DUBA resulted in additive effects on HCC-1954 and MDA-MB-468 cells.

Figure 3:
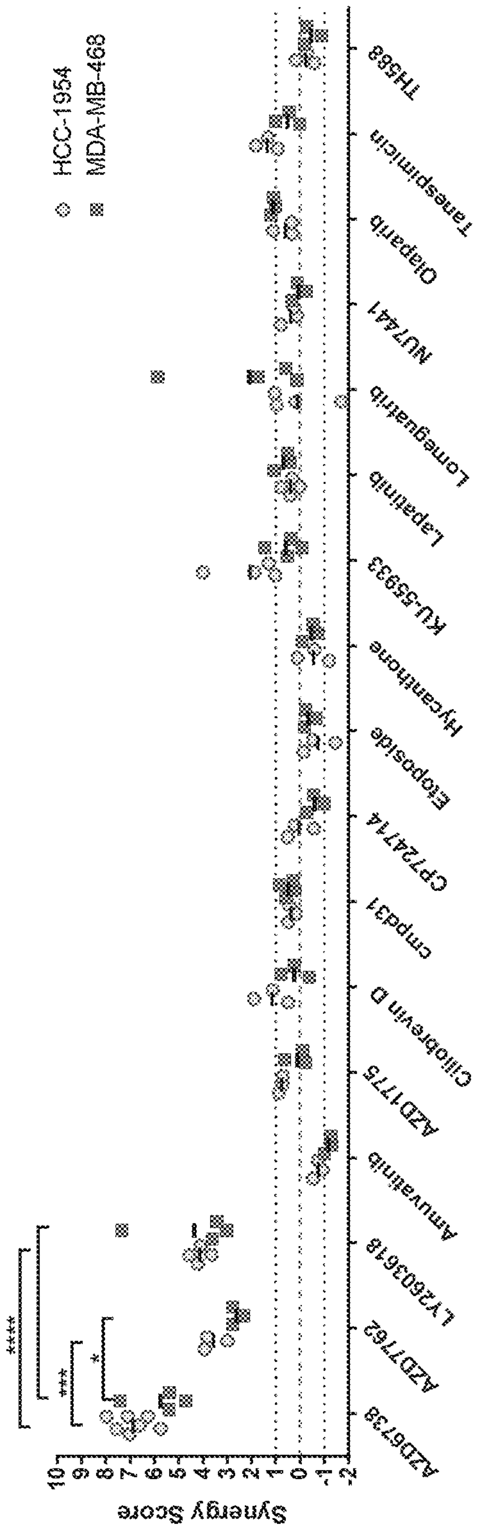
FIG. 3 shows results of the synergy screening. Duocarmycin variant DUBA was combined with DDRi on HCC-1954 and MDA-MB-468 cells and the combination effect was reported as synergy score. A cutoff synergy score of ±1 was defined. In this range, S of combinations is assumed to be additive, S>1 indicates synergism, S<1 indicates antagonism. Individual data points from independent experiments are depicted as well as the mean of the biological replicates as bar.

NEK1 is a kinase associated with ATR and ATRIP that regulates the interplay between these two kinases. Although originally designed for the inhibition of NEK2, cmpd31 inhibits NEK1 with a potency of 0.17 µM. Thus, cmpd31 was combined with DUBA. On HCC-1954 (S=0.3±0.1) and MDA-MB-468 cells (S=0.4±0.2) only additivity was observed. The results of the dose-matrix assays are depicted in FIG. 3.

knock-down cells (IC50=1.1 nM) compared to cells treated with non-targeting siRNA (IC50=1.5 nM). Similar results were obtained for DDM which was again more potent on ATR (IC50=0.014 nM) and CHK1 (IC50=0.133 nM) knock-down cells than on control cells (IC50=0.23 nM). The differences between CHK1 and non-targeting siRNA treated cells were small, but DUBA was 5.8-fold and DDM 17.3-fold more potent on ATR knock-down cells than on control cells.

All in all, the combination of DUBA with the ATRi AZD6738 yielded superior synergistic effects compared to DUBA plus CHK1i LY2603618 or AZD7762. In addition, the potentiation of the duocarmycins was stronger on ATR

TABLE 2

Inhibitors used in the screening. Target enzyme and mode of action of each inhibitor are listed and a class is assigned according to the function of the enzyme.

| Inhibitor | Target | Mode of action | Class |
|---|---|---|---|
| Amuvatinib | multiple tyrosine kinases | Decreased Rad51 expression, thus impairing HR | DNA repair |
| Lomeguatrib | $O^6$-alkylguanine-DNA-alkyltransferase | Removes alkylation adducts at $O^6$ of guanine | |
| NU7441 | DNA-PK | Double-strand repair | |
| Olaparib | PARP | SSB sensing[97] | |
| Tanespimycin | | Downregulation of ERCC1 mRNA, required in NER | |
| TH588 | MTH1 | Oxidation damage repair | |
| AZD1775 | WEE1 | Blocking of G2/M transition for elongated period of time for DNA repair | Cell cycle |
| AZD6738 | ATR | Cell cycle and DNA damage response regulation | |
| AZD7762 | CHK1 | Cell cycle arrest, DNA repair regulation | |
| cmpd31 | NEK1 | Essential for ATR activity | |
| LY2603618 | CHK1 | Cell cycle arrest, DNA repair regulation | |
| Bleomycin A5 | | induces double strand breaks | DNA damage |
| Etoposide | TOP2 | Double-strand breaks | DNA remodeling |
| CP-724714 | HER2 | HER2 inhibition impairs ATR activation | Other |
| Hycanthone | | RNA synthesis inhibitor | Other |
| Lapatinib | HER2/EGFR | HER2 inhibition impairs ATR activation | Other |
| Ciliobrevin D | Cytoplasmic dynein | Intracellular trafficking hinders delivery of repair enzymes | Protein transport |

Since kinase inhibitors often display off-target effects, ATR and CHK1 levels were decreased using siRNA knock-down to prove the essential role of these enzymes for the survival of the cells treated with duocarmycin. Therefore, HCC-1954 cells were seeded into T25 flasks and left to adhere overnight. Then the cells were washed with PBS, and subsequently ATR, CHK1 and non-targeting siRNA were added. The cells were incubated for 4 h, washed with medium and incubated for 3 d. Cells were detached and seeded into 384-well plates. They were treated with duocarmycins for 6 d. Cell viability was determined via CellTiter-Glo assay kit, and data were evaluated using GraphPad Prism. The knock-down efficiency was evaluated using quantitative PCR.

TABLE 3

Knock-down efficiency of ATR and CHK1 as determined by quantitative PCR. The efficiency of individual experiments is noted

| Cells | Knock-down efficiency [%] |
|---|---|
| ATR KD | 90, 74 |
| CHK1 KD | 63, 15 |

Figure 4:
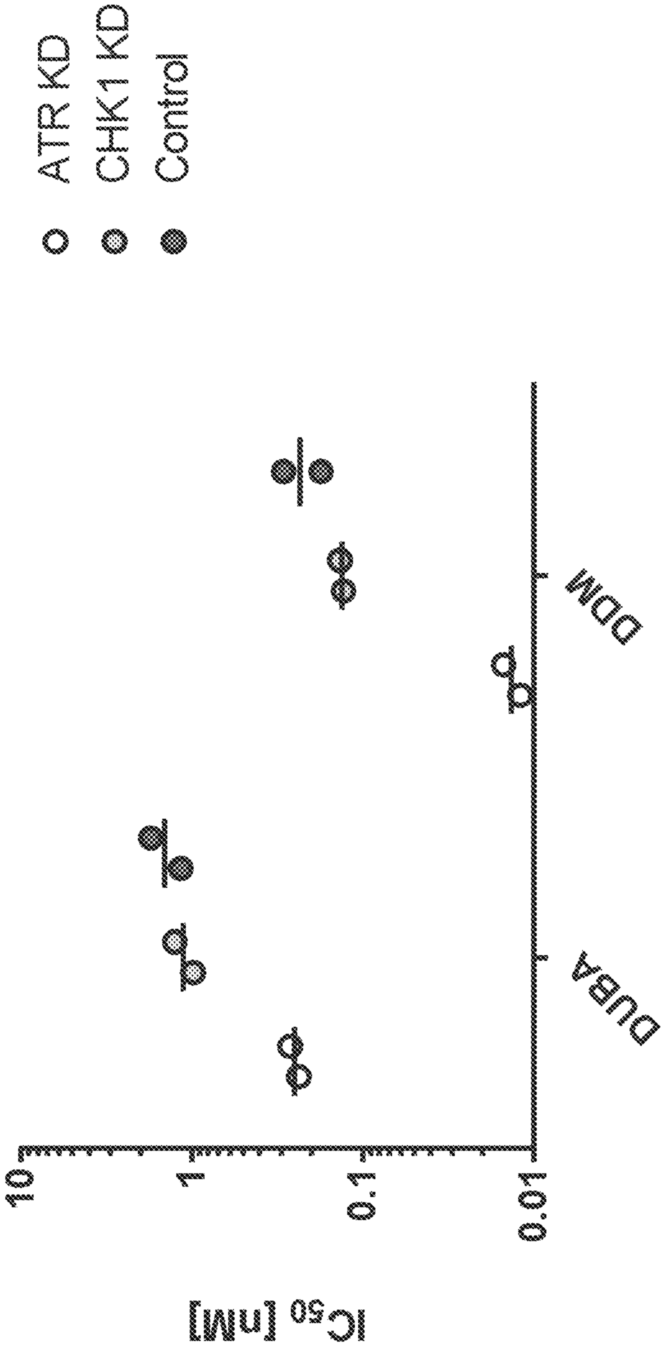
FIG. 4 shows potency of DDM and DUBA on cells treated with ATR or non-targeting siRNA. Individual data points and mean of IC50-values as black bar are displayed.

The results are displayed in FIG. 4. DUBA was more potent on ATR knock-down (IC50=0.25 nM) and CHK1-knock-down versus CHK1 knock-down cells. Taken together, it was proceeded with studying the drug combination of duocarmycin with ATR inhibitors due to their consistently stronger synergistic effects.

Example 2: Synergistic Drug Combinations of a Duocarmycin Library with ATR Inhibitor AZD6738

A series of duocarmycin variants was studied after the identification of the synergistic drug combination DUBA plus AZD6738. This should verify that the observed synergy is not an effect caused by DUBA, but duocarmycins in general. Therefore, the duocarmycin variants were clustered into two groups according to their structural features. In the trimethoxy indole (TMI)-series, the binding unit of the duocarmycin is kept constant, while the alkylating unit varies. The alkylating unit of Duocarmycin SA (13) and CBI-TMI (24) consist of a tricyclus, however, with different stereoelectronic properties. The alkylating unit of the latter have a chiral center. Contrasting this, three achiral duocarmycin variants were investigated. From these, two variants, duocarmycin 35 and 36, had a bicyclic alkylating unit, while 37 had a monocyclic alkylating unit. The structures of the TMI-series are summarized in table 4.

TABLE 4

Chemical structures of duocarmycins from the TMI-series.
In the trimethoxy indole (TMI)-series, the binding unit is kept constant, while the alkylating unit varies. Cytotoxicity of the duocarmycin variants was determined by treating HCC-1954 cells with the compounds. The potency of the duocarmycin variants is expressed as mean of IC50 ± SD of N = 3 biological replicates except in case of variant 35, where mean and individual IC50 values are noted. Synergy scores were obtained by combination treatment of HCC-1954 cells with the duocarmycin variant and AZD6738. Synergy scores are depicted as S ± SD of N = 3 biological replicates.

| Alkylating unit | Binding unit | No. | $IC_{50}$ [nM] | S |
|---|---|---|---|---|
| 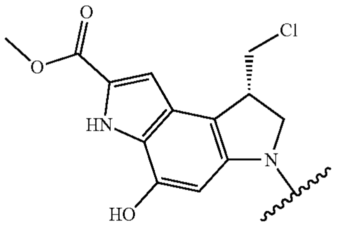 [SMILES: *N1C[C@@H](CCl)c2c1cc(O)c1[nH]c(C(=O)OC)cc21] | 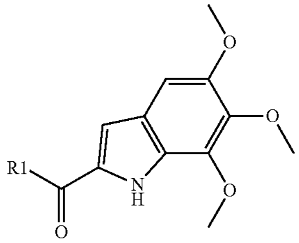 | 13 | 0.3 ± 0.1 | 4.1 ± 0.4 |
| 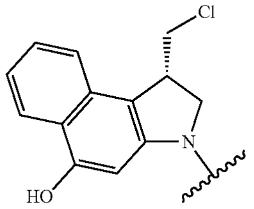 [SMILES: *N1C[C@@H](CCl)c2c1cc(O)c1ccccc21] | | 24 | 24 ± 32 | 6.1 ± 1.2 |
| 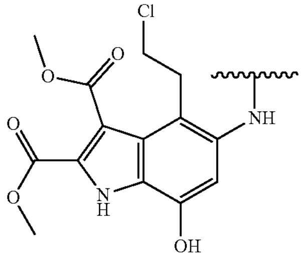 [SMILES: *Nc1cc(O)c2[nH]c(C(=O)OC)c(C(=O)OC)c2c1CCCl] | | 35 | 43.5 (44, 43) | 5.2 ± 0.2 |
| 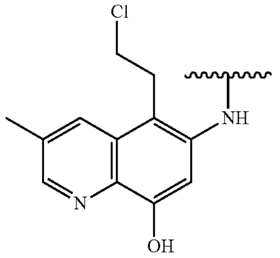 [SMILES: *Nc1cc(O)c2ncc(C)cc2c1CCCl] | | 36 | 3.0 ± 0.4 | 6.7 ± 0.8 |
| 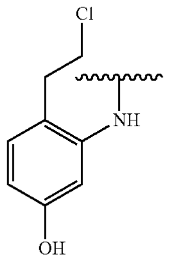 [SMILES: *Nc1cc(O)ccc1CCCl] | | 37 | 1200 ± 536 | 2.8 ± 0.5 |

The TMI-series might elucidate the influence of the alkylating unit on the synergy between duocarmycins and ATR inhibitors. The cyclopropabenzindole (CBI)-series (Table 5) was used to study the influence of the binding unit on the synergistic effects between duocarmycin variants and ATRi. In the 0B1-series, the alkylating unit is kept constant with only minor modifications like methyl or hydrogen in R1 and the binding unit is varied.

TABLE 5

Chemical structures of duocarmycins from the CBI-series.
In this series, the alkylating unit is a CBI-unit with either methyl- or hydrogen in position R1 of the alkylating unit.
The binding unit in position R2 is varied. Cytotoxicity was determined by treating HCC-1954 with the duocarmycins.
Synergy scores were obtained by combination treatment of HCC-1954 cells with the duocarmycin variant and AZD6738.
Data of 10 and 38 are IC50 ± SD and S ± SD of N = 7 or N = 9 biological replicates, respectively.
For experiments with N = 2 biological replicates, mean and individual IC50 values are noted in brackets.

| Alkylating unit | | Binding unit | | | | |
|---|---|---|---|---|---|---|
| | R1 | R2 | R3 | No. | $IC_{50}$ [nM] | S |
| 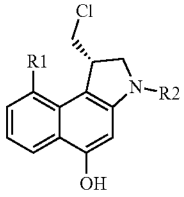 | H | 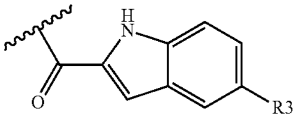 | 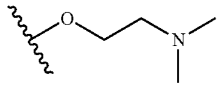 | 38 | 0.11 ± 0.05 | 5.6 ± 1.7 |
| | H | | 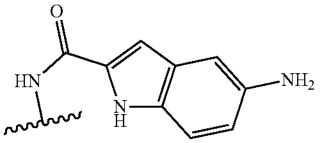 | 39 | 0.16 (0.21, 0.11) | 5.1 (4.8, 5.3) |
| | Me | 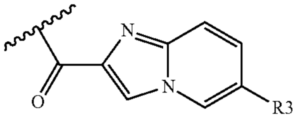 | 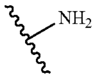 | 40 | 1.6 (1.7, 1.5) | 6.7 (6.3, 7.2) |
| | Me | | 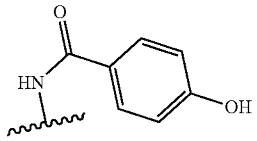 | 10 | 0.3 ± 0.1 | 6.9 ± 0.7 |

To study synergistic effects of the duocarmycin variants in combination with the ATRi AZD6738, HCC-1954 cells were treated either with the single agents or with a combination of the two respective drugs. After 6 d of treatment, CellTiter-Glo luminescent assay was performed and the luminescence was read on Envision Reader. The results were analyzed using GeneData Screener as described before. The outcome of the assay was the potency of the duocarmycin variants and synergy scores for each variant combined with AZD6738.

The potencies in the TMI-series on HCC-1954 cells were scattered strongly (Table 4). While DSA (13) had a subnanomolar IC50-value of 0.3±0.1 nM, the duocarmycin variant with the monocyclic alkylating unit 37 had a micromolar IC50-value of 1.2±0.5 μM. The potencies of the remaining duocarmycin variants in the TMI-series lay in between. Duocarmycin 36 had a potency in the single-digit nanomolar range with 3.0±0.5 nM, and 24 and 35 have IC50-values of 24±32 nM and 43.5 nM, respectively. The potencies of the duocarmycins in the CBI-series were distributed more evenly (Table 5). Duocarmycin DM (38) had an IC50-value of 0.12±0.03 nM and DUBA (10) an IC50-value of 0.2±0.1 nM. Compound 39 had a potency of 0.16 nM and duocarmycin 40 a potency of 1.6 nM.

The previously determined cutoff for synergy scores of 1 was exceeded by all compounds tested. However, the synergy scores varied strongly in the TMI-series. While the duocarmycin with the bicyclic, achiral alkylating unit 36 reached a synergy score of 6.7±0.8 in combination with AZD6738, it was followed by the duocarmycins with tricyclic, chiral alkylating units CBI-TMI (24) (S=6.1±1.2) and DSA (13) (S=4.1±0.4). Drug 35 with the bicyclic, achiral alkylating unit had a score of 5.2±0.2 when given together with AZD6738.

The weakest synergistic effects were reached with the duocarmycin 37 comprising the monocyclic, achiral alkylating unit (S=2.8±0.5). The differences were less pronounced in the CBI-series. The duocarmycins DDM (38) and 39 had synergy scores close to each other (S=5.6±1.7 and S=5.1, respectively). The duocarmycins with the methyl-CBI unit as alkylating unit also had comparable synergy scores. While DUBA (10) had a synergy score of S=6.9±0.7 when combined with AZD6738, the combination of the DUBA-progenitor 40 with AZD6738 reached S=6.7.

The drugs DDM (38) and DUBA (10) were chosen for further experiments. Duocarmycins synergized with the ATRi AZD6738 regardless of their structural features, It was investigated whether the duocarmycin variant DUBA also synergizes with other inhibitors of ATR.

Example 3: Biological Activity of ATR Inhibitors

Figure 5:
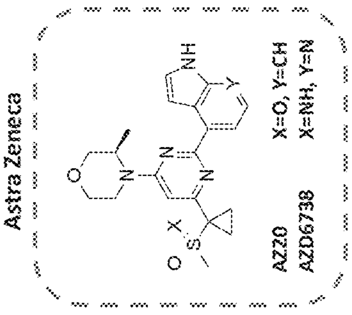
FIG. 5 shows an overview of the chemical structures of the ATRi studied in the report of example 3.
Figure 5:
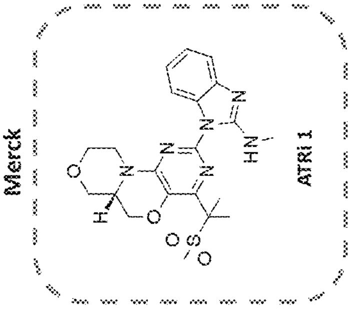
Figure 5:
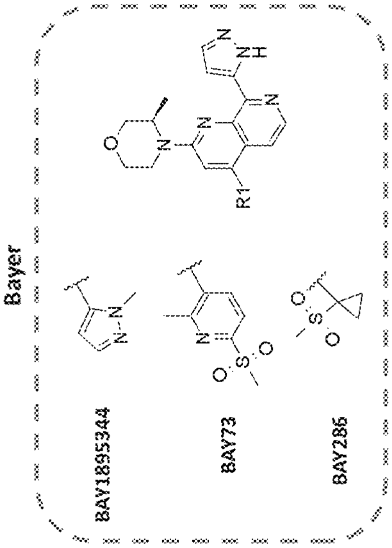
Figure 5:
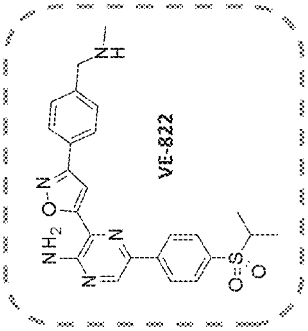

In the combination experiments with AZD6738 it was confirmed that the duocarmycin variant plays a role in the extent of the synergistic effects. In this work, several different ATR inhibitors were investigated to elucidate the influence of the ATRi on the combination effects. An overview of the chemical structures of the ATRi studied in this report is given in FIG. 5. The ATRi were clustered into four groups. The ATRi from Astra Zeneca AZ20 and AZD6378 are closely related with an identical core unit. Bayer ATR inhibitors also had identical core units. The three Bayer ATRi differed only in R1. The phase I ATRi BAY1895344 carried a pyrazole residue and the ATRi BAY73 was carrying a methanesulfone pyridine residue in R1. The Bayer ATRi BAY286 carried a methanesulfone moiety in R1. VE-822 was structurally unrelated to the remaining cluster.

Table 6 summarizes characteristic properties and the chemical structures of the ATRi. Two compounds developed by Astra Zeneca were studied, namely AZ20 (ATRi 2) and phase I ATRi AZD6738 (ATRi 3). Furthermore, compounds from Bayer were included. The phase I ATRi BAY1895344 (ATRi 1) was studied, as well as two ATRi, published as example 73 or example 286 in a patent by Bayer AG149, termed BAY73 (6) and BAY286 (ATRi 5), respectively. In addition, ATRi 1 and Merck's phase I ATRi VE-822 (ATRi 7) were investigated. Cellular cytotoxicity was represented by the anti-proliferative potency on HCC-1954 cells.

AZD6738 was the least potent ATRi in the panel (2.2±0.7 µM) followed by AZ20 with an IC50-value 1.6±0.5 µM. VE-822 was potent in submicromolar range with a potency of 0.9±0.4 µM. The potency increased with ATRi 1 (0.4±0.2 µM) and the drugs from Bayer BAY1895344 (0.05±0.02 µM), BAY73 (0.12±0.03 µM), BAY286 (0.08±0.02 µM). In addition, cellular cytotoxicity was determined on NCI-N87 and MDA-MB-453 cells. While ATRi 1 was potent in the same range on NCI-N87 (0.36±0.07 nM) and on MDA-MB-453 (0.32±0.5 nM) cells as on HCC-1954, the potency of BAY1895344 varied stronger between the cell lines. It was remarkably less potent on NCI-N87 (0.3±0.3 nM) and MDA-MB-453 (0.2±0.2 nM) when compared to HCC-1954 cells. AZD6738 on the other hand was more around twice as potent on NCI-N87 (0.98±0.09 nM) and MDA-MB-453 (1.1±0.3 nM) cells compared to the potency on HCC-1954 cells.

TABLE 6

Summary of ATR inhibitors. Trivial name and structure are depicted.
The cellular toxicity on HCC-1954, NCI-N87 and MDA-MB-453 cells are noted as mean ± SD of IC50-values.
The data are displayed as mean ± SD and the number of individual experiments is noted in brackets..

| ATRi | No. | Structure | Cytotoxicity $IC_{50}$ HCC-1954 µM | NCI-N87 | MDA-MB-453 |
|---|---|---|---|---|---|
| ATRi 1 | 1 | 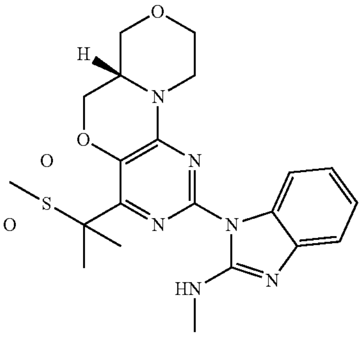 | 0.4 ± 0.2 (9) | 0.36 ± 0.07 (3) | 0.32 ± 0.5 (3) |
| AZ20 | 2 | 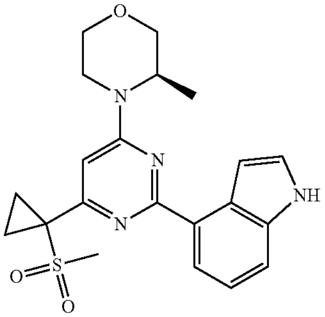 [SMILES: C[C@@H]1COCCN1c1cc(C2(S(C)(=O)=O)CC2)nc(-c2cccc3[nH]ccc23)n1] | 1.6 ± 0.5 (7) | — | — |
| AZD6738 | 3 | 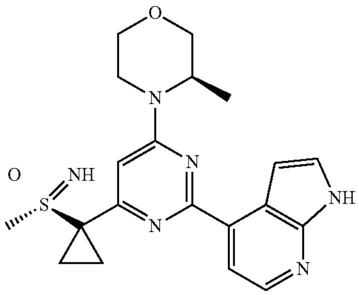 | 2.2 ± 0.7 (21) | 0.98 ± 0.09 (3) | 1.1 ± 0.3 (6) |

TABLE 6-continued
Summary of ATR inhibitors. Trivial name and structure are depicted.
The cellular toxicity on HCC-1954, NCI-N87 and MDA-MB-453 cells are noted as mean ± SD of IC50-values.
The data are displayed as mean ± SD and the number of individual experiments is noted in brackets..
| | | | Cytotoxicity $IC_{50}$ | | |
|---|---|---|---|---|---|
| ATRi | No. | Structure | HCC-1954 | NCI-N87 μM | MDA-MB-453 |
| BAY1895344 | 4 | 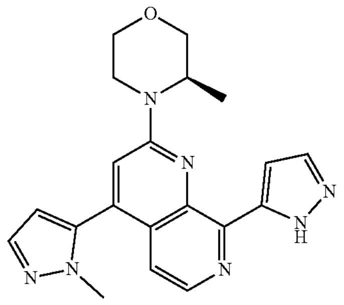 [SMILES: C[C@@H]1COCCN1c1cc(-c2ccnn2C)c2ccnc(-c3ccn[nH]3)c2n1] | 0.05 ± 0.02 (9) | 0.3 ± 0.3 (3) | 0.2 ± 0.2 (4) |
| BAY286 | 5 | 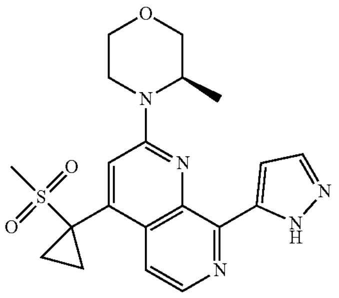 [SMILES: C[C@@H]1COCCN1c1cc(C2(S(C)(=O)=O)CC2)c2ccnc(-c3ccn[nH]3)c2n1] | 0.08 ± 0.02 (5) | — | — |
| BAY73 | 6 | 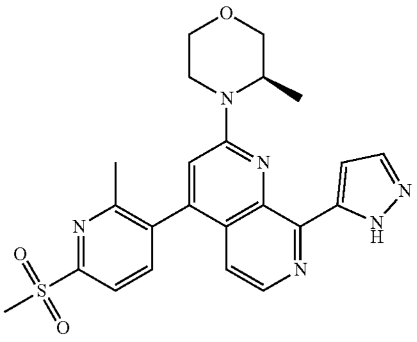 [SMILES: Cc1nc(S(C)(=O)=O)ccc1-c1cc(N2CCOC[C@H]2C)nc2c(-c3ccn[nH]3)nccc12] | 0.12 ± 0.03 (7) | — | — |
| VE-822 (VX-970, M6620 Berzosertib) | 7 | 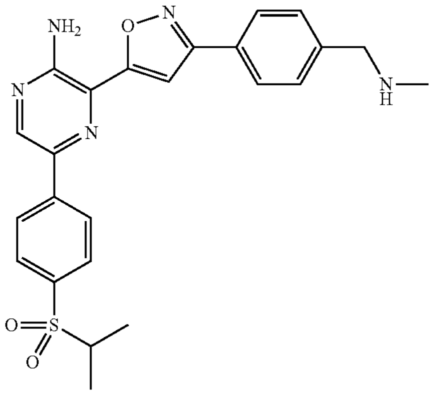 [SMILES: CNCc1ccc(-c2cc(-c3nc(-c4ccc(S(=O)(=O)C(C)C)cc4)cnc3N)on2)cc1] | 0.9 ± 0.4 (7) | — | — |

Example 4 ADC Generation

Generation of Duocarmycin-Bearing ADCs

In this work, several duocarmycin-bearing ADCs were generated based on antibodies targeting cancer-related receptor-tyrosine kinases HER2, EGFR and mesenchymal-epithelial transition (MET). The linker-drugs that were coupled to these antibodies were specified by the tag LD X, where X refers to the index number of a specific structure. The name of the resulting ADC was composed of the target or the name of the antibody and the linker-drug index number. For instance, an ADC composed of linker-drug 1 (LD-1) and the anti-EGFR (αEGFR) antibody or anti-HER2 (αHER2) carried the name αEGFR-1 or αHER2-1, respectively.

The linker-drugs for the generation of duocarmycin-bearing ADCs are summarized in table 7. The basic structure of the linker-drugs utilizes a dipeptide valine-citrulline linker, which can be cleaved by cathepsin B. The dipeptide is followed by a self-immolative module, which ensures efficient drug release upon cleavage. The self-immolative module carries either a methyl group or a diethylgycol moiety in R2 position. The basic structure is elongated N-terminally at R1. The linker-drugs LD-1 to LD-5 contain a N-terminal triple-glycine sequence to enable Sortase A (SrtA)-mediated conjugation. Several modifications were introduced to increase the solubility of the linker-drugs. LD-2 and LD-5 are modified with ethyleneglycol. Since charge can also mediate solubility, LD-3 contains a lysine which is positively charged at physiological pH. LD-6 was conjugated via chemical conjugation techniques. LD-7 is modified N-terminally by a maleimide motif for the conjugation to thiols. In both linkers, an ethyleneglycol unit is incorporated to increase solubility. The duocarmycin-variants DDM (LD-1), DUBA (LD-2 to LD-6) and DSA (LD-7) were used as drugs in R3 (see FIG. 6).

TABLE 7

Duocarmycin-based linker-drugs used for ADC preparation.

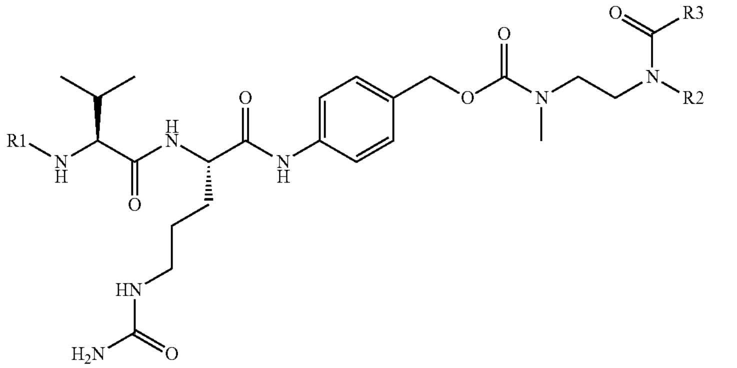

| Linker-drugs | R1 | R2 | R3 |
|---|---|---|---|
| 1 | 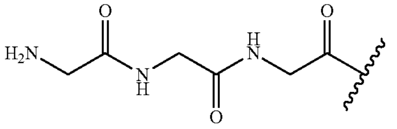 [SMILES: *C(=O)CNC(=O)CNC(=O)CN] | Me | 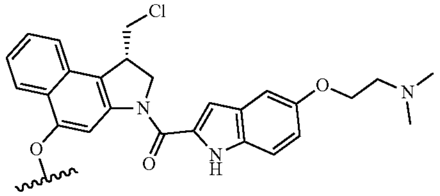 [SMILES: *Oc1cc2c(c3ccccc13)[C@H](CCl)CN2C(=O)c1cc2cc(OCCN(C)C)ccc2[nH]1] |
| 2 | 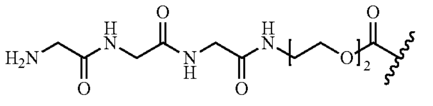 | 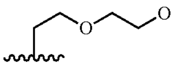 [SMILES: *CCOCCO] | 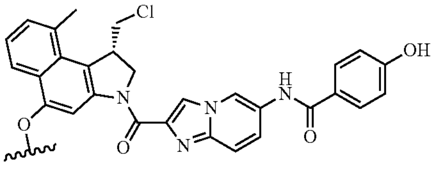 [SMILES: *Oc1cc2c(c3c(C)cccc13)[C@H](CCl)CN2C(=O)c1cn2cc(NC(=O)c3ccc(O)cc3)ccc2n1] |
| 3 | 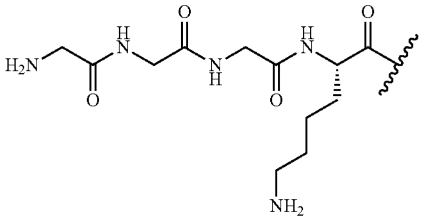 [SMILES: *C(=O)[C@H](CCCCN)NC(=O)CNC(=O)CNC(=O)CN] | Me | 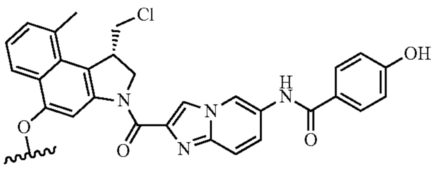 [SMILES: *Oc1cc2c(c3c(C)cccc13)[C@H](CCl)CN2C(=O)c1cn2cc(NC(=O)c3ccc(O)cc3)ccc2n1] |

TABLE 7-continued

Duocarmycin-based linker-drugs used for ADC preparation.

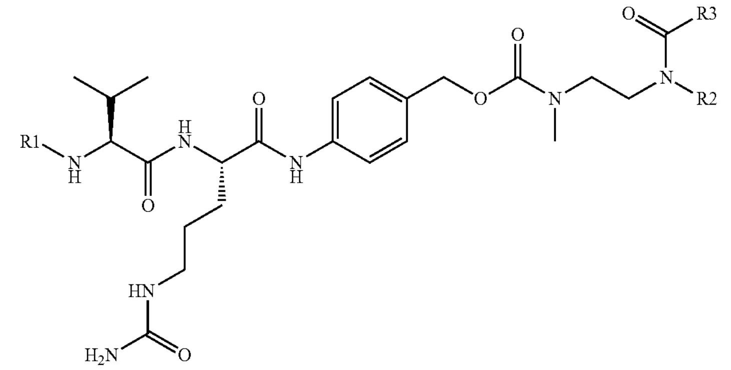

| Linker-drugs | R1 | R2 | R3 |
| --- | --- | --- | --- |
| 4 | Not disclosed | Me | 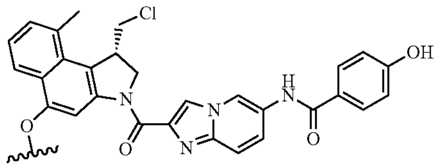 [SMILES: *Oc1cc2c(c3c(C)cccc13)[C@H](CCl)CN2C(=O)c1cn2cc(NC(=O)c3ccc(O)cc3)ccc2n1] |
| 5 | 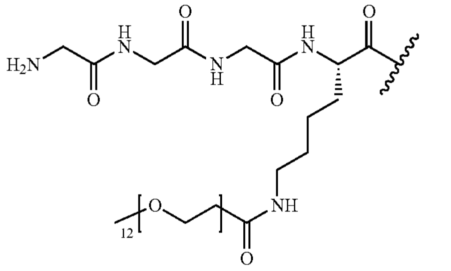 | Me | 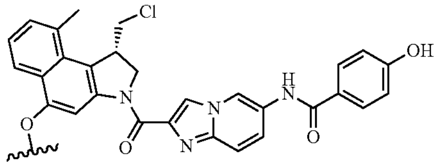 [SMILES: *Oc1cc2c(c3c(C)cccc13)[C@H](CCl)CN2C(=O)c1cn2cc(NC(=O)c3ccc(O)cc3)ccc2n1] |
| 6 | Not disclosed | 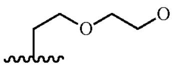 [SMILES: *CCOCCO] | 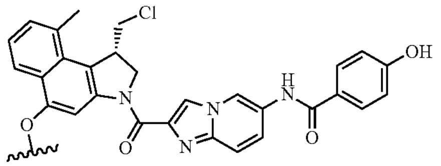 [SMILES: *Oc1cc2c(c3c(C)cccc13)[C@H](CCl)CN2C(=O)c1cn2cc(NC(=O)c3ccc(O)cc3)ccc2n1] |
| 7 | 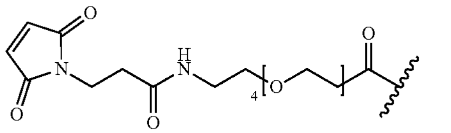 | Me | 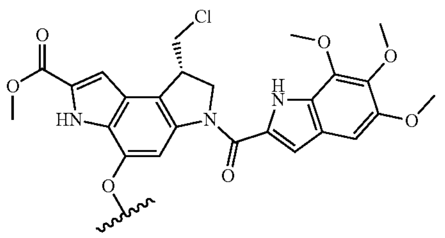 |

R1: Linker-drugs LD-1 to LD-5 are modified N-terminally with a triple-glycine motif that is recognized by SrtA. LD-2 to LD-5 contain modifications that increase the hydrophilicity. Thus, ethyleneglycol units are introduced in LD-2 and LD-5. LD-3 comprises a lysine residue and hence is positively charged at a physiological pH. LD-6 was prepared by chemical conjugation to the αHER2 antibody. LD-7 carries a N-terminal maleimde residue for conjugation using thiol coupling and ethyleneglycol units for increased solubility.
R2: Methyl group or diethyleneglycol is used. Diethyleneglycol increases solubility.
R3: Linker-drugs contain Duocarmycin DM (LD-1), DUBA (LD-2 to LD-6) or DSA (LD-7).

The conjugation of LD-1 to the αHER2 mAb was performed using SrtA-conjugation. Therefore, antibody modified C-terminally with (G4S)3-LPETGS was mixed with LD-1, $CaCl_2$ solution and buffer. Then SrtA was added to start the reaction. After 30 min of shaking at 22° C., the reaction was stopped by adding an excess of EDTA. The sample was then subjected to Protein A chromatography. The flow through was discarded, and after a washing section, the ADC was eluted using an acidic pH shift. After buffer exchange and concentration, the resulting purified ADC was analyzed by analytical HIC and SEC.

The αHER2 mAb was used as a tool antibody in the course of this work to study the impact of duocarmycin linker-drugs on the producibility of ADCs. Therefore, LD-1 to LD-5 were conjugated to the αHER2 mAb via SrtA-mediated conjugation in analytical scale reactions at first. The LD-4 could not be conjugated to the αHER2 mAb, since the resulting product was precipitated. LD-5 was successfully conjugated to the αHER2 mAb in an analytical scale reaction. However, the conjugation reaction was incomplete, leading to an ADC with a DAR of approximately 1. The linker-drugs LD-1, LD-2, and LD-3 were successfully coupled to the αHER2 mAb using antibody-format A in preparative scale. In this setting, homogeneous ADCs with a DAR>1.85 were prepared and the monomer content of the ADC was at least 95%. While the DUBA-based linker-drugs LD 2 and LD-3 were conjugated to the αHER2 mAb in excellent or very good yield, respectively, the preparation of αHER2-1 was performed in poor to good yield.

In addition to that, LD-1 was conjugated to the αEGFR mAb cetuximab, and the mAbs αMET, αMET×EGFR and αHEL (Hen egg lysozyme, isotype control). The resulting ADCs were prepared in acceptable yields. While a DAR von 1.90 was achieved in the preparation of αHEL-1, the preparation of αEGFR-1 and αMET-1 yielded ADCs with a DAR of 1.70 and 1.68, respectively. In the case of the αMET×EGFR-1 ADC a DAR of 0.89 and 0.95, respectively, was achieved. The monomer content of these ADCs was acceptable, except for αMET-1, where the monomer content was the lowest with 93.6%.

interchain cysteines. A DAR of 1.54 was achieved. Both ADCs did only contain negligible amounts of aggregates.

Example 5: Cytotoxicity of Duocarmycin-Based ADCs

In this chapter, the anti-proliferative effects of duocarmycin-based ADCs are described. The cytotoxicity of ADC αHER2-1 was studied on HER2-positive cells. The cell panel encompassed the breast-cancer cell lines BT-474, HCC-1954, JIMT-1, MDA-MB-361, MDA-MB-453 and SK-BR-3 as well as the lung adenocarcinoma cell line Calu-3. Furthermore, the ADC was tested on a HER2-negative breast cancer cell line MDA-MB-468. αHER2-1 was active in the double-digit picomolar to single-digit nanomolar range on the HER2-positive cell lines and showed only weak cytotoxicity on HER2-negative cell line MDA-MB-468 in the lower triple-digit nanomolar range. The ADCs αHER2-2 and αHER2-3 were as cytotoxic as αHER2-1 on Calu-3, HCC-1954 and SK-BR-3 cells. However, Kadcyla was 5- to 45-fold less potent on Calu-3 compared to the duocarmycin-based ADCs. Kadcyla, as well as αHER2-2 and αHER2-3 were potent in the double-digit nanomolar range on antigen-negative cells. The non-targeting ADC αHEL-1 exhibited weak anti-proliferative effects on HER2-positive cells in the double- to triple digit nanomolar range. The ADC αHER2-6 had subnanomolar IC50-

TABLE 8

Overview of generated duocarmycin-based ADCs using SrtA conjugation. The column "App." contains the appendix number under which data such as HIC and SEC profile can be found.

| mAb | mAb format | Linker-drug | Purification route | Yield [μg] (%) | Yield [%] | DAR | Monomer [%] |
|---|---|---|---|---|---|---|---|
| αHER2 | A | 1 | D/C/C | 2760/1443/2850 | 34.4/28.8/71.0 | 1.97/1.89/1.96 | 98.8/95.6/96.7 |
| αEGFR | B | 1 | C | 1350 | 66.5 | 1.70 | 98.2 |
| αMET | B | 1 | B | 1064 | 52.4 | 1.68 | 93.6 |
| αMET × EGFR | C | 1 | A/A | 503/620 | 57%/74.3 | 0.95/0.89 | 98.4/98.4 |
| αHEL | A | 1 | C | 2400 | 47.8 | 1.90 | 97.2 |
| αHER2 | A | 2 | B | 1984 | 97.8 | 1.85 | 97.4 |
| αHER2 | A | 3 | A | 2150 | 81.1 | 1.93 | 99.3 |
| αHER2 | A | 4 | — | — | — | Precipitated | — |
| αHER2 | A | 5 | — | — | — | 0.99 | — |
| α-GP | B | 1 | D | 1215 | 60.0 | 1.57 | 89.4 |

The ADC αHER2-6 was generated using chemical conjugation techniques resulting in an ADC with a DAR of 1.90. αEGFR-7 was produced by conjugation of LD-7 to the values on NCI-N87 and MDA-MB-453, which was comparable to the effects of Kadcyla. αHER2-6 was comparably as potent as αHER2-2 on NCI-N87 cells.

TABLE 9

Cell killing potencies of αHER2-duocarmycin ADCs αHER2-1, αHER2-2 and αHER2-3 on HER2-positive cell lines and the HER2-negative cell line MDA-MB-468.

| | | $IC_{50}$ in nM | | | | | | | |
|---|---|---|---|---|---|---|---|---|---|
| | HER2 | αHER2-1 | αHER2-2 | αHER2-3 | αHER2-6 | Kadcyla | αHEL-1 | DDM (38) | DUBA (10) |
| BT-474 | + | 1.0 (1.2, 0.70) | — | — | — | — | — | — | — |
| Calu-3 | + | 0.9 ± 0.4 | 4 ± 2 | 1.5 ± 0.9 | — | 41 ± 22 | — | — | — |
| HCC-1954 | + | 1 ± 1 | 2 ± 1 | 1 ± 1 | — | 0.50 ± 0.03 | 230 ± 35 | 0.11 ± 0.07[a] | 0.30 ± 0.07[a] |
| JIMT-1 | + | 0.41 ± 0.07 | — | — | — | — | — | 0.14 (0.20, 0.074)[a] | 3 ± 2[a] |
| MDA-MB-361 | + | 0.1 ± 0.02 | — | — | — | — | 29 ± 3 | — | — |
| MDA-MB-453 | + | 0.3 ± 0.1 | — | — | 0.5 ± 0.4[a] | 0.23 ± 0.04[a] | 339 ± 179 | 0.14 (0.15, 0.13)[a] | 0.3 ± 0.1[a] |
| NCI-N87 | + | — | 0.15 ± 0.03[a] | — | 0.3 ± 0.4[a] | 0.10 ± 0.02[a] | — | — | 1.2 ± 0.5[a] |
| SK-BR-3 | + | 0.08 ± 0.03 | 0.16 ± 0.05 | 0.15 ± 0.05 | — | 0.2 ± 0.1 | 42 ± 14 | — | — |

TABLE 9-continued

Cell killing potencies of αHER2-duocarmycin ADCs αHER2-1, αHER2-2 and αHER2-3 on HER2-positive cell lines and the HER2-negative cell line MDA-MB-468.

| | | $IC_{50}$ in nM | | | | | | | |
|---|---|---|---|---|---|---|---|---|---|
| | HER2 | αHER2-1 | αHER2-2 | αHER2-3 | αHER2-6 | Kadcyla | αHEL-1 | DDM (38) | DUBA (10) |
| SK-OV-3 | + | 0.2 ± 0.1 | — | — | — | — | — | — | — |
| MDA-MB-468 | − | 140 ± 47 | 28 ± 7 | 17 ± 4 | — | 43 ± 9 | 56 | 0.02 ± 0.01[a] | 0.06 ± 0.02[a] |

The control ADCs Kadcyla and αHEL-1 were tested in parallel.
HER2-positive cell lines are indicated by plus sign independently of the total amount of receptor on the surface.
Data: IC50 ± SD of N ≥ 3 biological replicates or if less than three indpendent experiments were performed, mean and individual IC50-values in brackets.
Cytotoxicity data are obtained from assays in the 96-well format,
[a]Assay performed in 384-well format.

At early drug development stages, where only in vitro data are available, the therapeutic index can be assessed on the basis of on- and off-target selectivity. Although the target selectivity does not necessarily correlate with an increased therapeutic index in vivo, there are many examples where higher target selectivity also led to improved therapeutic window. Therefore, the selectivity indices (SI) of an ADC towards antigen-expressing cells were calculated according to eq. 4 to rank the ADCs. The selectivity index of an individual ADC was determined by dividing the IC50 on target negative cells by the IC50 on target-positive cells.

$$\text{selectivity index} = \frac{IC_{50} \text{ of } ADC \text{ on target negative cells}}{IC_{50} \text{ of } ADC \text{ on target positive cells}} \quad \text{Eq. 2}$$

Figure 7:
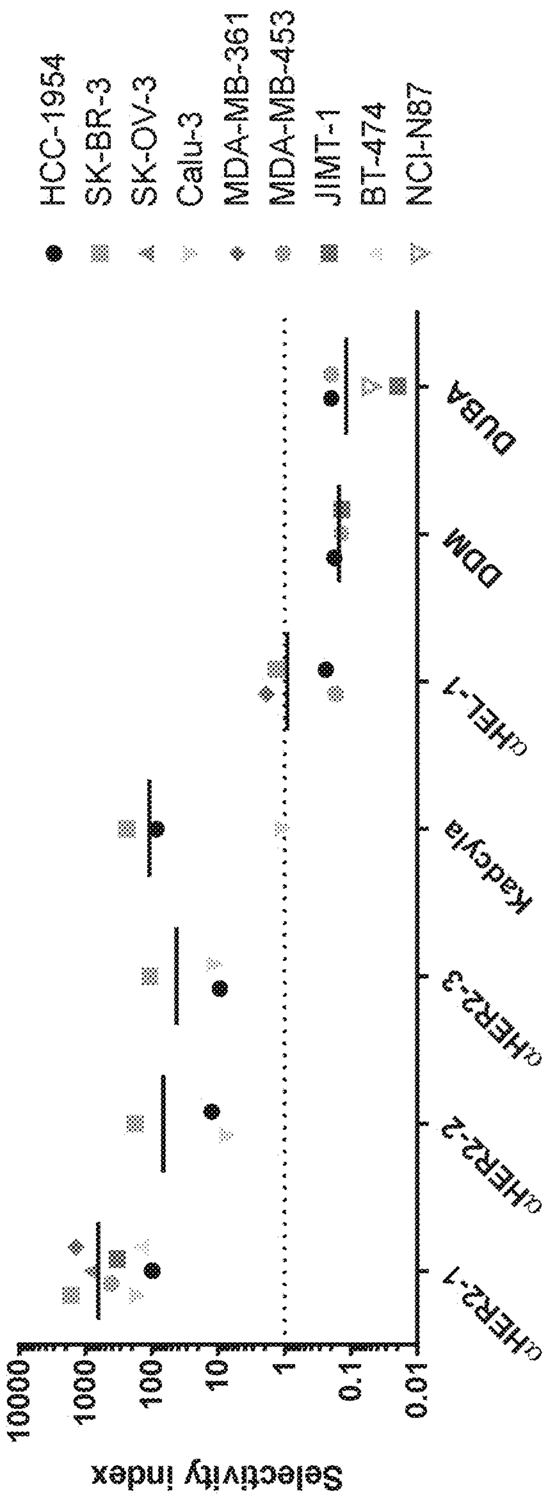
FIG. 7: Selectivity indices of αHER2-duocarmycin ADCs αHER2-1, αHER2-2 and αHER2-3 carrying different linker-drugs, Kadcyla and αHEL-1 on HER2-presenting cell lines. The selectivity indices were calculated by dividing the IC50-value of the individual molecule on HER2-negative cell line MDA-MB-468 by the IC50-value of the molecule on the indicated HER2-positive cell lines. The bar represents the mean of the selectivity indices for every ADC.

Selectivity indices for the individual ADCs are depicted in FIG. 7. The ADC αHER2-1 is the most selective ADC tested with a mean selectivity index of 639. The ADCs αHER2-2 and αHER2-3 with mean selectivity indices of 67 and 43 are weakly less selective than Kadcyla with a mean selectivity index of 110. The non-targeting ADC αHEL-1 has a mean selectivity index of approximately one, which indicates that αHEL-1 exerts cell killing properties target-independent. The small molecule drugs DDM and DUBA killed MDA-MB-468 cells at lower doses than other cell lines studied, leading to selectivity indices of 0.15 and 0.14, respectively Besides the αHER2 and αEGFR mAb, an αMET and a bispecific αMET×EGFR mAb were used for ADC generation. The resulting ADCs were studied for their anti-proliferative properties (table 10). The surface expression of the receptors EGFR and MET was classified as positive for 10- to 100 thousand copies, as double-positive for 100 to 1000 copies and as triple positive for >1000 copies per cell. The ADCs αEGFR-1 and αMET-1 were potent on EGFR- and MET-positive cells in the subnanomolar range, except for αEGFR-1 on MKN-45, where the ADC had an $IC_{50}$ value of 45 nM. αMET×EGFR-1 was less potent on the studied cell lines with $IC_{50}$ values in the single-digit nanomolar range. The ADC αEGFR-7 killed A431 and MDA-MB-468 cells in the subnanomolar range. On EGFR-negative MCF7 cells, the Duocarmycin DM-bearing ADC αEGFR-1 and the DSA-carrying αEGFR-7 were considerably less potent in the single- to doubledigit nanomolar range. The free drugs DDM and DSA were potent on all cell lines regardless of surface receptor status in the subnanomolar range.

TABLE 10

Cell killing potencies of αMET-1, αEGFR-1 and αMET × EGFR-1 ADC on cell lines with differential expression of EGFR and MET.

| | | | $IC_{50}$ in nM | | | | | |
|---|---|---|---|---|---|---|---|---|
| | EGFR | MET | aMET-1 | αMET × EGFR-1 | C-1 | C-7 | DDM | DSA(13) |
| A431 | ++ | + | — | — | 0.17 ± 0.04 | 0.21 ± 0.02 | 0.055 ± 0.005 | 0.21 ± 0.02 |
| A549 | + | + | — | — | * | * | 0.1 ± 0.1 | 0.33 ± 0.07 |
| HepG2 | − | (+) | — | — | * | * | — | — |
| MCF7 | −* | −* | — | — | 27 ± 8 | 9 ± 5 | 0.164 ± 0.004 | 0.06 ± 0.02 |
| MKN-45 | + | ++ | 0.80 (1.2, 0.41) | 2.7 (3.8, 1.6) | 45 (0.72, 88) | — | — | — |
| MDA-MB-468 | +++ | + | 0.91 (0.12, 0.59) | 1.9 ± 0.2 | 0.12 ± 0.08 | 0.06 ± 0.02 | 0.02 ± 0.01 | 0.14 ± 0.07 |
| NCI-H1975 | + | + | 0.14 (0.20, 0.077) | 7.7 (9.3, 6.2) | 0.11 (0.15, 0.058) | — | — | — |

For N < 3 biological replicates the potency is reported as mean of $IC_{50}$ with individual measurements in brackets.
Asteriks indicate that an assay was performed, but the fit was ambigous and no $IC_{50}$-value was obtained.
Receptor densities of 10 × $10^3$-100 × $10^3$ copies were classified as "+", 100 × $10^3$-1000 × $10^3$ classified as "++" and densities >1000 × $10^3$ were classified as "+++".
a: receptor densitiy obtained from internal data.
The $IC_{50}$-values of DDM were already presented in table 9.

Figure 8:
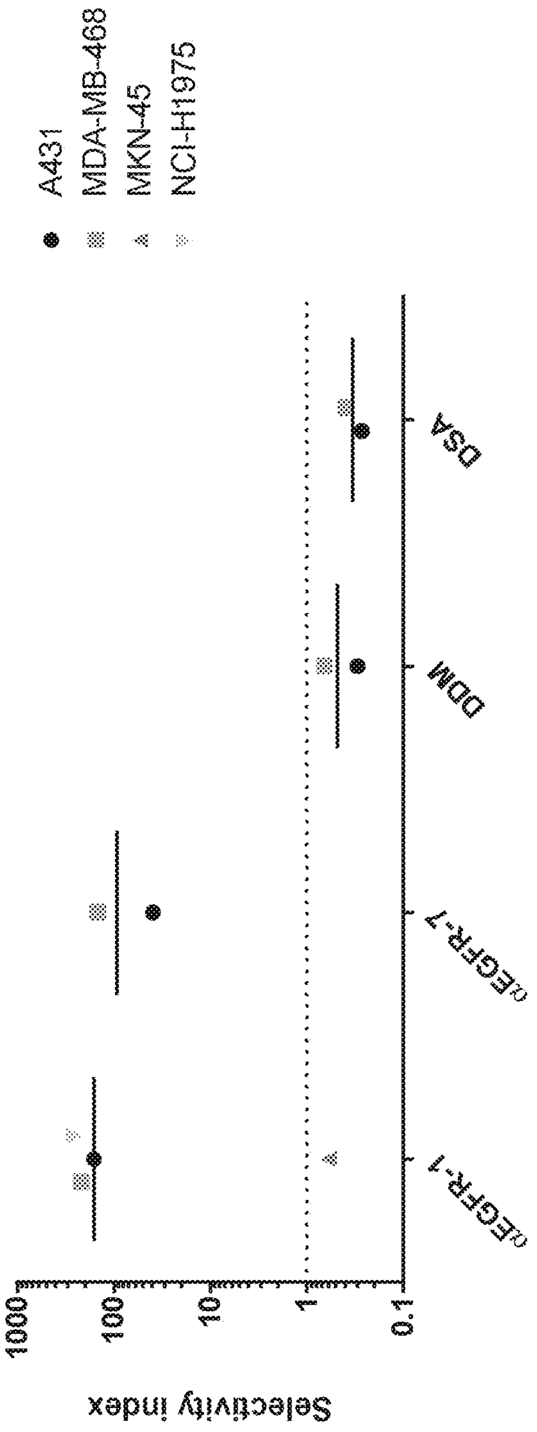
FIG. 8: Selectivity indices of anti-EGFR αEGFR-1 and αEGFR-7 ADCs for EGFR-overexpressing cell lines. The selectivity was calculated by dividing the $IC_{50}$-value of the individual molecules on EGFR-negative cell line MCF7 by the $IC_{50}$-value on the indicated EGFR-positive cell lines. Selectivity for different EGFR-positive cell lines is indicated by shades of grey. The bar represents the mean of selectivity indices over the cell lines treated with a certain ADC.

To further elucidate differences between the individual cetuximab-duocarmycin ADCs, selectivity indices were calculated according to eq. 2 using the $IC_{50}$-values of the ADCs αEGFR-1 and αEGFR-7 and the respective small molecule counterparts on EGFR-positive cell lines and the EGFR-negative cell line MCF7. The results are depicted in FIG. 8. The ADC αEGFR-1 was more selective towards the cell lines A431 (SI=162) and MDA-MB-468 (SI=222) compared to ADC αEGFR-7 (SI=40 on A431 and 148 on MDA-MB-468). αEGFR-1 was selective towards NCI-H1975 cells (SI=257) but showed no selectivity for MKN-45 cells (SI=0.6). The mean selectivity indices for αEGFR-1 accounted to 161 and for αEGFR-7 to 94. The small molecule duocarmycins DDM and DSA did not show selectivity for EGFR-overexpressing cell lines ($SI_{mean}$=0.5 and 0.3, respectively).

Example 6: Synergy of Duocarmycin-ADCs with ATRi

Figure 9:
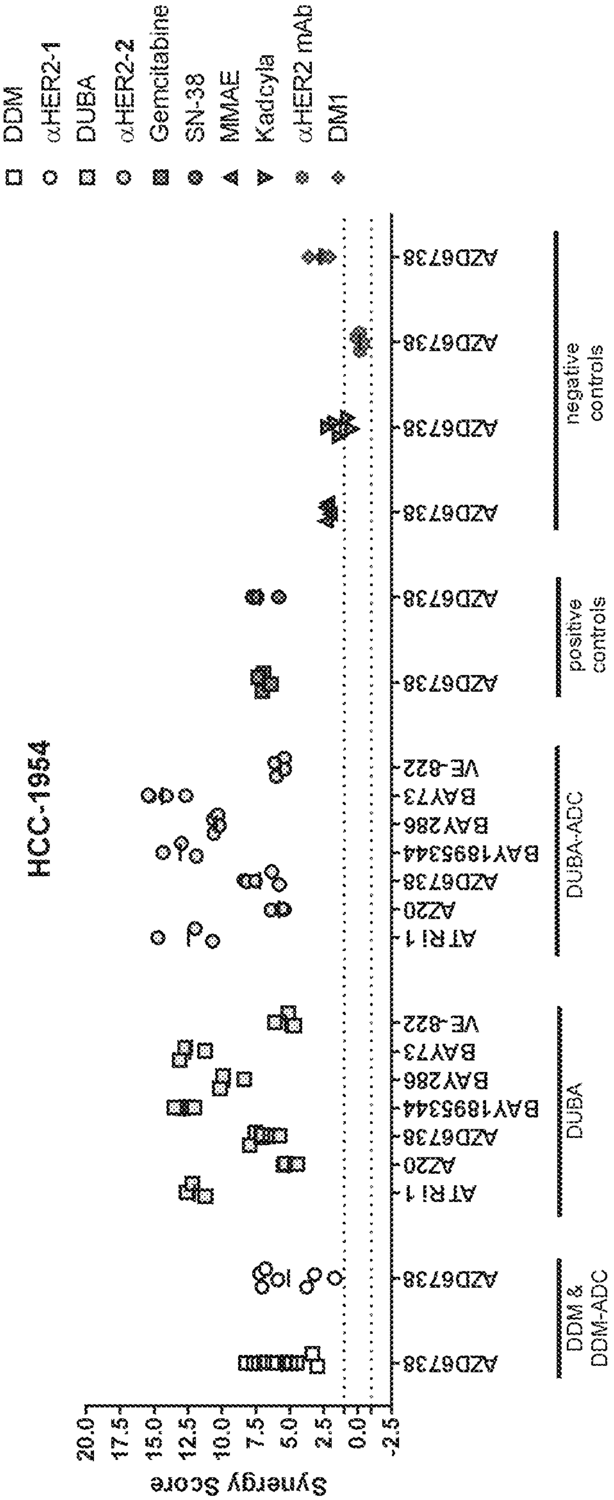
FIG. 9: Synergy scores of duocarmycin-based ADCs and small molecules in combination with AZD6738 on HCC-1954. Individual data points are displayed as well as the mean of the individual points represented by a bar.

Synergy of Combinations of αHER2-Duocarmycin ADCs and ATRi HCC-1954 were treated with DDM, DUBA and the corresponding DDM-bearing αHER2-1 and DUBA-carrying ADC αHER2-2 (FIG. 9) in combination with AZD6738 for 6 d. Then, cell cytotoxicity was determined using CellTiter-Glo kit. Luminescence was read on Envision reader and data were evaluated using GeneData Screener. The combination of DDM with AZD6738 (S=5.6+1.7) was comparably synergistic as the corresponding ADC αHER2-1 (S=5.1±2.0). The same conclusion can be drawn for the combination of DUBA with AZD6738 (6.9±0.7) and αHER2-2 plus AZD6738 (7.2±1.0).

As positive controls, SN-38 and Gemcitabine were combined with AZD6738 on HCC-1954 cells. SN-38 as well as Gemcitabine synergized with AZD6738 (S=7.2+0.8 and S=6.9±0.3). The microtubule inhibitor MMAE, however, synergized weakly with the ATRi AZD6738 (S=2.2+0.1) as well as microtubule inhibiting ADC Kadcyla combined with AZD6738 (S=1.3±0.7) on HCC-1954 cells. In this case, one measurement was excluded that yielded a synergy score of 6.4. Thus, αHER2 mAb trastuzumab and DM1 were combined with AZD6738 to elucidate the influence of the two molecular portions on the synergistic effects. Trastuzumab did not synergize with AZD6738 on HCC-1954 cells (S=−0.2±0.2) while DM1 and AZD6738 led to synergistic cell killing (S=2.8+0.5).

Furthermore, the influence of different ATRi on the synergistic effects of the combination with ADC αHER2-2 or the corresponding small molecule DUBA was studied on HCC-1954 cells. The combination of αHER2-2 with ATRi 1 was significantly stronger (P=0.03) with a score of 12.5±1.7 than the combination of αHER2-2 with AZD6738 on HCC-1954 cells. When combining the ADC αHER2-2 with BAY1895344 it was also significantly stronger (P=0.003) with a synergy score of 13.1±1.0 than αHER2-2 combined with AZD6738. The ATRi VE-822 and AZ20 synergized with αHER2-2 comparable to AZD6738 with synergy scores of 5.7±0.3 and 5.8±0.4, respectively. BAY73 combined with αHER2-2 had the highest synergy score with 14.4±1.1. BAY286 plus αHER2-2 had a synergy score in the mid range of 10.4±0.2. The synergy scores of DUBA combined with the ATRi AZ20 (S=5.1±0.5), ATRi 1 (S=12.0±0.6), BAY1895344 (S=12.8±0.5), BAY73 (S=12.4±0.8), BAY286 (S=9.5±0.8) and VE-822 (S=5.3±0.6) on HCC-1954 cells were in good comparison to the ADC αHER2-2 combined with the respective same ATRi.

Figure 10:
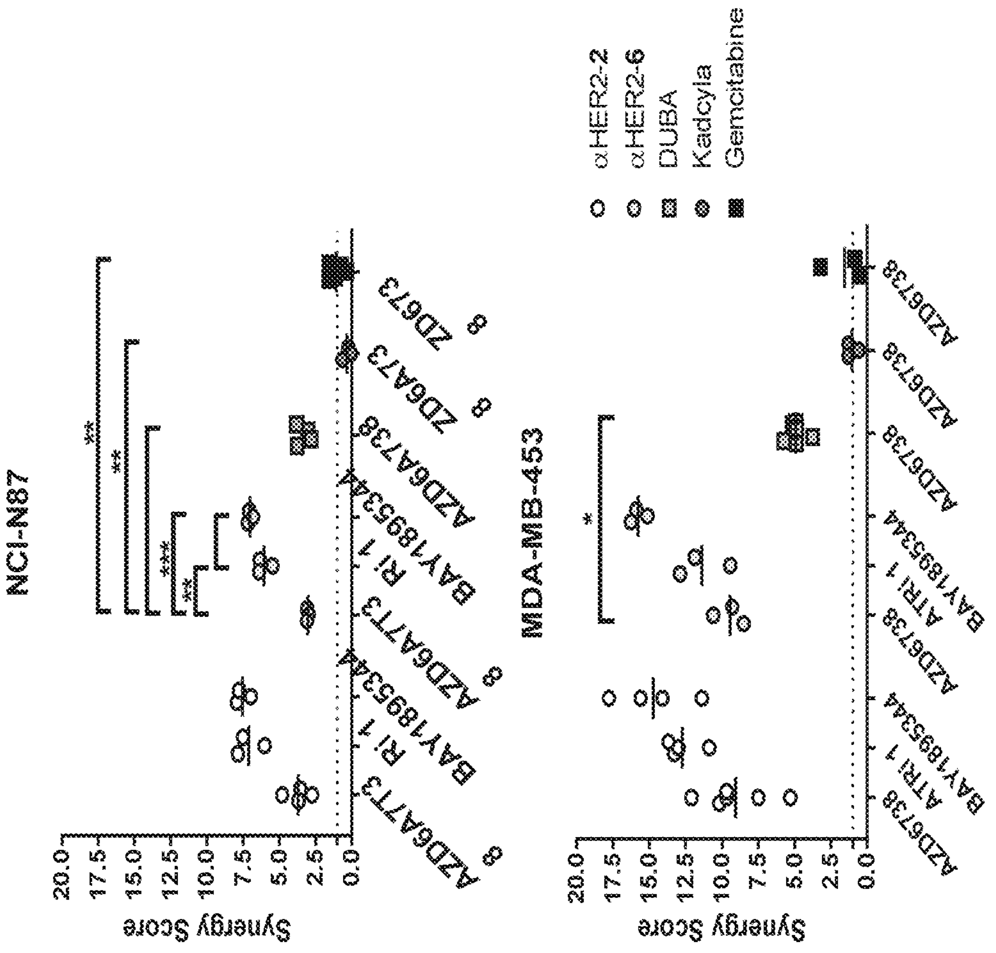
FIG. 10: Synergy scores of combinations of duocarmycin-bearing ADCs αHER2-2 and αHER2-6 with different ATRi on NCI-N87 or MDA-MB-453 cells. As controls, the small molecules DUBA and Gemcitabine and, as negative control, Kadcyla were included. Bars represent the mean of independent biological replicates.

In a next experiment, the ADCs αHER2-2 and αHER2-6 were combined with the three ATR inhibitors AZD6738, ATRi 1 and BAY1895344 on NCI-N87 and MDA-MB-453 cells. As a control, the small molecules DUBA and Gemcitabine and as ADC control Kadcyla were combined with the ATRi AZD6738 (FIG. 10). On NCI-N87 cells αHER2-2 synergized in increasing order with the ATRi AZD6738 (S=3.7±0.7), ATRi 1 (S=7.1±0.8) and BAY1895344 (S=7.6+0.4). The combination of αHER2-2 plus ATRi 1 (P=0.008) and BAY1895344 (P=0.0007) were significantly more synergistic than the combination of the ADC plus ATRi AZD6738. The same trend was observed for the combination of another DUBA-ADC αHER2-6. Again, the combination with AZD6738 (S=3.0±0.05) showed the lowest score, ATRi 1 (S=6.1±0.4) a mid-range and BAY1895344 (S=7.0+0.2) the highest score. In direct comparison, S of the combination of αHER2-6 with AZD6378 was significantly lower than the combination of αHER2-6 with ATRi 1 (P=0.009) and BAY1895344 (P=0.0002). As a positive control, DUBA was combined with the ATRi AZD6738. A synergy score of S=3.1+0.6 proves the synergy between the duocarmycin-derivative and the ATRi. The combination of αHER2-6 with AZD6738 was comparably synergistic as the combination of its small molecule counterpart DUBA with AZD6738 (P=0.3). The negative control Kadcyla showed only additive effects when combined with AZD6738 (S=0.3±0.2), while the benchmark Gemcitabine barely exceeded the cutoff score when combined with the ATRi AZD6378 (S=1.1±0.5). The duocarmycin-ADC αHER2-6 synergized significantly stronger with the ATRi AZD6738 compared to the negative control Kadcyla (P=0.003) and the positive control Gemcitabine (P=0.001).

Similar results were obtained on MDA-MB-453 cells. Here, αHER2-2 synergized with the ATRi AZD6738 (S=9.1±2.1), ATRi 1 (S=13.3±0.3) and BAY1895344 (S=14.7±2.3) in increasing order. The same trend was observed for αHER2-6 plus AZD6738 (S=9.5±0.9), ATRi 1 (S=11.4+1.4) and BAY1895344 (S=15.8±0.5). Gemcitabine synergized slightly stronger with AZD6738 on MDA-MB-453 (S=1.6±1.2) than on NCI-N87. The negative control combination of Kadcyla with AZD6738 reached a synergy score of 1.1±0.3 which is just above the cutoff score indicating very weak synergy. The positive control DUBA synergized with AZD6738 also on MDA-MB-453 cells (S=5.0±0.5) but significantly weaker than the combination of αHER2-6 with the corresponding ATRi (P=0.01).

Figure 11:
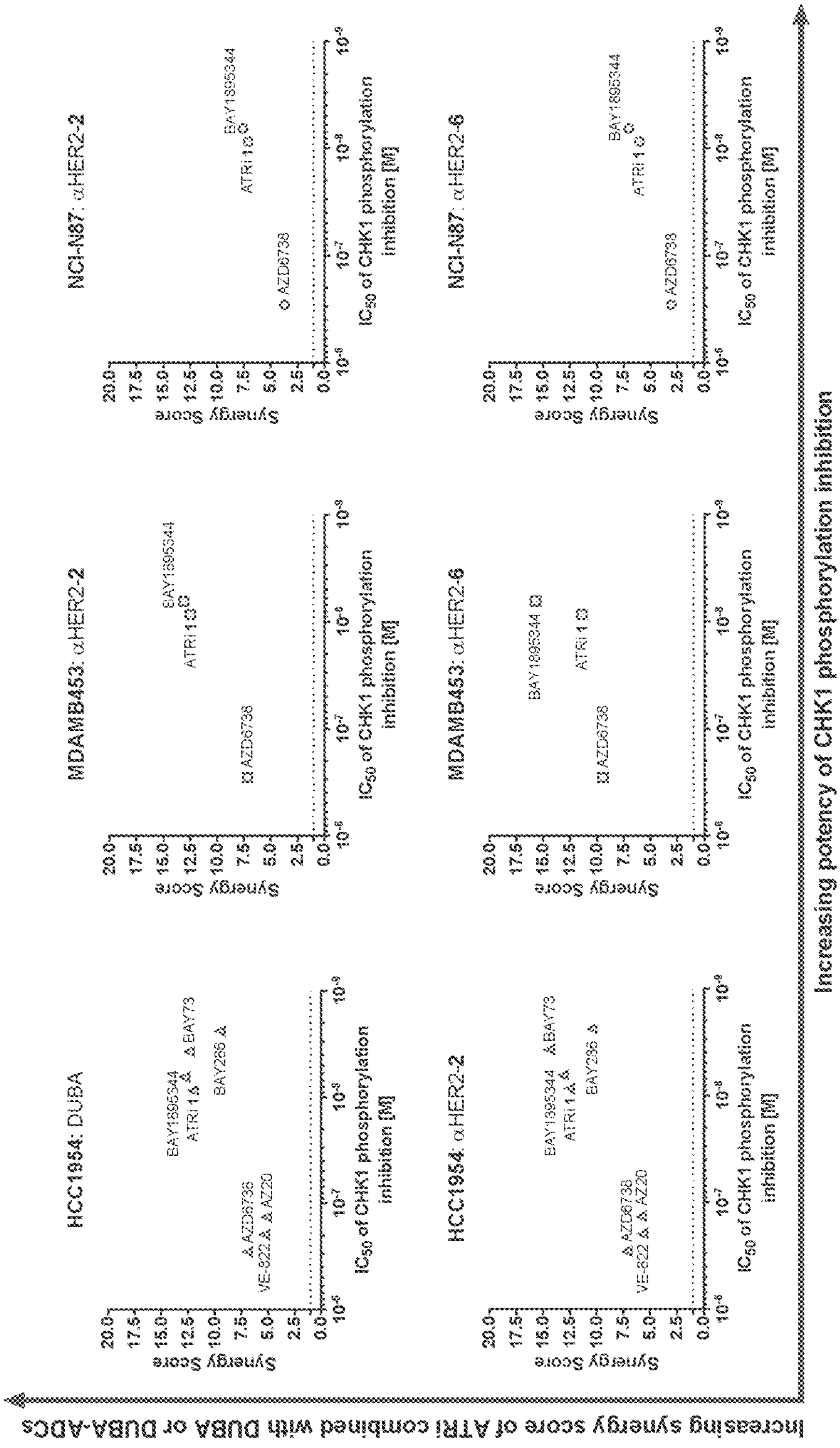
FIG. 11: Correlation between synergy score and cellular CHK1 phosphorylation inhibition on HT29 cells. The more potent the ATRi in terms of CHK1 phosphorylation inhibition the higher the synergy score. This correlation was shown for combinations of the small molecule drug DUBA with several ATRi on HCC-1954 cells. The correlation was reproduced for the same ATRi combined with the ADC αHER2-2 on HCC-1954. A subset of the ATRi was combined with αHER2-2 and another DUBA-based ADC αHER2-6 on MDA-MB-453 and NCI-N87 cells.

A total of seven ATRi were investigated in this study to elucidate the effect of the ATRi on the combination effects with duocarmycin and duocarmycin-based ADCs on HCC-1954, MDA-MB-453 and NCI-N87 cells. The synergy scores of the individual ATRi (as presented in FIG. 9 and FIG. 10) combined with the duocarmycin DUBA or DUBA-based ADCs were plotted against their potency to inhibit the phosphorylation and thus activation of CHK1 after HT29 were stressed by treatment with hydroxyurea. The plots are depicted in FIG. 11. A correlation between the ATRi potency and the synergy scores was observed for the small molecule DUBA with the ATRi on HCC-1954. This finding was confirmed with the ADC αHER2-2 combined with the ATRi library on HCC-1954. The same correlation was observed for αHER2-2 and αHER2-6 combined with a subset of ATRi on MDA-MB-453 and NCI-N87 cells.

Synergy of Combinations of αEGFR-Duocarmycin ADCs and ATRi

Figure 12:
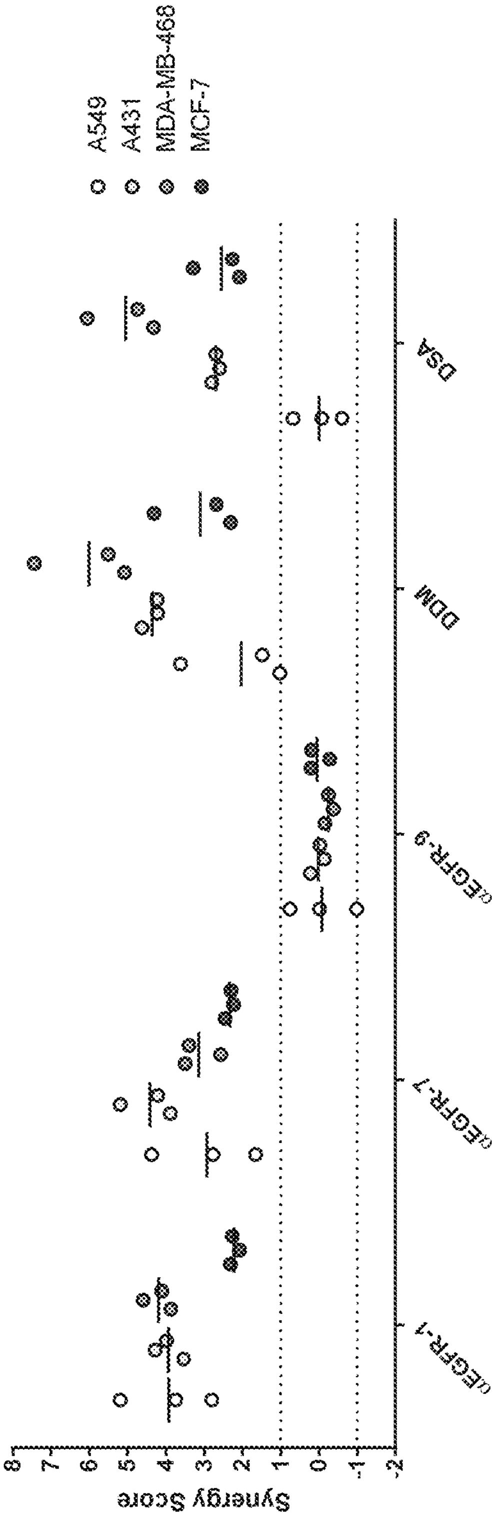
FIG. 12: Synergy scores of combinations of cetuximab-duocarmycin ADCs with the ATRi AZD6738 on EGFR-positive cell lines and the EGFR-negative cell line MCF7. As a control, Cetuximab-MMAE was combined with the ATRi AZD6738. Individual data points are displayed as well as the mean of the experiments

To validate that the concept of combining duocarmycin-modified ADCs with ATRi can be translated to additional antibodies, cetuximab-based duocarmycin-ADCs were investigated. Therefore, the EGFR-positive cell lines A549, A431 and MDA-MB-468 as well as EGFR-negative MCF7 cells were treated with DDM-based αEGFR-1, DSA-based αEGFR-7 in combination with AZD6738. As controls, the cells were also treated with the MMAE-ADC αEGFR and the small molecule duocarmycins DDM and DSA. After 6 d of treatment, cell viability was determined using CellTiter-Glo reagent. Luminescence was read on an Envision reader and evaluation took place using GeneData Screener. Data are depicted in FIG. 12. The negative control ADC αEGFR had synergy scores in the range of additivity. The positive control DDM had synergy scores ranging from 2.0±1.1 on A549 to 6.0±1.0 on MDA-MB-468 cells. The synergy scores of the small molecule DSA were comparable on A431, MDA-MB-468 and MCF7. However, DSA did not synergize with AZD6738 on A549 cells but showed additive effects. While the synergy of the combination of αEGFR-1 plus AZD6738 was very similar on A549 (S=3.9±1.0), A431 (S=3.9±0.3) and MDA-MB-468 (S=4.2+0.3) cells, the synergy score on MCF7 (S=2.2±0.1) was significantly lower compared to αEGFR-1 combined with AZD6738 on MDA-MB-468 (P=0.006) or A431 (P=0.01). However, the effects were less distinct for the combination of the DSA-ADC αEGFR-7 combined with the ATRi. The synergy score of C-7 plus AZD6738 amounted to 4.4±0.6 on A431, 2.9±1.1 on A549 and 3.2±0.4 on MDA-MB-468 cells. This combination reached a synergy score of 2.3±0.1 on the EGFR-negative cell line MCF7, which is significantly lower than the combination given to A431 cells (P=0.03).

Dose-Reduction of αHER2-Duocarmycin Combinations with ATRi

A strategy for improved safety of a combination therapy is the reduction of the administered doses. It was demonstrated in the previous chapters that duocarmycin-bearing ADCs combined with ATRi unfolded synergistic toxic effects towards cancer cells. But the expression of synergistic effects in terms of a synergy score did not allow an estimation on how much the dose of the drugs in a combination might be lowered while maintaining the same cellular effects. Therefore, it was studied how strong the potency of the duocarmycin-bearing ADCs was increased when ATRi were added at sub-efficacious doses.

Figure 13:
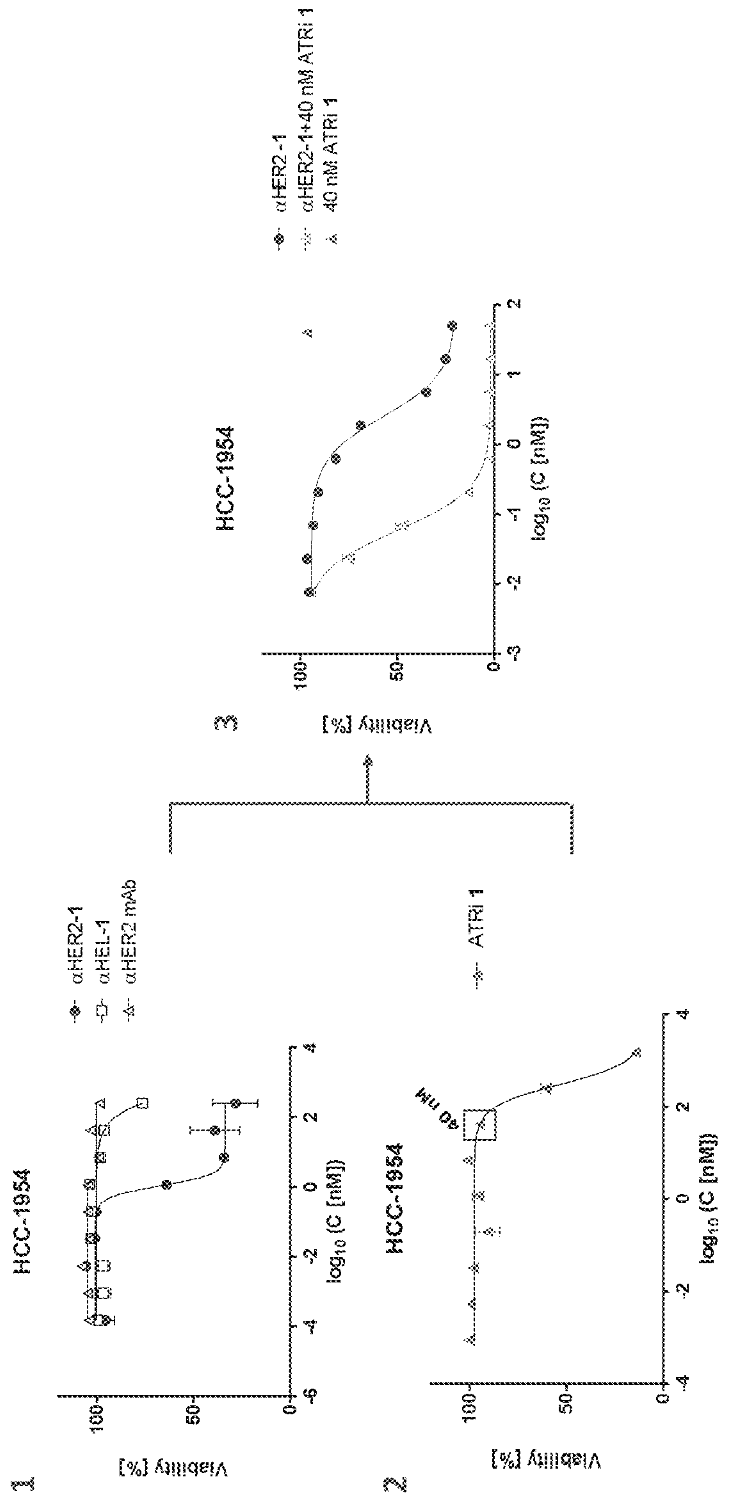
FIG. 13: MNED-curve shift assay for the determination of dose-reduction indices as a 3-step process. 1) Cytoxicity of the ADC αHER2-1 was confirmed in a cell viability experiment. 2) The inhibitor potency of ATRi 1 was titrated to identify the MNED. 3) MNED-curve shift assay is performed by serial diluting the ADC αHER2-1. The serial dilution of αHER2-1 was added to HCC-1954 cells either alone or with ATRi 1 at the previously determined MNED. This led to a leftward shift of the ADC toward lower potencies. The inhibitor was added at MNED to the cells as a quality control demonstrating no effect on cell viability.

The determination of dose-reduction indices (DRI) in a maximum non-efficacious dose (MNED) curve-shift assay is a 3-step process as depicted exemplarily in FIG. 13. The cytotoxicity of the ADC is confirmed in a cell viability assay in an initial step. Here, HCC-1954 cells were treated with αHER2-1, the αHER2 mAb trastuzumab (T) and a control ADC αHEL-1 for 6 d and cell viability was measured using CellTiter-Glo kit. While αHER2-1 had an $IC_{50}$-value of 1.1 nM, the naked mAb did not show any anti-proliferative effects. The isotype control ADC αHEL-1 reduced the cell viability at 250 nM to 75% but was considerably less cytotoxic as αHER2-1. In the second step. the MNED of the ATRi was determined. Therefore, the cells were treated with ATRi 1 and the dose-response curve (DRC) was plotted to identify MNED which was in this case 40 nM. It was proceeded to the last step with these data, the MNED curve-shift assay. Therefore, HCC-1954 cells were treated with a serial dilution of αHER2-1 or a serial dilution of αHER2-1 supplemented with 40 nM ATRi 1. In order to obtain a full DRO for the combination, the starting concentration of the ADC was lowered compared to the experiment in step 1. The $IC_{50}$-value of αHER2-1 was 2.5 nM. The combination of αHER2-1 with 40 nM ATRi 1 had a potency of 0.059 nM. This potentiation of the combination compared to the ADC alone can be expressed as a DRI of 42. ATRi 1 did not reduce cell viability at 40 nM.

MNEDs were determined for AZD6738 and VE-822 on a panel of HER2-positive cell lines and on the HER2-negative cell line MDA-MB-468, because cell lines might respond differently to the combination treatment of αHER2-1 and ATRi. In addition, the MNED of BAY73 and ATRi 1 were determined on HCC-1954 cells. The MNEDs for the HER2-positive cell lines and the HER2-negative cell line MDA-MB-468 are summarized in table 11table.

TABLE 11

Summary of maximum non-efficacious doses on HER2-positive cell lines and HER2-negative cell line MDA-MB-468.

| | MNED in nM | | | |
|---|---|---|---|---|
| Cell line | AZD6738 | BAY73 | ATRi 1 | VE-822 |
| BT-474 | 1000 | — | — | 1000 |
| Calu-3 | 400 | — | — | 80 |
| HCC-1954 | 250 | 14 | 40 | 250 |
| JIMT-1 | 80 | — | — | 80 |
| MDA-MB-361 | 111 | — | — | — |
| MDA-MB-453 | 111 | — | — | 40 |
| MDA-MB-468 | 300 | — | — | 300 |
| SK-OV-3 | 150 | — | — | 125 |
| SK-BR-3 | 150 | — | — | 125 |

Then, the cells were treated with either ADC alone or with a combination of αHER2-1 with AZD6738 or VE-822 at the corresponding MNED. The $IC_{50}$-values of the monotreatment and the combination treatment are summarized in table 12. Although, in all cases the $IC_{50}$-values of the combination was lower than the $IC_{50}$-value of the ADC alone, only in few cases the difference was significant. The potency of the ADC alone was 1±1 nM on HCC-1954 cells. In combination with 250 nM AZD6738 or 250 nM VE-822, the potency of the combination was lowered to 0.3±0.3 nM or 0.3±0.2 nM, respectively. The potentiation effect was significant in both cases (P=0.03 and P=0.03, respectively). The $IC_{50}$-value of αHER2-1 on JIMT-1 was 0.41±0.07 nM. The combination of αHER2-1 with 80 nM of the ATRi AZD6738 led to a significant higher potency with an $IC_{50}$-value of 0.19±0.03 nM (P=0.03). The potency of the combination of αHER2-1 with 111 nM AZD6738 on MDA-MB-361 ($IC_{50}$=0.03±0.01) was also significantly more potent than the monotreatment with αHER2-1 ($IC_{50}$=0.10±0.02). The potentiation effects were also studied on the HER2-negative cell line MDA-MB-468. The potency of the ADC alone was 140±47 nM. If 300 nM AZD6738 or 300 nM VE-822 were added, the potency was 19±4 nM or 44±17 nM. The combination of αHER2-1 with AZD6738 or VE-822 was significantly more potent than the monotherapy with αHER2-1 alone (P=0.00009 or P=0.0004, respectively).

TABLE 12

Potencies of ADC αHER2-1 alone or in combination with AZD6738 and VE-822 on a HER2-positive cell panel and a HER2-negative cell line MDA-MB-468. The ATRi were added at constant concentration to the ADC αHER2-1 (MNED, see table 11). Potencies of the ADC αHER2-1 on the cell panel are already listed in table 9, but repeated for comparison. Data are mean ± SD for N ≥ 3 biological replicates (except for BT-474 where experiments were conducted twice). P-values were added if the combination treatment was significantly more potent than the monotreatment.

| | | $IC_{50}$ in nM | | |
|---|---|---|---|---|
| | HER2 | αHER2-1 | αHER2-1 + AZD6738 | αHER2-1 + VE-822 |
| BT-474 | + | 1.0 (1.2, 0.70) | 0.086 (0.095, 0.077) | 0.079 (0.10, 0.057) |
| Calu-3 | + | 0.9 ± 0.4 | 0.3 ± 0.1 | 0.6 ± 0.2 |
| HCC-1954 | + | 1 ± 1 | 0.3 ± 0.3 (P = .03) | 0.3 ± 0.2 (P = .03) |
| JIMT-1 | + | 0.41 ± 0.07 | 0.19 ± 0.03 (P = .03) | 0.24 ± 0.02 |
| MDA-MB-361 | + | 0.10 ± 0.02 | 0.03 ± 0.01 (P = .02) | N/D |
| MDA-MB-453 | + | 0.3 ± 0.1 | 0.05 ± 0.01 | 0.13 ± 0.03 |
| SK-BR-3 | + | 0.08 ± 0.03 | 0.036 ± 0.006 | 0.05 ± 0.02 |
| SK-OV-3 | + | 0.2 ± 0.1 | 0.07 ± 0.04 | 0.05 ± 0.02 |
| MDA-MB-468 | − | 140 ± 47 | 19 ± 4 (P = .00009) | 44 ± 17 (P = .0004) |

Figure 14:
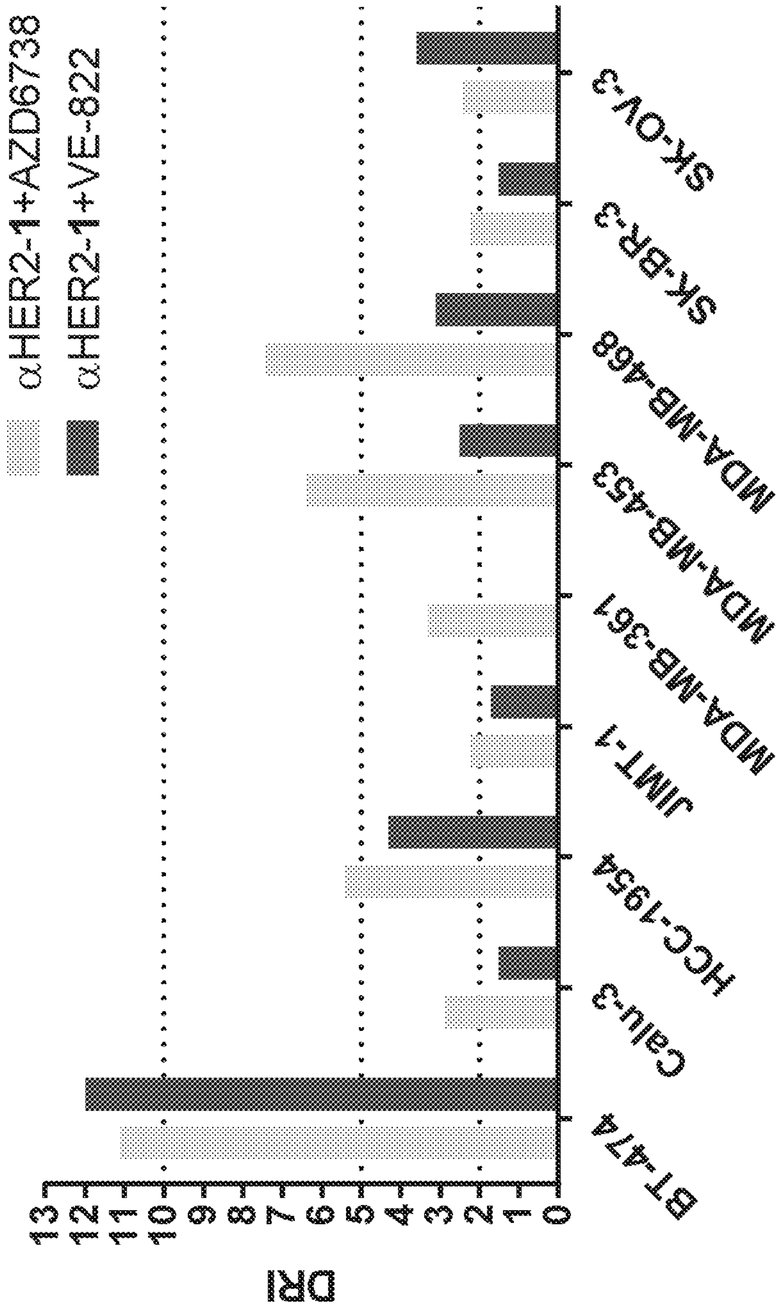
FIG. 14: Dose-reduction indices of the combination of αHER2-1 with AZD6738 or VE-822 on a panel of HER2-positive cell lines and the HER2-negative cell line MDA-MB-468. The ATRi were given at their individual MNED (table 11Table) in the combination groups.

The potentiation effects of combination treatment versus monotreatment can be elucidated in a more detailed fashion by calculating dose-reduction indices using eq. 1. The potency of a combination is enhanced compared to the monotherapy with increasing DRI. The results of this calculation are displayed in FIG. 14. The DRIs of the combination αHER2-1 plus VE-822 on Calu-3, JIMT-1 and SK-BR-3 were below two. In most of the cases, DRIs of two to five were reached. The combination of αHER2-1 with AZD6738 exceeded a DRI of five on HCC-1954

(DRI=5.4), MDA-MB-453 (DRI=6.4) and MDA-MB-468 (DRI=7.4). DRIs greater than ten were reached for αHER2-1 combined with AZD6738 (DRI=11.1) and VE-822 (DRI=12.0) on BT-474 cells.

Figure 15:
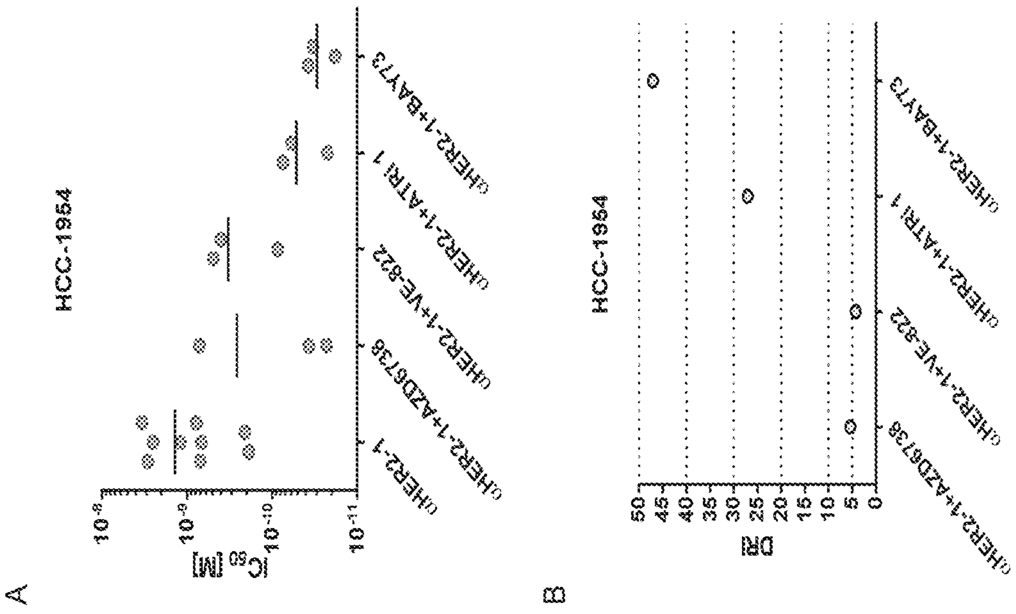
FIG. 15: Combination of ADC αHER2-1 with ATRi AZD6738, VE-822, ATRi 1 and BAY73 on HCC-1954 cells. The ATRi are given at their individual MNEDs in the combination treatment groups as summarized in table 11. A) The $IC_{50}$-values of the single agent and combination groups are depicted as individual data points. The black bar indicates the mean of the $IC_{50}$-values for each group. B) DRI of αHER2-1 combined with the ATRi are plotted. The DRI were calculated from the $IC_{50}$-values shown in A).

Furthermore, HCC-1954 cells were co-treated with ADC αHER2-1 and the ATRi AZD6738, VE-822, ATRi 1 and BAY73 to study the effect of the ATRi on the DRI (FIG. 15). The ADC alone had an $IC_{50}$-value of 1.4±1.2 nM, while the combination of ADC with 250 nM AZD6738 was 5.4-fold more potent with $IC_{50}$=0.26±0.33 nM (P=0.03). The combination of αHER2-1 with VE-822 was comparably potent ($IC_{50}$=0.33±0.17 nM) and again significantly more potent than the monotreatment with αHER2-1 (P=0.03). A DRI of 4.3 was obtained for αHER2-1 combined with VE-822. The combination of ADC with 40 nM ATRi 1 or 14 nM BAY73 strongly potentiated ADC potency ($IC_{50}$=0.074±0.022 nM and $IC_{50}$=0.030±0.008 nM, respectively). The combination of αHER2-1 and ATRi 1 achieved a DRI of 27.1, while the combination of the ADC with BAY73 led to a 47.1-fold potentiation. It can be stated that αHER2-1 plus BAY73 or ATRi 1 are significantly more potent than αHER2-1 alone (P=0.01 and P=0.01, respectively) based on these data. For clarity, the DRIs of the combinations of αHER2-1 with the four different ATRi AZD6738, VE-822, ATRi 1 and BAY73 are depicted in FIG. 15 B.

Major differences in the synergy scores were observed when combining small molecule duocarmycins with AZD6738. Thus, potentiation effects of DUBA-based ADCs should be compared to potentiation effects of DDM-carrying ADCs when combined with different ATRi. The potencies of DDM-based ADC αHER2-1 alone or in combination with AZD6738 and VE-822 are already summarized in table 12. In addition to these experiments, potencies of DUBA-based ADCs αHER2-2 and αHER2-3 alone or in combination with AZD6738 and VE-822 were studied on HER2-positive cell lines HCC-1954, Calu-3 and SK-BR-3 and HER2-negative cell line MDA-MB-468. While αHER2-2 and αHER2-3 had $IC_{50}$-values in the single-digit nanomolar range on HCC-1954 and Calu-3 cells, the ADCs were potent in the subnanomolar range on SK-BR-3 cells. On MDA-MB-468 cells, the DUBA-based ADCs were considerably less potent than on the HER2-positive cell lines, with $IC_{50}$-values in the double digit nanomolar range. The effects of the ADCs were potentiated when adding AZD6738 or VE-822 at their respective MNED for every cell line to the ADCs. Although this trend was observed for all the combinations of αHER2-2 and αHER2-3 with AZD6738 and VE-822, the effects were significant only for the potentiation effects of αHER2-2 plus AZD6738 (P=0.04) and VE-822 (P=0.04).

TABLE 13

Potencies of the DUBA-bearing ADCs αHER2-2 and αHER2-3 as well as control ADC Kadcyla alone or in combination with constant doses of AZD6738 and VE-822 at MNED.

| | | $IC_{50}$ in nM | | | | |
|---|---|---|---|---|---|---|
| | | αHER2-2 | | | αHER2-3 | |
| | HER2 | — | AZD6738 | VE-822 | — | AZD6738 |
| HCC-1954 | + | 2 ± 1 | 0.10 ± 0.02 | 0.097 ± 0.006 | 2 ± 1 | 0.09 ± 0.02 |
| Calu-3 | + | 4 ± 2 | 0.7 ± 0.4 | 0.931 ± 0.164 | 1.5 ± 0.9 | 0.4 ± 0.1 |
| SK-BR-3 | + | 0.16 ± 0.05 | 0.035 ± 0.007 | 0.061 ± 0.015 | 0.15 ± 0.05 | 0.039 ± 0.001 |
| MDA-MB-468 | − | 28 ± 6 | 2.3 ± 0.4 | 5.14 ± 2.056 | 17 ± 4 | 1.4 ± 0.3 |

TABLE 13-continued

Potencies of the DUBA-bearing ADCs αHER2-2 and αHER2-3 as well as control ADC Kadcyla alone or in combination with constant doses of AZD6738 and VE-822 at MNED.

| | $IC_{50}$ in nM | | | |
|---|---|---|---|---|
| | αHER2-3 | Kadcyla | | |
| | VE-822 | — | AZD6738 | VE-822 |
| HCC-1954 | 0.15 ± 0.04 | 0.50 ± 0.03 | 0.4 ± 0.2 | 0.3 ± 0.2 |
| Calu-3 | 0.6 ± 0.2 | 41 ± 22 | 37 ± 22 | 41 ± 23 |
| SK-BR-3 | 0.071 ± 0.005 | 0.2 ± 0.1 | 0.19 ± 0.02 | 0.12 ± 0.07 |
| MDA-MB-468 | 5 ± 3 | 43 ± 9 | 30 ± 1 | 31 ± 1 |

The MNEDs of ATD6738 and VE-822 for each are summarized in table 11table.
Data are mean ± SD of N ≥ 3 biological replicates.

The control ADC Kadcyla was comparably potent HCC-1954, SK-BR-3 and MDA-MB-468. On Calu-3, Kadcyla was considerably less potent than the duocarmycin-carrying ADCs αHER2-2 and αHER2-3. However, this effect was not significant.

Figure 16:
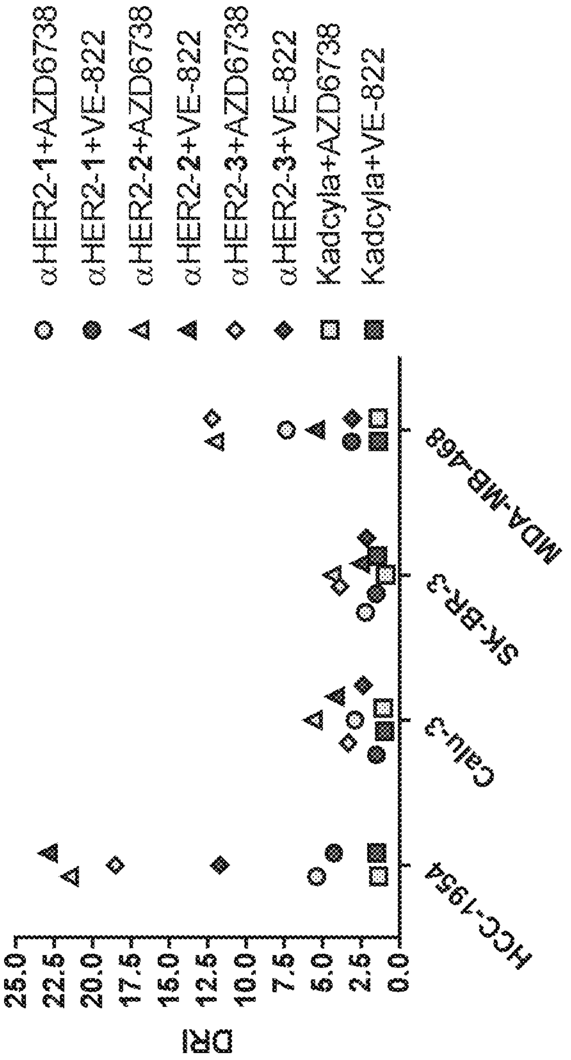
FIG. 16: Comparison of DRIs of αHER2-1, αHER2-2 and αHER2-3 and Kadcyla when combined with constant concentrations of the ATRi AZD6738 and VE-822. The DRIs were calculated using the $IC_{50}$-values in table 12 and table 13. The ATRi were added to the ADC at MNED (table 11Table).

A summary of DRIs of DDM-bearing ADC αHER2-1, DUBA-carrying αHER2-2 and αHER2-3 and control ADC Kadcyla combined with AZD6738 and VE-822 at constant dose on HCC-1954, Calu-3, SK-BR-3 and MDA-MB-468 is displayed in FIG. 16. On HCC-1954 cells, the highest DRIs were reached with the DUBA-ADCs. The potency of αHER2-2 was enhanced strongly by addition of AZD6738 (21.5-fold) or VE-822 (22.9-fold). Weaker potentiation effects were achieved by combining αHER2-3 with AZD6738 (18.5-fold) or VE-822 (11.7-fold) at MNED. The combination of DDM-bearing ADC αHER2-1 with AZD6738 reached considerably lower DRIs of 5.4 or 4.3 when AZD6378 or VE-822 were added, respectively. The negative control ADC Kadcyla had DRIs of 1.4 and 1.5 when combined with AZD6738 or VE-822, respectively. The trend of DUBA-bearing ADCs combined with ATRi being superior to DDM-bearing ADC αHER2-1 plus ATRi was reproduced on Calu-3, SK-BR-3 and MDA-MB-468 although less pronounced. Kadcyla combinations with the ATRi had consistently DRIs<2.

Figure 17:
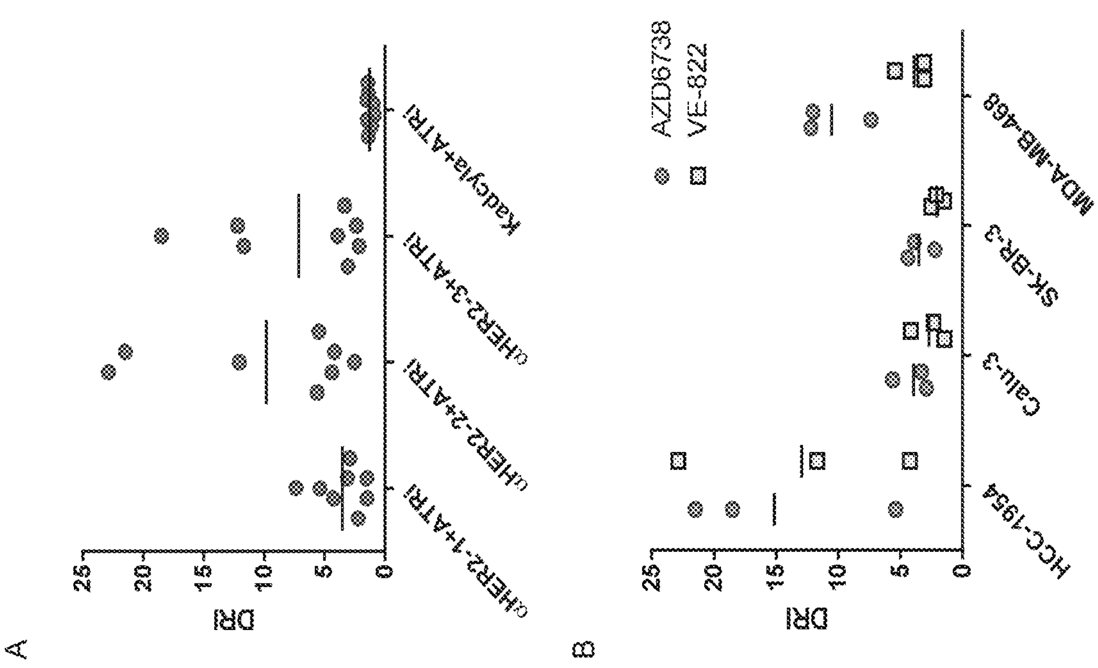
FIG. 17: DRIs of duocarmycin-bearing ADCs combined with ATRi. A) DRI of the combination of ATRi with duocarmycin-bearing ADCs αHER2-1, αHER2-2 and αHER2-3 as well as Kadcyla were condensed regardless of cell line. Individual data points are displayed and the mean is indicated by a black bar. These data are already presented in. B) DRI of ATRi combined with duocarmycin-bearing ADCs. The results were condensed regardless of which ADC-variant was used. Individual data points are displayed and the mean is indicated by a black bar.

In order to compare the potentiation effects of DDM-bearing ADCs with DUBA-carrying ADCs and the negative control Kadcyla, DRIs were condensed and depicted in FIG. 17 A. The potentiation effects of DUBA-based ADCs αHER2-2 and αHER2-3 when combined with ATRi were stronger (DRI=9.8 and 7.2, respectively) than the potentiation of DDM-based αHER2-1 combinations with ATRi (DRI=3.6). The mean DRI of Kadcyla plus ATRi amounts to 1.3. Furthermore, the potentiation effects of the ATRi AZD6738 and VE-822 when added to the duocarmycin-bearing ADCs on the different cell lines were compared (FIG. 17 B). In all cases, the mean of DRIs of the combination AZD6738 with duocarmycin-ADCs was higher compared to the combination of VE-822 with duocarmycin-based ADCs.

Figure 18:
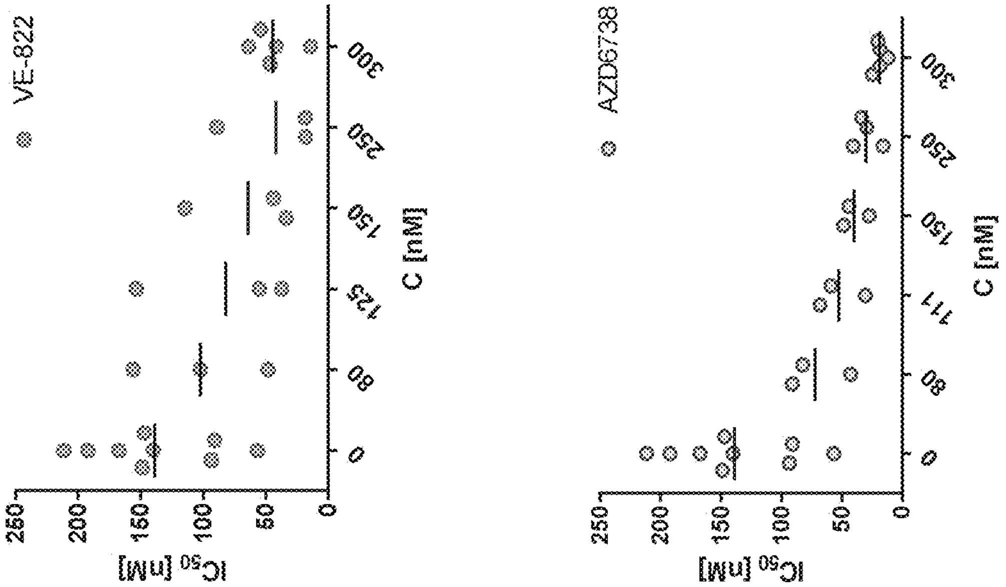
FIG. 18: Dose-dependency of potentiation effects. MDA-MB-468 cells were treated with ADC αHER2-1 and increasing doses of VE-822 (left) or AZD6738 (right). Individual data points are displayed and the mean is represented by a black bar.

The cell lines studied here had differential tolerability of the ATR inhibitors, reflected by the different MNEDs. Selectivity indices were introduced that allowed the comparison of different ADCs. However, in the case of combination treatment, varying constant concentrations of ATRi were added to the cells together with the duocarmycin-ADC. This impaired the calculation of selectivity indices for drug combinations. As a result, it was necessary to determine the potency of ADC combined with constant concentrations of ATRi on MDA-MB-468. In the following experiments the dependency of the DRI on the constant dose of ATRi added to the ADC in combination experiments was investigated. FIG. 18 illustrates that the $IC_{50}$-value of the ADC alone was decreased by the addition of either VE-822 or AZD6738 in a dose-dependent manner.

Figure 19:
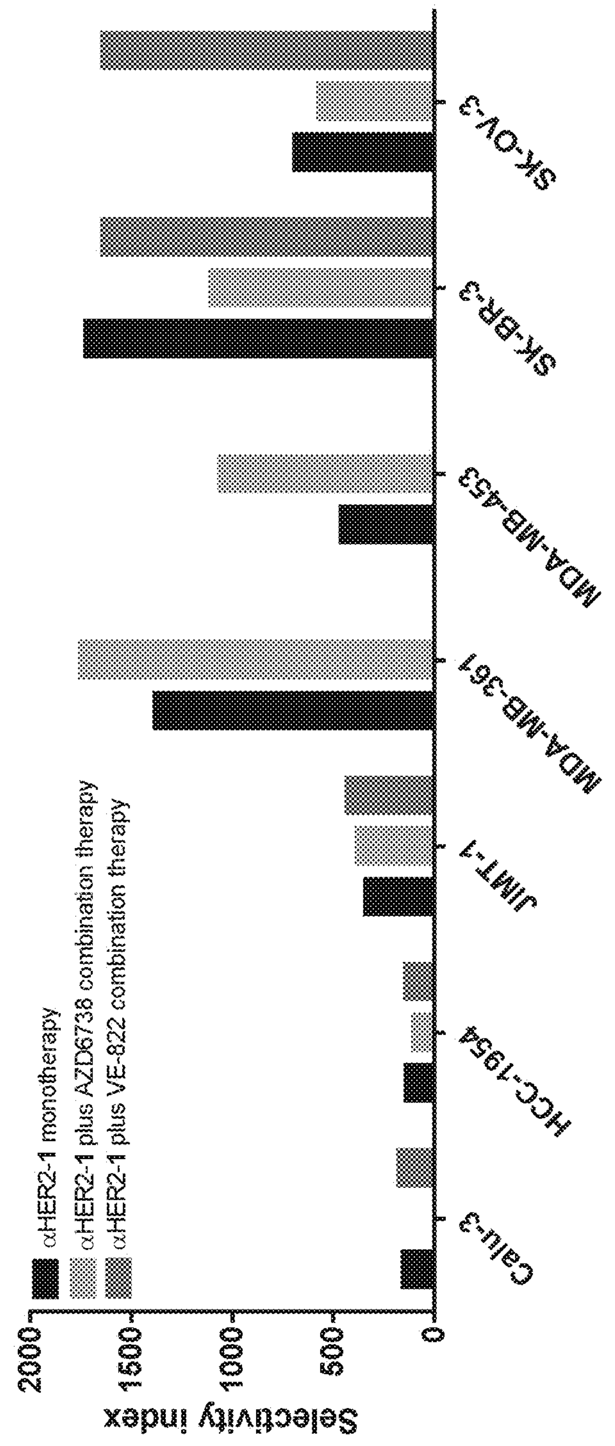
FIG. 19: Comparison of selectivity indices for monotherapy and combination therapy for αHER2-1 combined with either AZD6378 or VE-822 at the respective MNED. Selectivity indices were calculated according to eq. 2 for cells treated with ADC only.

The data presented in FIG. 18 enabled the calculation of selectivity indices according to eq. 2. Therefore, the $IC_{50}$-value of αHER2-1 combined with a constant concentration of 111 nM AZD6378 on MDA-MB-468 (53±16 nM) was divided by the $IC_{50}$-value of αHER2-1 combined with 111 nM AZD6738 on MDA-MB-453 (0.05±0.01 nM). This resulted in a selectivity index of 1010 for the combination treatment at that specific dose of ATRi. In comparison to that, the selectivity index of the monotherapy using αHER2-1 amounted to 414. Selectivity indices for the monotherapy, combination treatment of αHER2-1 with AZD6738 or VE-822 are depicted in FIG. 19. Since the MNED of the ATRi on BT-474 and the MNED of AZD6738 on Calu-3 exceeded the MNED of the HER2-negative cell line MDA-MB-468, no selectivity index was calculated in these cases. Furthermore, MDA-MB-468 cells were not treated with 40 nM VE-822, so no SI was calculated for that case.

The selectivity of αHER2-1 was 153 towards Calu-3 cells, 138 towards HCC-1954 cells and 337 towards JIMT-1 cells. Higher selectivity indices were reached for αHER2-1 on MDA-MB-453 (SI=460) and SK-OV-3 (SI=690). Triple digit indices were obtained when MDA-MB-361 cells or SK-BR-3 cells were treated with αHER2-1 (SI=1380 or 1725, respectively). When treating HCC-1954, SK-BR-3 and SK-OV-3 cells with αHER2-1 and AZD6738 simultaneously, the SI were decreased compared to monotherapy. The SI towards HCC-1954 amounts to 100, towards SK-BR-3 to 1105 and towards SK-OV-3 cells to 571 when treated with the combination. The selectivity was increased when αHER2-1 and AZD6738 were given to JIMT-1 (SI=379), MDA-MB-361 (SI=1749) or MDA-MB-453 cells (SI=1060) at the same time. The combination treatment of Calu-3 cells with VE-822 and αHER2-1 had slightly increased selectivity towards Calu-3 (SI=172) compared to monotherapy. On HCC-1954 cells the selectivity of the monotherapy (SI=138) and the combination therapy (SI=140) was equal. On JIMT-1 cells the combination of αHER2-1 with VE-822 was more selective towards antigen-positive cells (SI=429) than the treatment with αHER2-1 alone, while on SK-BR-3 cells a lower SI of 1640 was obtained for the combination when compared to monotherapy. αHER2-1 combined with VE-822 was comparably more selective towards SK-OV-3 cells (SI=1640) than the ADC alone.

Figure 20:
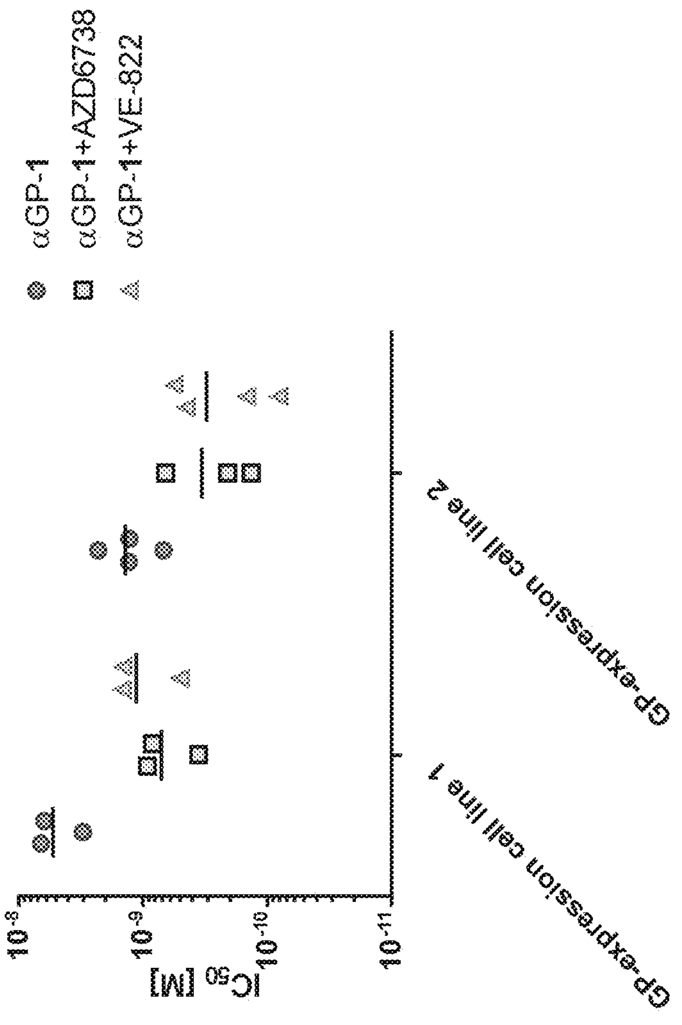
FIG. 20: Potencies of αGP-1 as single agent or combined with constant doses of ATRi AZD6738 and VE-822 on GP-positive cells MDA-MB-468 and WISH. The inhibitors were given at MNED to the cells. The individual $IC_{50}$-values of biological replicate experiments are displayed.

Potentiation Effects of Glycoprotein Binding-Duocarmycin DM ADC when Combined with ATRi Furthermore, it was studied whether the potentiation effects observed with the αHER2-based ADCs on HER2-positive cells might be translated to other targeted antigens, two glycoprotein (GP)-expressing cell lines were treated with GP-binding ADC αGP-1 alone or ADC combined with the ATRi AZD6738 and VE-822 at their respective MNED for 6 d. Afterwards, the cell viability was determined using CellTiter-Glo assay. The potencies of the cell viability assays are summarized in FIG. 20. The ADC as single agent had an $IC_{50}$-value of 5±2 nM on GP-expressing cell line 1 and 1.4±0.6 nM on GP-expressing cell line 2. The potency of the ADC αGP-1 was enhanced 7.5-fold on GP-expressing cell line 1 cells by the addition of 300 nM AZD6738, which resulted in an $IC_{50}$-value of 0.7±0.3 nM. The addition of 300 nM VE-822 decreased the potency of the combination to 1.1±0.5 nM which is 4.7-fold more potent than the single agent. On GP-expressing cell line 2 similar results were obtained. αGP-1 combined with 300 nM AZD6738 had an $IC_{50}$-value of 0.3±0.2 nM, which is the equivalent of a 4.2-fold dose-reduction. The addition of 300 nM VE-822 to the ADC decreased the potency 4.5-fold leading to a potency of 0.3±0.2 nM.

Example 8: In Vivo Efficacy and Tolerability of αHER2-6 Combination with ATR Inhibitors AZD6738 and ATRi 1

After it was successfully confirmed that duocarmycins also synergize with ATRi when conjugated to an antibody the combination was investigated in vivo to study efficacy and tolerability of the combination treatment. 10 days after subcutaneous injection of NCI-N87 cells into H2d Rag2 mice, animals were randomized and treated either with vehicle, with a single intravenous dose of 1.0 mg $kg^{-1}$ αHER2-6 or with 50 mg $kg^{-1}$ ATRi AZD6738 or ATRi 1, given once daily over 14 days per oral. The combination effects were studied by giving αHER2-6 combined with AZD6738 or αHER2-6 plus ATRi 1 at the same dosing and schedule as the single agents.

The vehicle group was terminated on day 24, because the tumor volumes met the criterium for termination. The treatment with AZD6738 was not statistically different from the vehicle-treated group (P=0.2). In case of the ATR Inhibitor ATRi 1, a transient tumor stasis was induced until day 8 but the tumor rapidly progressed to reach the endpoint. However, the tumor-growth inhibition was statistically significantly stronger compared to the vehicle group (P=0.003). The administration of the single agent αHER2-6 led to transient tumor stasis until day 9 when the tumor progressed. ADC-treatment resulted in statistically significant reduction of tumor volume compared to the vehicle-receiving group (P=0.0002) and the ATRi monotherapy groups treated with AZD6738 ($P=9\times10^{-9}$) and ATRi 1 (P=0.006).

The combination therapy groups αHER-6 plus AZD6738 or ATRI 1 however induced statistically significantly stronger anti-tumoral effects than the vehicle-treated group (P=0.00003 or P=0.00002, respectively). The combination αHER-6 plus AZD6738 induced tumor stasis until day 66 when this group was terminated because three animals had skin lesions on the tumors. The treatment of mice with a combination of αHER-6 and ATRi 1 led to tumor regression until day 63 when the tumors began to progress again.

Figure 21:
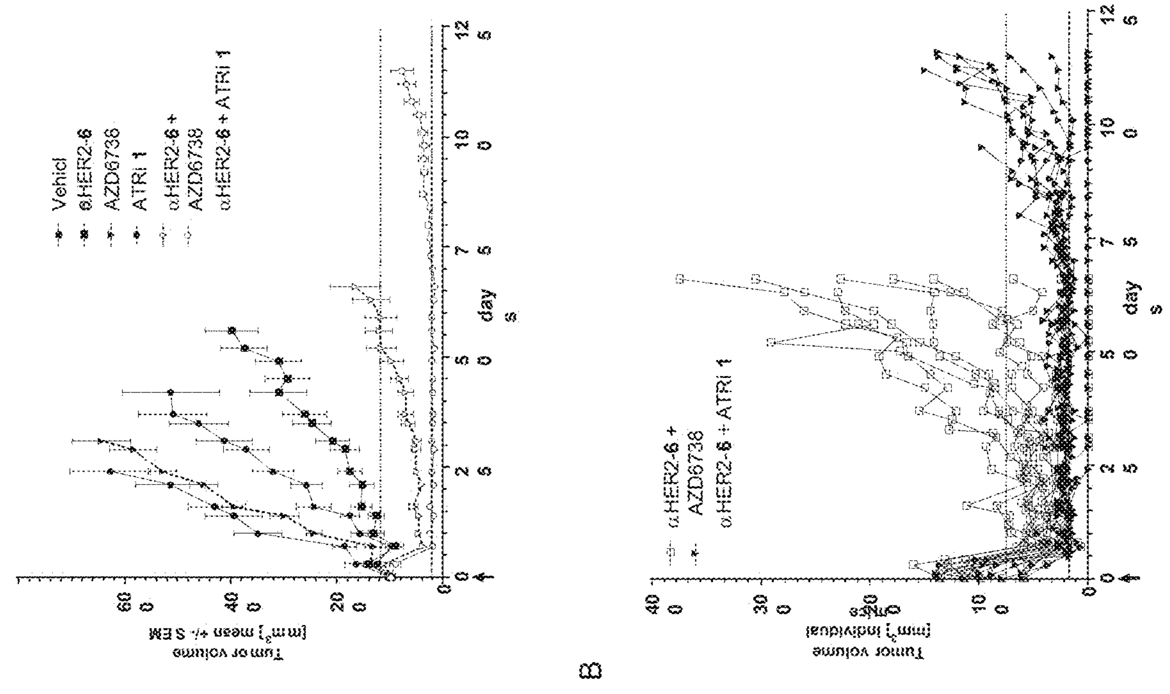
FIG. 21: Therapeutic efficacy of αHER2-6 combined with the ATR inhibitors AZD6738 and ATRi 1 in H2d Rag2 mice bearing NCI-N87 xenografts. A) Antitumor activity was assessed as change in tumor volume compared to vehicle, and the single agents αHER2-6, AZD6738 and ATRi 1. Therefore mice (N=10 per group) were treated with 1.0 mg $kg^{-1}$ αHER2-6 intravenously, 50 mg $kg^{-1}$ AZD6738 or ATRi 1 per oral once daily for two weeks or a combination of αHER2-6 plus AZD6738 or αHER2-6 plus ATRi 1 at the same doses and schedules as the single agents beginning at day 0 as indicated by the arrow. The upper dotted line indicates an increase in tumor volume of 73%, while the lower dotted line indicates a decrease in tumor volume by 66% as compared to day 0. The range between the dotted lines indicates tumor stasis and below the lower line tumor regression. B) Tumor volume of the combination groups αHER2-6 plus AZD6738 or αHER2-6 plus ATRi 1 at the level of individual animals. Treatment with αHER2-6 plus AZD6738 led to 1/10 cures, while the treatment with αHER2-6 plus ATRi 1 led to 2/10 cures.

Remarkably, in the combination treatment group that received αHER-6 plus AZD6738, one mouse showed a complete response ($V_{tumor}<20\ mm^3$) which lasted until the group was terminated (day 66). In the group treated with αHER-6 plus ATRi 1 a total of three complete responses were observed. In one mouse, this effect was transient lasting around 90 days until the tumor progressed and in case of the other two mice, the animals showed tumor free survival until the end of the observation period (15 weeks). The data are displayed in FIG. 21 at the level of the treatment groups (FIG. 21 A) and at the level of individual animals in the combination groups (FIG. 21 B).

Figure 22:
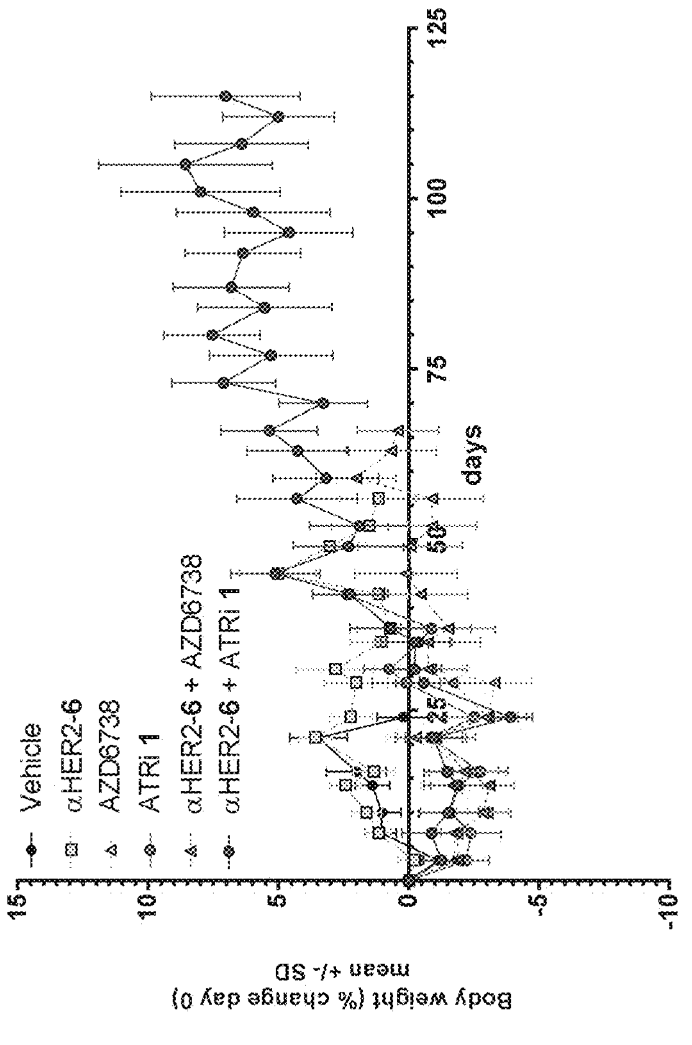
FIG. 22: Therapeutic tolerability of αHER2-6 combined with the ATR inhibitors AZD6738 and ATRi 1 in H2d Rag2 mice bearing NCI-N87-xenografts. The body weight was assessed as a measure of tolerability of the combination treatment as well as the corresponding single agents αHER2-6, AZD6738 and ATRi 1

The tolerability of the anti-cancer treatment was assessed considering the overall condition of the animal as well as body-weight changes of the mice (FIG. 22). The body-weight of mice treated with the ADC αHER2-6 did not decrease and was comparable to the body-weight of the vehicle-treated group at all time points. However, mice treated with the ATRi AZD6738 and ATRi 1 lost weight compared to the vehicle group but body-weight loss was still below 5%. Mice receiving combination treatment with αHER2-6 and AZD6738 or ATRi 1 showed a body-weight profile comparable to mice treated with the ATRi AZD6738 or ATRi 1 as single agents.

It can be concluded that the ADC αHER2-6, the ATRi AZD6738 and ATRi 1 as well as the combination treatments were well tolerated.

The invention claimed is:

1. A method for treating a HER2 expressing cancer in a subject in need thereof, comprising administering to the subject in any order an Ataxia telangiectasia and Rad3-related (ATR) inhibitor and a duocarmycin bearing antibody-drug conjugate (ADC), wherein the ADC comprises a heavy chain comprising the amino acid sequence according to SEQ ID NO: 17 and a light chain comprising the amino acid sequence according to SEQ ID NO: 18.

2. The method according to claim 1, wherein the ATR inhibitor is selected from the group consisting of Compound 1, Compound 2, Compound 3, Compound 4, Compound 5, Compound 6, Compound 7, Compound 8, or a pharmaceutically acceptable salt thereof, wherein compounds 1-8 are defined as follows:

Compound 1

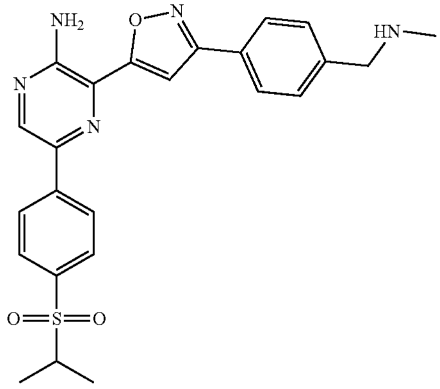
,

-continued

Compound 2

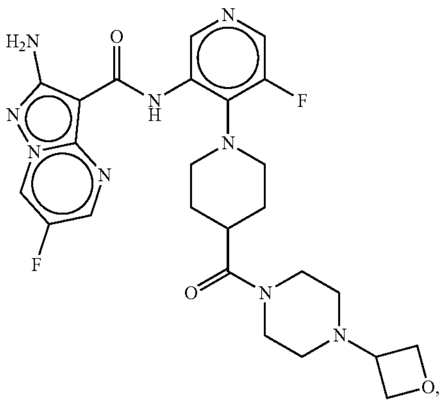

Compound 3

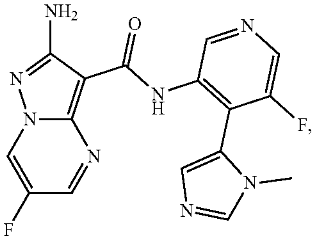

Compound 4

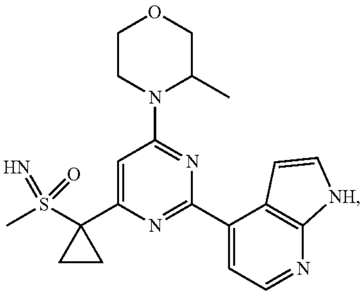

Compound 5

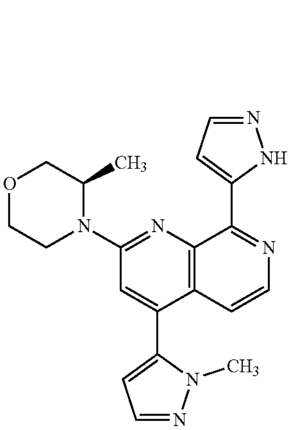

-continued

Compound 6

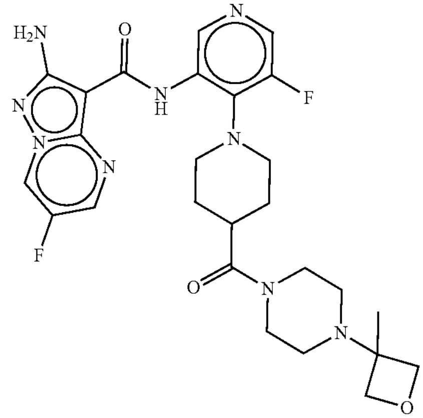

Compound 7

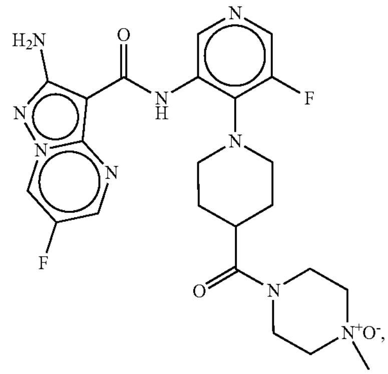

and

Compound 8

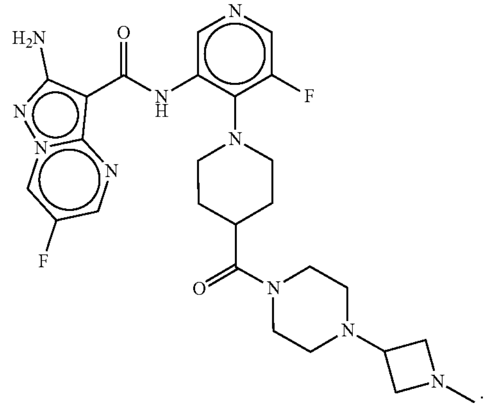

3. The method according to claim 2, wherein the ATR inhibitor is Compound 1, or a pharmaceutically acceptable salt thereof.

4. The method according to claim 1, wherein the subject underwent at least one round of prior cancer therapy; wherein, optionally, the cancer was resistant or became resistant to prior therapy.

5. The method according to claim 1, further comprising administering a chemotherapy (CT), radiotherapy (RT), or chemotherapy and radiotherapy (CRT) to the subject.

6. The method according to claim 5, wherein the ATR inhibitor and the duocarmycin bearing ADC are administered during the lead phase, whereas during the maintenance phase the ATR inhibitor but not the duocarmycin bearing ADC are administered.

7. The method according to claim 6, wherein the ATR inhibitor and the duocarmycin bearing ADC are administered during the lead phase, whereas A during the maintenance phase the duocarmycin bearing but not the ATR inhibitor are administered.

8. The method according to claim 1, wherein the duocarmycin bearing ADC is selected from the group consisting of DUBA, DDM and DSA.

9. The method according to claim 1, wherein the heavy chain comprises a C-terminal sortase-A motif LPETGS of SEQ ID NO: 31.

10. The method according to claim 1, wherein the heavy chain additionally comprises a (G4S)3-spacer and a sortase-A motif LPETGS of SEQ ID NO: 30.

11. The method according to claim 1, wherein the cancer is selected from the group consisting of small-cell lung cancer (SCLC), non-small-cell lung cancer (NSCLC), squamous cell carcinoma of the head and neck (SCCHN), colorectal cancer (CRC), primary neuroendocrine tumors and sarcoma or PARPi-resistant recurrent cancer.

12. The method according to claim 2, wherein the ATR inhibitor is Compound 3 or a pharmaceutically acceptable salt thereof, or Compound 4 or a pharmaceutically acceptable salt thereof, or Compound 5 or a pharmaceutically acceptable salt thereof, wherein compounds 3-5 are defined as follows:

Compound 3

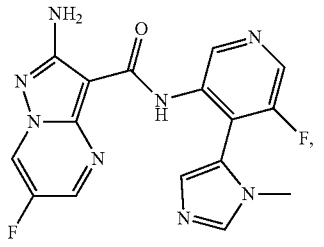

-continued

Compound 4

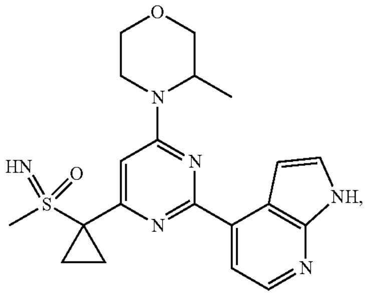

Compound 5

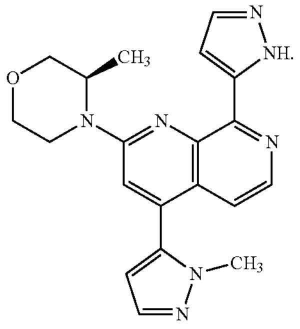

* * * * *